(12) United States Patent
Chandrapati et al.

(10) Patent No.: US 10,047,334 B2
(45) Date of Patent: *Aug. 14, 2018

(54) BIOLOGICAL STERILIZATION INDICATOR

(71) Applicant: 3M INNOVATIVE PROPERTIES COMPANY, St. Paul, MN (US)

(72) Inventors: Sailaja Chandrapati, Woodbury, MN (US); Heather M. Webb, Woodbury, MN (US); Jeffrey C. Pederson, Minneapolis, MN (US); Jeffrey D. Smith, Marine on St. Croix, MN (US); RuthAnn R. Duda, Eagan, MN (US); Brian J. Engel, Houston, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 244 days.

This patent is subject to a terminal disclaimer.

(21) Appl. No.: 15/064,918

(22) Filed: Mar. 9, 2016

(65) Prior Publication Data

US 2016/0186120 A1    Jun. 30, 2016

Related U.S. Application Data

(63) Continuation of application No. 13/881,741, filed as application No. PCT/US2011/058257 on Oct. 28, 2011, now Pat. No. 9,322,046.

(Continued)

(51) Int. Cl.
   *B01L 3/00*    (2006.01)
   *C12M 3/00*    (2006.01)
   (Continued)

(52) U.S. Cl.
   CPC ............ *C12M 37/06* (2013.01); *C12M 23/32* (2013.01); *C12M 25/06* (2013.01); *C12Q 1/04* (2013.01); *C12Q 1/22* (2013.01); *G01N 21/6486* (2013.01)

(58) Field of Classification Search
   CPC .. C12M 37/06; C12Q 1/22; B01L 3/50; B01L 2300/0835
   See application file for complete search history.

(56) References Cited

U.S. PATENT DOCUMENTS

| D222,352 S | 10/1971 | Ferro |
|---|---|---|
| 3,814,522 A | 6/1974 | Clark |

(Continued)

FOREIGN PATENT DOCUMENTS

| DE | 19742949 | 4/1998 |
|---|---|---|
| EP | 0000063 | 12/1978 |

(Continued)

OTHER PUBLICATIONS

Kato, "How to use the UV-visible Spectroscopy System," Agilent 8453, Manual for UV Measurement, Feb. 14, 2003.

(Continued)

*Primary Examiner* — Nathan A Bowers

(57) ABSTRACT

A biological sterilization indicator (BI). The BI can include a housing, and a container positioned in the housing. The container can contain a liquid and at least a portion of the container can be frangible. The BI can further include a first chamber and a second chamber. The second chamber can include at least one source of biological activity. The BI can further include a substrate positioned in the housing between the first chamber and the second chamber. The substrate can be positioned in fluid communication with the first chamber and the second chamber, and the substrate can be further positioned such that the substrate is not in direct contact with the source of biological activity.

16 Claims, 7 Drawing Sheets

Related U.S. Application Data

(60) Provisional application No. 61/408,966, filed on Nov. 1, 2010, provisional application No. 61/408,977, filed on Nov. 1, 2010.

(51) Int. Cl.
  *C12M 1/12* (2006.01)
  *C12Q 1/22* (2006.01)
  *G01N 21/64* (2006.01)
  *C12Q 1/04* (2006.01)
  *C12M 1/00* (2006.01)

(56) References Cited

U.S. PATENT DOCUMENTS

| | | |
|---|---|---|
| 4,291,122 A | 9/1981 | Orelski |
| 4,461,837 A | 7/1984 | Karle |
| 4,528,187 A | 7/1985 | Truglio |
| 4,528,268 A | 7/1985 | Andersen |
| 4,565,783 A | 1/1986 | Hansen |
| 4,591,566 A | 5/1986 | Smith |
| 4,732,850 A | 3/1988 | Brown |
| 4,885,253 A | 12/1989 | Kralovic |
| 5,073,488 A | 12/1991 | Matner |
| 5,089,413 A | 2/1992 | Nelson |
| 5,094,955 A | 3/1992 | Calandra |
| 5,167,923 A | 12/1992 | Van Iperen |
| 5,223,401 A | 6/1993 | Foltz |
| 5,232,838 A | 8/1993 | Nelson |
| 5,242,370 A | 9/1993 | Silver |
| 5,252,484 A | 10/1993 | Matner |
| 5,316,906 A | 5/1994 | Haugland |
| 5,405,580 A | 4/1995 | Palmer |
| 5,418,167 A | 5/1995 | Matner |
| 5,443,986 A | 8/1995 | Haughland |
| 5,482,171 A | 1/1996 | Palmer |
| 5,529,931 A | 6/1996 | Narayan |
| 5,552,320 A | 9/1996 | Smith |
| 5,601,998 A | 2/1997 | Mach |
| D380,555 S | 7/1997 | Kurosaki |
| 5,658,084 A | 8/1997 | Wirt |
| D383,851 S | 9/1997 | Wong |
| 5,681,712 A | 10/1997 | Nelson |
| 5,736,355 A | 4/1998 | Dyke |
| 5,750,184 A | 5/1998 | Imburgia |
| 5,770,393 A | 6/1998 | Dalmasso |
| 5,872,004 A | 2/1999 | Bolsen |
| 5,928,935 A | 7/1999 | Reuss, Jr. |
| 5,942,408 A | 8/1999 | Christensen |
| 5,955,296 A | 9/1999 | Roll |
| 5,968,807 A | 10/1999 | Kaiser |
| 6,025,189 A | 2/2000 | Bolea |
| D445,908 S | 7/2001 | Conway |
| 6,352,837 B1 | 3/2002 | Witcher |
| 6,436,659 B1 | 8/2002 | Hui et al. |
| 6,455,272 B1 | 9/2002 | Gillis |
| 6,556,508 B2 | 4/2003 | Tsao |
| 6,562,297 B1 | 5/2003 | Bonstein |
| 6,623,955 B2 | 9/2003 | Matner |
| 6,924,139 B2 | 8/2005 | Eveland |
| 7,141,387 B2 | 11/2006 | Ushiyama |
| 7,223,364 B1 | 5/2007 | Johnston |
| 7,416,883 B2 | 8/2008 | Cregger |
| 7,647,835 B2 | 1/2010 | Speldrich |
| 7,695,688 B2 | 4/2010 | Reed |
| D619,728 S | 7/2010 | Bare |
| D644,741 S | 9/2011 | Sattler |
| 2003/0133830 A1 | 7/2003 | Gonzalez |
| 2003/0235677 A1 | 12/2003 | Hanschen |
| 2005/0014214 A1 | 1/2005 | Eveland |
| 2005/0074833 A1 | 4/2005 | Gillis |
| 2006/0240504 A1 | 10/2006 | Gillis |
| 2006/0269983 A1 | 11/2006 | Cregger |
| 2007/0128589 A1 | 6/2007 | Sanders |
| 2008/0019866 A1 | 1/2008 | Paek |
| 2008/0070272 A1 | 3/2008 | Franciskovich |
| 2008/0261296 A1 | 10/2008 | Justi |
| 2008/0297864 A1 | 12/2008 | Horgan et al. |
| 2010/0075430 A1 | 3/2010 | Hofstadler |
| 2010/0081165 A1 | 4/2010 | Pasmore |
| 2012/0196355 A1 | 8/2012 | Franciskovich |
| 2013/0210048 A1 | 8/2013 | Chandrapati |
| 2013/0210067 A1 | 8/2013 | Chandrapati |
| 2013/0210069 A1 | 8/2013 | Pederson |
| 2013/0217107 A1 | 8/2013 | Pederson |
| 2013/0273593 A1 | 10/2013 | Foltz |
| 2013/0273594 A1 | 10/2013 | Ahimou |
| 2013/0302849 A1 | 11/2013 | Smith |

FOREIGN PATENT DOCUMENTS

| | | |
|---|---|---|
| EP | 0152298 | 8/1985 |
| EP | 347771 | 12/1989 |
| EP | 0610755 | 8/1994 |
| EP | 2256103 | 12/2010 |
| GB | 1547747 | 6/1979 |
| GB | 2186974 | 8/1987 |
| JP | H01-107765 | 4/1989 |
| JP | H08-511946 | 12/1996 |
| JP | 2002-516677 | 6/2002 |
| JP | 2004-329318 | 11/2004 |
| JP | 2006-518592 | 8/2006 |
| JP | 2007-175212 | 7/2007 |
| JP | 2008-523386 | 7/2008 |
| JP | 2009-092668 | 4/2009 |
| JP | WO 2010-045433 | 4/2010 |
| JP | 2010-107402 | 5/2010 |
| WO | WO 2001/13097 | 2/2001 |
| WO | WO 2002/08761 | 1/2002 |
| WO | WO 2004/000569 | 12/2003 |
| WO | WO 2004/027084 | 4/2004 |
| WO | WO 2005/042770 | 5/2005 |
| WO | WO 2007/009047 | 1/2007 |
| WO | WO 2007/070310 | 6/2007 |
| WO | WO 2010/045138 | 4/2010 |
| WO | WO 2010/045517 | 4/2010 |
| WO | WO 2010/128120 | 11/2010 |
| WO | WO 2011/011189 | 1/2011 |
| WO | WO 2012/012104 | 1/2012 |
| WO | WO 2012/012106 | 1/2012 |
| WO | WO 2012/061212 | 5/2012 |
| WO | WO 2012/061213 | 5/2012 |
| WO | WO 2012/061226 | 5/2012 |
| WO | WO 2012/061228 | 5/2012 |
| WO | WO 2012/061229 | 5/2012 |
| WO | WO 2012/158377 | 11/2012 |

OTHER PUBLICATIONS

Fundamental Knowledge of Chemical Analysis-Spectrophotometry, Analysis, 2008, vol. 4, pp. 158-162.
3M™ Attest™ 1292-S Biological Indicator for Steam 3M™ Attest™ Auto-Readers, Jan. 1, 2007, pp. 1-16.
M. Roth, Methods of Biochemical Analysis, vol. 17, D. Block, Ed., Interscience Publishers, New York, 1969, p. 89.
S. Undenfriend, Fluorescence Assay in Biology and Medicine, Academic Press, New York, 1962, p. 312.
D.J.R. Lawrence, Fluorescence Techniques for the Enzymologits, Method in Emzymology, vol. 4, S.P. Colowick and N.O. Kaplan, Eds., Academic Press, New York, 1957, p. 174.
International Search Report PCT/US2011/058257 dated Jun. 22, 2012, 5 pgs.
Chilvers et al., J. Appl. Microbiology, Synthesis and Evaluation of Novel Fluorogenic Substrates for the Detection of Bacterial β-galactosidase; 2001, 91, pp. 1118-1130.
Sernetz et al., "A new method for the evaluation of reaction kinetics of immobilized enzymes investigated in single enzyme-Sepharose beads by microfluorometry", Analytical Biochemistry, Academic Press, New York, vol. 72, No. 1-2, May 1976, pp. 24-37.
Vargas et al., "Preparation and quantification of 3'-phosphoadenosine 5'-phospho[<35>S] sulfate with high specific

(56) References Cited

OTHER PUBLICATIONS activity", Analytical Biochemistry, Academic Press, New York, vol. 172, No. 1, Jul. 1988, pp. 82-88.
Biosynth, Novel Chromogenic Enzyme Substrates, May 2009 Poster.
3M™ Attest™ 1292E Rapid Readout Biological Indicator, Internet Article, Jan. 1999, pp. 1-20.
Search Report; CN App. No. 201180052867.6; 3 pages; dated Jan. 2014.
Poster entitled "Novel Chromogenic Enzyme Substrates" by L.M. Wick et al.from Biosynth Chemistry & Biology; I-091/285; 2009; 1 pg.
EP Search Results Under Rule 164(2)(b) EPC—EP11788638; May 21, 2015; 3 pgs.

BIOLOGICAL STERILIZATION INDICATOR

CROSS-REFERENCE TO RELATED APPLICATIONS

This is a continuation of U.S. application Ser. No. 13/881,741, now U.S. Pat. No. 9,322,046, filed Apr. 26, 2013, which is a U.S. National Stage of PCT Application No. PCT/US2011/58257 under 35 USC § 371, filed Oct. 28, 2011, which claims the benefit of U.S. Provisional Application No. 61/408,966, filed Nov. 1, 2010 and 61/408,977, filed Nov. 1, 2010, the disclosures of which are incorporated herein by reference in their entirety.

FIELD

The present disclosure generally relates to sterilization indicators, and particularly, to biological sterilization indicators.

BACKGROUND

In a variety of industries, such as the health care industry but also in other industrial applications, it can be necessary to monitor the effectiveness of processes used to sterilize equipment such as medical devices, instruments and other disposable and non-disposable articles. In these settings, sterilization is generally defined as the process of completely destroying all viable sources of biological activity, such as microorganisms, including structures such as viruses and spores. As a standard practice, hospitals include a sterility indicator with a batch of articles to assay the lethality of the sterilization process. Both biological and chemical sterility indicators have been used.

One standard type of biological sterility indicator includes a known quantity of test microorganisms, for example *Geobacillus stearothermophilus* (formerly *Bacillus stearothermophilus*) or *Bacillus atrophaeus* (formerly *Bacillus subtilis*) spores, which can be many times more resistant to particular sterilization processes than other contaminating organisms. After the indicator is exposed to the sterilization process, the sources of biological activity (e.g., spores) can be incubated in a nutrient medium to determine whether any of the sources survived the sterilization process, with source metabolism and/or growth indicating that the sterilization process was insufficient to destroy all of the sources of biological activity.

Available chemical sterility indicators can be read immediately at the end of the sterilization process. However, the results indicate only that a particular condition was present during the sterilization process, such as the presence of a particular chemical or a temperature, and potentially, that the condition was reached for a certain period of time. On the contrary, the response of sources of biological activity to all conditions actually present can be a more direct and reliable test for how effective a sterilization process is in achieving sterilization.

SUMMARY

Some aspects of the present disclosure provide a biological sterilization indicator. The biological sterilization indicator can include a housing, and a container containing a liquid and being dimensioned to be positioned in the housing. At least a portion of the container can be frangible, and the container can have a first state in which the container is intact and the liquid is not in fluid communication with an interior of the housing and a second state in which the container is fractured and the liquid is in fluid communication with the interior of the housing. The biological sterilization indicator can further include a first chamber in the housing in which the container is positioned when the container is in the first state, and a second chamber in the housing in which the container and the liquid are not positioned when the container is in the first state. The second chamber can include a source of biological activity that is not in fluid communication with the liquid when the container is in the first state and that is in fluid communication with the liquid when the container is in the second state. The biological sterilization indicator can further include a substrate positioned in the housing between the first chamber and the second chamber. The substrate can be positioned in fluid communication with the first chamber and the second chamber, and the substrate can be further positioned such that the substrate is not in direct contact with the source of biological activity.

Other features and aspects of the present disclosure will become apparent by consideration of the detailed description and accompanying drawings.

DETAILED DESCRIPTION

Figure 1:
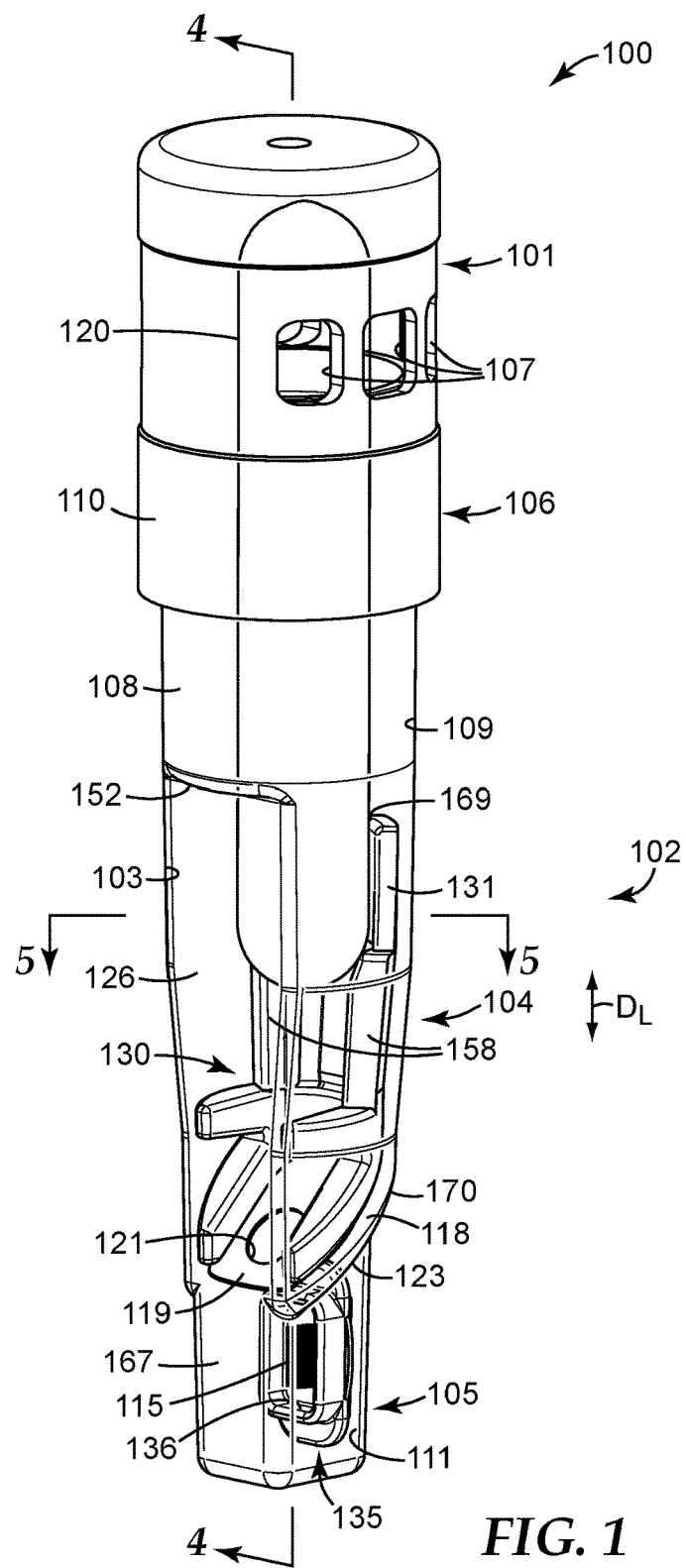
FIG. 1 is a front perspective view of a biological sterilization indicator according to one embodiment of the present disclosure, the biological sterilization indicator including a housing that includes a first portion and a second portion.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports, and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a sterilization indicator, and particularly, to a biological sterilization indicator. A biological sterilization indicator is also sometimes referred to as a "biological sterility indicator," or simply, a "biological indicator." Some embodiments of the biological sterilization indicator of the present disclosure are self-contained, and can be used to determine the lethality of a sterilizing process. The present disclosure generally relates to the construction of the biological sterilization indicator that allows for one or more of at least the following: housing a liquid (e.g., an aqueous mixture) separate from one or more sources of biological activity during sterilization and allowing for combination of the liquid and the sources of biological activity after sterilization; facilitating sterilant movement to a location (e.g., a closed end) of the biological sterilization indicator where one or more sources of biological activity are housed; holding a frangible container (e.g., an ampoule, such as a glass ampoule) that contains the liquid in a location separate from the source(s) of biological activity in the biological sterilization indicator during sterilization; releasing the liquid from the frangible container during activation of the biological sterilization indicator (e.g., by fracturing the container); controlling and/or facilitating the movement of the liquid during activation to a location in the biological sterilization indicator where the source(s) of biological activity are housed; providing a substantially constant sterilant path; collecting and/or retaining portions of the fractured container (e.g., to inhibit movement of the fractured portions to the proximity of the sources of biological activity); minimizing diffusion of source(s) of biological activity and/or signals or detectable products away from the source location or a detection region of the biological sterilization indicator (e.g., to enhance detection); and generally controlling and/or facilitating fluid flow within the biological sterilization indicator (e.g., by employing a substrate and one or more internal vents).

Pressurized steam or other common sterilants can be used to sterilize equipment and supplies used in healthcare environments. Small, self-contained indicators, such as biological sterilization indicators, can be used to verify the efficacy of the sterilization processes. These indicators can be biological and can contain sources of biological activity.

Nutrient medium used to nourish the sources of biological activity (e.g., spores) following a sterilization procedure can be present throughout the sterilization procedure but may not be accessible by the sources of biological activity until desired. For example, a frangible pouch or container (e.g., an ampoule, such as a glass ampoule) can house the medium 'on board' separately from the sources of biological activity, and the container can be fractured to put the sources of biological activity and medium in fluid communication with one another, when desired (e.g., after a sterilization process).

Nutrients and nutrient media to facilitate the growth of microorganisms are known in the art and can be found, for example, in the "Handbook of Microbiological Media" by Ronald Atlas, published by CRC Press, Boca Raton, Fla. Matner et al. (U.S. Pat. No. 5,073,488), which is incorporated herein by reference in its entirety, describes a nutrient medium for the growth and detection of bacterial spores in a biological sterilization indicator that can be employed in biological sterilization indicators of the present disclosure.

Generally, sources of biological activity (e.g., microorganisms) are chosen to be used in a biological sterilization indicator that are resistant to a particular sterilization process. The biological sterilization indicators of the present disclosure include a viable quantity, or culture, of one or more known sources of biological activity (e.g., species of microorganism). Such sources of biological activity can be in the form of microbial spores. The test source in the biological sterilization indicator is either killed by a successful sterilization cycle, or survives if the sterilization cycle is not adequate for some reason. Bacterial spores, rather than the vegetative form of the organisms, are sometimes used at least partly because vegetative bacteria are known to be relatively easily killed by sterilizing processes. Spores can also have superior storage characteristics and can remain in their dormant state for years. As a result, in some embodiments, sterilization of an inoculum of a standardized spore strain can provide a high degree of confidence that inactivation of all microorganisms in a sterilizing chamber has occurred.

By way of example only, the present disclosure describes the one or more sources of biological activity used in the biological sterilization indicator as being "spores;" however, it should be understood that the type of source (e.g., spore) used in a particular embodiment of the biological sterilization indicator is selected for being highly resistant to the particular sterilization process contemplated. Accordingly, different embodiments of the present disclosure may use different sources of biological activity, depending on the sterilization process for which the particular embodiment is intended. The term "spores" is used throughout the present disclosure for simplicity, but it should be understood that other sources of biological activity, such as microorganisms (e.g., bacteria, fungi, viruses, etc.), spores (e.g., bacterial, fungal, etc.), enzymes, substrates for enzymatic activity, ATP, microbial metabolites, or a combination thereof, can be used in the biological sterilization indicator of the present disclosure instead.

The phrase "biological activity" generally refers to any specific catalytic process or groups of processes associated with a biological cell. Nonlimiting examples of biological activities include catabolic enzyme activities (e.g., carbohydrate fermentation pathways), anabolic enzyme activities (e.g., nucleic acid, amino acid, or protein synthesis), coupled reactions (e.g., a metabolic pathway), biomolecule-mediated redox reactions (e.g., electron transport systems), and bioluminescent reactions. "Predetermined" biological activity means that the method is directed toward the detection of a specific biological process (e.g., an enzyme reaction) or group of biological processes (e.g., a biochemical pathway). It will be appreciated by a person having ordinary skill in the art that certain predetermined biological activities may be associated with a particular type of cell (e.g., cancer cell or microorganism) or a pathological process.

Similarly, it should be understood that phrases used in the present disclosure that include the term "spore," such as "spore carrier," "spore reservoir," "spore region," "spore growth chamber," and the like, are used merely for simplicity, but that such components, elements or phrases equally apply to other sources of biological activity and are not intended to refer only to spores. For example, the above phrases can also be referred to as a "source carrier," a "source region," a "source reservoir," a "source growth chamber," and the like.

The process of bringing the spores and medium together can be referred to as "activation" of the biological sterilization indicator. That is, the term "activation" and variations thereof, when used with respect to a biological sterilization indicator, can generally refer to bringing one or more sources of biological activity (e.g., spores) in fluid communication with a liquid or medium (e.g., a nutrient medium for the spores of interest). For example, when a frangible container within the biological sterilization indicator that contains the medium is at least partially fractured, punctured, pierced, crushed, cracked, or the like, such that the medium has been put in fluid communication with the source(s) of biological activity, the biological sterilization indicator can be described as having been "activated." Said another way, a biological sterilization indicator has been activated when the source(s) of biological activity have been exposed to the medium which was previously housed separately from the source(s) of biological activity.

Some existing sterilization indicators, and particularly, biological sterilization indicators, include a housing that defines a single chamber therein, and into which various components are positioned, such as a source carrier (e.g., a spore strip) that is adapted for locating the source(s) of biological activity in a desired location (e.g., a closed end) in the biological sterilization indicator, and a container comprising a liquid (e.g., a nutrient medium). The present disclosure, however, is generally directed to biological sterilization indicators having more than one chamber formed within a housing, such that the container and the source(s) of biological activity can be housed separately from one another and in separate regions of the biological sterilization indicator, particularly during sterilization. While the biological sterilization indicators of the present disclosure may include more than one chamber and provide for separating the container and the source(s) of biological activity, the biological sterilization indicators of the present disclosure have been designed so that such a separation between components may not adversely affect other functions of the biological sterilization indicator. For example, biological sterilization indicators of the present disclosure can also facilitate (1) moving a sterilant to the source(s) of biological activity during sterilization, and/or (2) moving the liquid into contact with the source(s) of biological activity when desired (e.g., after sterilization and during activation of the biological sterilization indicator).

In some embodiments, the facilitated fluid flow through and/or within the biological sterilization indicator can be provided by employing one or more internal vents or vent channels. Such internal vents can be provided by fluid paths that are formed within the biological sterilization indicator. The phrases "vent," "internal vent," "vent channel," or variations thereof can generally refer to a fluid path that is positioned to allow gas present in one region (e.g., chamber, reservoir, volume, portion, etc.) of the biological sterilization indicator to be displaced when another fluid (e.g., a liquid, a gas or combinations thereof) is moved into that region. Particularly, such phrases generally refer to internal fluid paths that allow one region within the biological sterilization indicator to be vented to another region within the biological sterilization indicator (e.g., when the biological sterilization indicator is sealed from ambience) to facilitate fluid movement into a desired region of the biological sterilization indicator. Furthermore, such venting within the biological sterilization indicator can facilitate moving fluid from a larger region to a smaller region (e.g., a closed end) of the biological sterilization indicator, particularly when the volume of fluid to be moved is greater than the volume of the smaller region. In some embodiments, such internal venting can facilitate fluid flow within or throughout the biological sterilization indicator even without employing substantial, or any, external force, such as centrifugation, shaking, tapping, or the like.

In some embodiments, the biological sterilization indicators of the present disclosure can include a first fluid path positioned to fluidly couple a first chamber and a second chamber, and a second fluid path positioned to fluidly couple the second chamber with another chamber (e.g., the first chamber) within the biological sterilization indicator. The first fluid path can generally be used for moving a sterilant (i.e., during sterilization) and/or the liquid (i.e., during activation) from the first chamber to the second chamber, and the second fluid path can generally be used as a vent for the second chamber to allow gas to escape the second chamber and to facilitate moving the sterilant and/or the liquid into the second chamber. In such embodiments, the first chamber can be used to house the container that contains the liquid, and the second chamber can be used to house one or more sources of biological activity.

After a biological sterilization indicator has been exposed to a sterilization cycle, the sterilization load (e.g., including the items desired to be sterilized and the biological sterilization indicator) can be removed from the sterilizer. One of the first steps in processing the biological sterilization indicator can include activating the biological sterilization indicator. In some embodiments, activation can include closing the biological sterilization indicator, which can include moving a portion (e.g., a cap) of the biological sterilization indicator relative to another portion of the biological sterilization indicator (e.g., a tube, a base, a tubular body, etc.). In some embodiments, the interior of the biological sterilization indicator can remain in fluid communication with ambience during sterilization, but closed off from ambience after sterilization. For example, in some embodiments, the cap of the biological sterilization indicator can be coupled to the tube of the biological sterilization indicator during sterilization in a first position that maintains fluid communication between the interior of the biological sterilization indicator and ambience. After sterilization, the cap can be pressed further onto the tube (e.g., to a second position in which the interior of the biological sterilization indicator is no longer in fluid communication with ambience) to maintain sterility and reduce the evaporation rate of a medium (e.g., a liquid) used to support the metabolic activity and/or growth of the spores (i.e., if still viable). The medium can be contained during sterilization and released into the interior of the biological sterilization indicator after sterilization. For example, the medium can be separately housed from the spores during sterilization in a frangible container that can be at least partially fractured after sterilization during an activation step (e.g., in response to moving the cap relative to the tube or base of the biological sterilization indicator) to bring the medium into fluid communication with the spores to ensure proper nutrition of the spores.

In some embodiments of the present disclosure, closing the biological sterilization indicator (e.g., moving a portion relative to another portion to seal the interior) can include or cause fracturing of a frangible container containing the medium, such that closing the biological sterilization indicator causes activation of the biological sterilization indicator.

The biological sterilization indicator of the present disclosure can be used with a variety of sterilization processes including, but not limited to, exposure to steam (e.g., pressurized steam), dry heat, gaseous or liquid agents (e.g., ethylene oxide, hydrogen peroxide, peracetic acid, ozone, or combinations thereof), radiation, or combinations thereof. In at least some of the sterilization processes, an elevated temperature, for example, 50° C., 100° C., 121° C., 132° C., 134° C., or the like, is included or may be encountered in the process. In addition, elevated pressures and/or a vacuum may be encountered, for example, 15 psi ($1 \times 10^5$ Pa)

As mentioned above, the sources of biological activity used in a particular system are selected according to the sterilization process used. For example, for a steam sterilization process, *Geobacillus stearothermophilus* or *Bacillus stearothermophilus*, or spores thereof, can be used. In another example, for an ethylene oxide sterilization process, *Bacillus atrophaeus* (formerly *Bacillus subtilis*), or spores thereof, can be used. In some embodiments, sterilization process resistant spores can include, but are not limited to, at least one of *Geobacillus stearothermophilus, Bacillus stearothermophilus, Bacillus subtilis, Bacillus atrophaeus, Bacillus megaterium, Bacillus coagulans, Clostridium sporogenes, Bacillus pumilus*, or combinations thereof.

Enzymes and substrates that can be suitable for use in the biological sterilization indicator of the present disclosure are identified in U.S. Pat. No. 5,073,488 (Matner et al), U.S. Pat. No. 5,418,167 (Matner et al.), and U.S. Pat. No. 5,223,401 (Foltz et al.), which are incorporated herein by reference for all they disclose.

Suitable enzymes can include hydrolytic enzymes and/or enzymes derived from spore-forming microorganisms, such as *Bacillus stearothermophilus* and *Bacillus subtilis*. Enzymes from spore-forming microorganisms that can be useful in the biological sterilization indicators of the present disclosure can include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase and fatty acid esterases.

Some embodiments of the biological sterilization indicator can include chromogenic and/or fluorogenic substrates that react with enzymes to form detectable products (M. Roth, *Methods of Biochemical Analysis*, Vol. 17, D. Block, Ed., Interscience Publishers, New York, 1969, p. 89, incorporated herein by reference; S. Udenfriend, *Fluorescence Assay in Biology and Medicine*, Academic Press, New York, 1962, p. 312; and D. J. R. Lawrence, *Fluorescence Techniques for the Enzymologist*, Methods in Enzymology, Vol. 4, S. P. Colowick and N. O. Kaplan, Eds., Academic Press, New York, 1957, p. 174). These substrates may be classified in two groups based on the manner in which they create a visually detectable signal or product. The substrates in the first group react with enzymes to form enzyme-modified products that are themselves chromogenic or fluorescent. Substrates in the second group form enzyme-modified products that must react further with an additional compound, or compounds, to create a detectable product that can generate a color or fluorescent signal.

As a result, the phrase "detectable product" can refer to any molecule, compound, substance, substrate, or the like, or combinations thereof, that can be detected by any of the detection methods or processes described below. For example, such detectable products can be a sign of the viability of a source of biological activity, and detection of such products can generally indicate the failure or inadequacy of a sterilization process.

In some embodiments, the source of active enzyme can be (1) the purified, isolated enzyme derived from an appropriate microorganism; (2) a microorganism to which the enzyme is indigenous or added by genetic engineering; and/or (3) a microorganism to which the enzyme has been added during sporulation or growth, such that the enzyme is incorporated or associated with the microorganism, e.g., an enzyme added to a spore during sporulation which becomes incorporated within the spore. In some embodiments, the microorganisms which may be utilized as the source of an enzyme include bacteria or fungi in either the spore or vegetative state. In some embodiments, the enzyme source includes *Bacillus, Clostridium, Neurospora, Candida*, or a combination of such species of microorganisms.

The enzyme alpha-D-glucosidase has been identified in spores of *Bacillus stearothermophilus*, such as those commercially available as "ATCC 8005" and "ATCC 7953" from American Type Culture Collection, Rockville, Md. The enzyme beta-D-glucosidase has been found in *B. subtilis* (e.g., commercially available as "ATCC 9372" from American Type Culture Collection).

In the event that an isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. In such a case, the method of the present disclosure may include the step of incubating any viable microorganism remaining after the sterilization cycle with an aqueous nutrient medium to confirm the sterilization efficacy.

In general, monitoring the effectiveness of the sterilization process can include placing the biological sterilization indicator of the present disclosure in a sterilizer. In some embodiments, the sterilizer includes a sterilization chamber that can be sized to accommodate a plurality of articles to be sterilized, and can be equipped with a means of evacuating air and/or other gases from the chamber and a means for adding a sterilant to the chamber. The biological sterilization indicator of the present disclosure can be positioned in areas of the sterilizer that are most difficult to sterilize (e.g., above the drain). Alternately, the biological sterilization indicator of the present disclosure can be positioned adjacent (or in the general proximity of) an article to be sterilized when the biological sterilization indicator is positioned in the sterilization chamber. In addition, the biological sterilization indicator can be positioned in process challenge devices that can be used in sterilizers.

The sterilization process can further include exposing the article(s) to be sterilized and the biological sterilization indicator to a sterilant. In some embodiments, the sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological sterilization indicator.

In general, after the biological sterilization indicator has been exposed to a sterilization cycle, a liquid (e.g., a growth media, water that can be mixed with a solid growth media, etc., or combinations thereof) can be introduced to the spores. As mentioned above, the step in which the liquid is introduced to the spores can be referred to the "activation step." If the spores have survived the sterilization cycle, the liquid will facilitate metabolic activity and/or growth of the spores, and such activity and/or growth can be investigated. If growth is observed, the sterilization cycle is generally deemed ineffective.

FIGS. 1-7 illustrate the biological sterilization indicator 100 according to one embodiment of the present disclosure. Other suitable embodiments of biological sterilization indicators are described in PCT Publication No. WO2011/011189, entitled "Biological Sterilization Indicator and Method of Using Same"; U.S. Publication No. 2013/0217107, entitled "Biological Sterilization Indicator System and Method"; U.S. Pat. No. 9,145,573, entitled "Biological Sterilization Indicator System and Method"; and U.S. Pat. No. 8,840,837, entitled "Biological Sterilization Indicator and Method of Using Same"; each of which is incorporated herein by reference in its entirety.

The biological sterilization indicator 100 can include a housing 102, which can include a first portion 104 and a second portion 106 (e.g., a cap) adapted to be coupled together to provide a self-contained biological sterilization indicator. In some embodiments, the first portion 104 and second portion 106 can be formed of the same materials, and in some embodiments, the first portion 104 and the second portion 106 can be formed of different materials. The housing 102 can define a reservoir 103 of the biological sterilization indicator 100 in which other components can be positioned and into which a sterilant can be directed during a sterilization process.

The housing 102 can be defined by at least one liquid impermeable wall, such as a wall 108 of the first portion 104 and/or a wall 110 of the second portion 106. It should be understood that a one-part unitary housing 102 may also be employed or that the first and second portions 104 and 106 can take on other shapes, dimensions, or relative structures without departing from the spirit and scope of the present disclosure. Suitable materials for the housing 102 (e.g., the walls 108 and 110) can include, but are not limited to, a glass, a metal (e.g., foil), a polymer (e.g., polycarbonate (PC), polypropylene (PP), polyphenylene (PPE), polythyene, polystyrene (PS), polyester (e.g., polyethylene terephthalate (PET)), polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

In some embodiments, the biological sterilization indicator 100 can further include a frangible container 120 that contains a liquid (e.g., an aqueous mixture) 122, and which is dimensioned to be received within the biological sterilization indicator 100, for example, within at least a portion of the housing 102 (e.g., at least within the first portion 104 of the housing 102). The frangible container 120 can be formed of a variety of materials, including, but not limited to, one or more of metal (e.g., foil), a polymer (e.g., any of the polymers listed above with respect to the housing 102), glass (e.g., a glass ampoule), and combinations thereof. In some embodiments, only a portion of the container 120 is frangible, for example, the container 120 can include a frangible portion or cover (e.g., a frangible barrier, film, membrane, or the like). The frangible container 120 can have a first state in which it is intact and the liquid 122 is contained therein, and a second state in which at least a portion of the container 120 is fractured. In the second state of the container 120, the liquid 122 can be in fluid communication with the reservoir 103 of the biological sterilization indicator 100, e.g., when the container 120 is positioned in the biological sterilization indicator 100.

As shown in the illustrated embodiment, the container 120 can be held in place within the biological sterilization indicator 100 and/or fractured by an insert 130, which is described in greater detail below.

Figure 2:
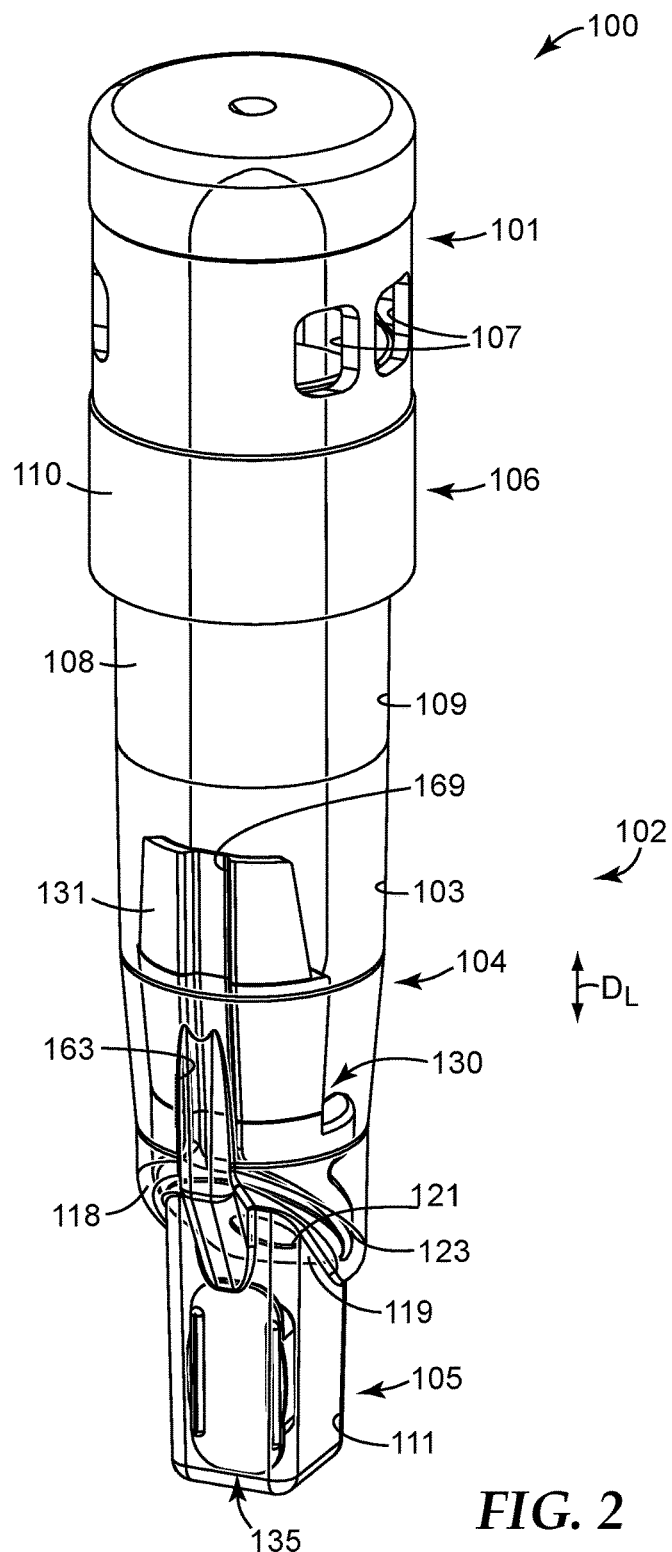
FIG. 2 is a rear perspective view of the biological sterilization indicator of FIG. 1.
Figure 3:
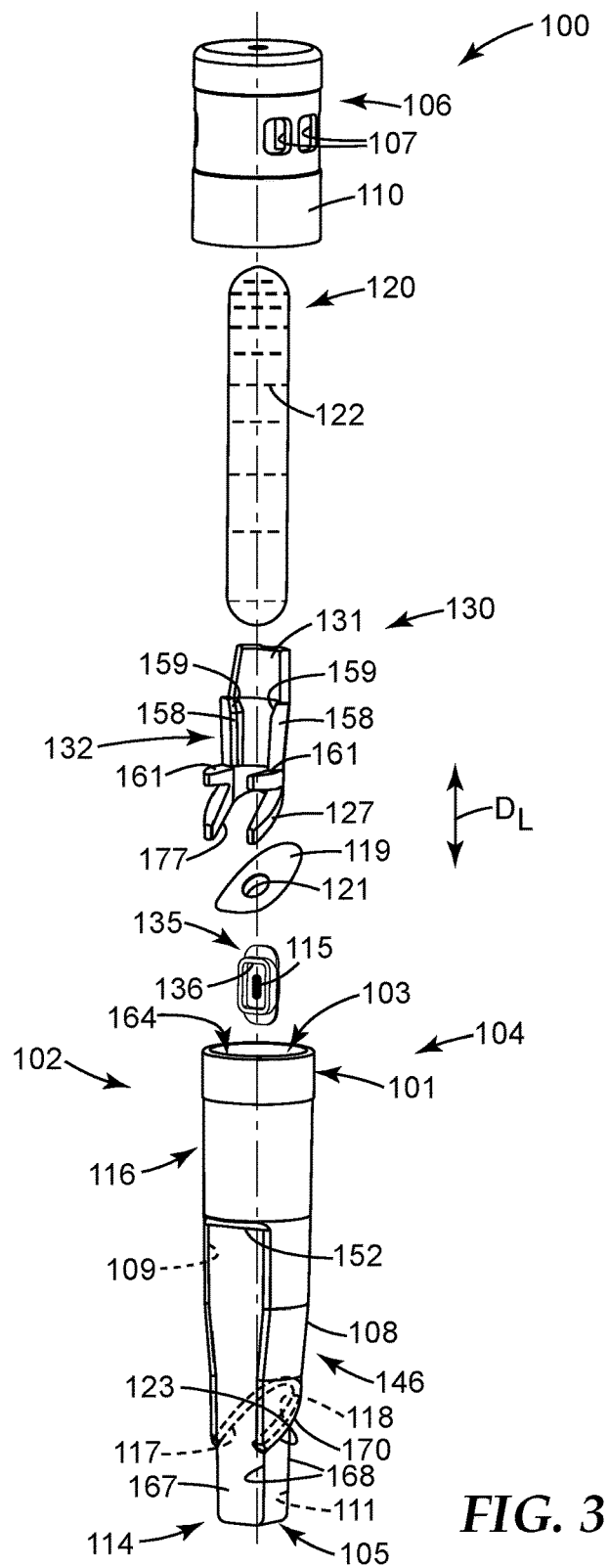
FIG. 3 is a front exploded view of the biological sterilization indicator of FIGS. 1-2.

The first portion 104 of the housing 102 can be adapted to house a majority of the components of the biological sterilization indicator 100, and can be referred to as a "tube," "tubular body," "base," or the like. The housing 102 can include a reservoir 103 that can be defined by one or both of the first portion 104 and the second portion 106 of the housing 102. The biological sterilization indicator 100 can further include spores or another source(s) of biological activity 115 (or a locus of spores) positioned in fluid communication with the reservoir 103. As shown in FIGS. 1-3, the second portion 106 of the housing 102 can include one or more apertures 107 to provide fluid communication between the interior of the housing 102 (e.g., the reservoir 103) and ambience. For example, the one or more apertures 107 can provide fluid communication between the spores 115 and ambience during a sterilization process, and can serve as an inlet into the biological sterilization indicator 100 and as an inlet of a sterilant path 164 (described in greater detail below). In some embodiments, the second portion 106 of the housing 102 can be coupled to a first (e.g., open) end 101 of the first portion 104 of the housing 102, and the spores 115 can be positioned at a second (e.g., closed) end 105, opposite the first end 101, of the first portion 104 of the housing 102.

In some embodiments, a barrier or filter (e.g., a sterile barrier; not shown) can be positioned in the sterilant path 164 (e.g., at the inlet formed by the aperture 107) to inhibit contaminating or foreign organisms, objects or materials from entering the biological sterilization indicator 100. Such a barrier can include a gas-transmissive, microorganism-impermeable material, and can be coupled to the housing 102 by a variety of coupling means, including, but not limited to, an adhesive, a heat seal, sonic welding, or the like. Alternatively, the barrier can be coupled to the sterilant path 164 via a support structure (such as the second portion 106) that is coupled to the first portion 104 of the housing 102 (e.g., in a snap-fit engagement, a screw-fit engagement, a press-fit engagement, or a combination thereof). During exposure to a sterilant, the sterilant can pass through the barrier into the sterilant path 164 and into contact with the spores 115.

In some embodiments, as shown in the illustrated embodiment, the housing 102 can include a lower portion 114 and an upper portion 116, which can be at least partially separated by an inner wall (or partial wall) 118, ledge, partition, flange, or the like, in which can be formed an opening 117 that provides fluid communication between the lower portion 114 and the upper portion 116. In some embodiments, the lower portion 114 of the first portion 104 of the housing 102 (sometimes referred to as simply "the lower portion 114" or the "the lower portion 114 of the housing 102") can be adapted to house the spores 115 or a locus of spores. In some embodiments, the lower portion 114 can be referred to as the "detection portion" or "detection region" of the housing 102, because at least a portion of the lower portion 114 can be interrogated for signs of spore growth. In addition, in some embodiments, the upper portion 116 of the first portion 104 of the housing 102 (sometimes referred to as "the upper portion 116" or the "the upper portion 116 of the housing 102" for simplicity) can be adapted to house at least a portion of the frangible container 120, particularly before activation.

In some embodiments, the portion of the reservoir 103 that is defined at least partially by the upper portion 116 of the housing 102 can be referred to as a first chamber (or reservoir, zone, region, or volume) 109 and the portion of the reservoir 103 that is defined at least partially by the lower portion 114 of the housing 102 can be referred to as a second chamber (or reservoir, zone, region, or volume) 111. In some embodiments, the second chamber 111 can be referred to as a "spore growth chamber" or a "detection chamber," and can include a volume to be interrogated for spore viability to determine the efficacy of a sterilization process.

The first chamber 109 and the second chamber 111 can be positioned in fluid communication with each other to allow a sterilant and the liquid 122 to move from (i.e., through) the first chamber 109 to the second chamber 111. In some embodiments, the degree of fluid connection between the first chamber 109 and the second chamber 111 (e.g., the size of an opening, such as the opening 117, connecting the first chamber 109 and the second chamber 111) can increase after, simultaneously with, and/or in response to the activation step (i.e., the liquid 122 being released from the container 120). In some embodiments, the control of fluid communication (or extent of fluid connection) between the first chamber 109 (e.g., in the upper portion 116) and the second chamber 111 (e.g., in the lower portion 114) can be provided by at least a portion of the insert 130.

The container 120 can be positioned and held in the first chamber 109 during sterilization and when the container 120 is in a first, unfractured, state. The spores 115 can be housed in the second chamber 111 and in fluid communication with ambience when the container 120 is in the first state. The first chamber 109 and the second chamber 111 can be configured such that the container 120 is not present in the second chamber 111, and particularly, not when the container 120 is in its first, unfractured, state. A sterilant can move into the second chamber 111 (e.g., via the first chamber 109) during sterilization, and the liquid 122 can move into the second chamber 111 (e.g., from the first chamber 109) during activation, when the container 120 is fractured and the liquid 122 is released into the interior of the housing 102.

As a result, when the container 120 is in the first state, the first chamber 109 and the second chamber 111 can be in fluid communication with one another, and with ambience (e.g., during sterilization). For example, the first chamber 109 and the second chamber 111 can be in fluid communication with ambience via the one or more apertures 107. In some embodiments, the first chamber 109 and the second chamber 111 can be in fluid communication with ambience in such a way that the first chamber 109 is positioned upstream of the second chamber 111 when a sterilant is entering the biological sterilization indicator 100. That is, the first chamber 109 can be positioned between the sterilant inlet (e.g., the one or more apertures 107) and the second chamber 111, and the sterilant inlet can be positioned on an opposite side of the first chamber 109 than the second chamber 111.

Figure 4:
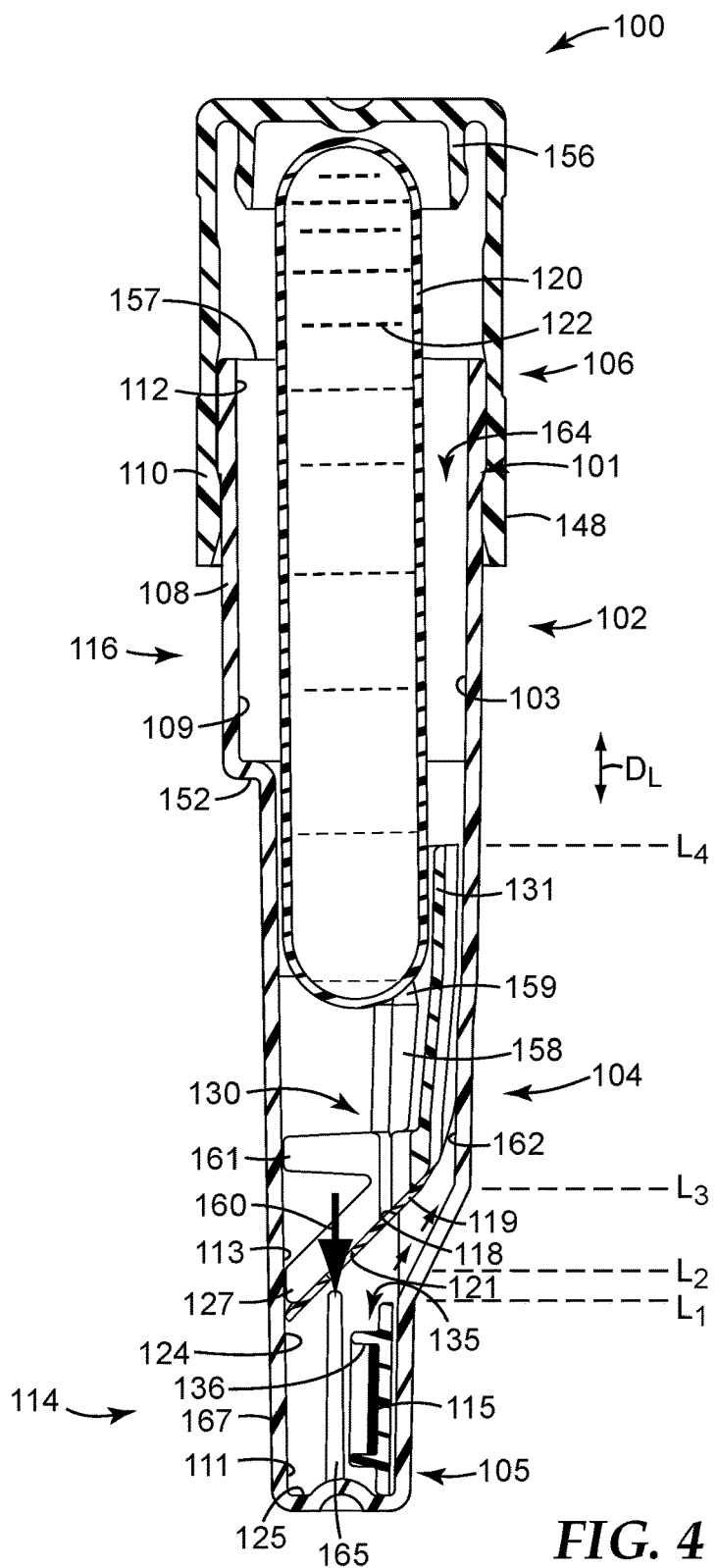
FIG. 4 is a side cross-sectional view of the biological sterilization indicator of FIGS. 1-3, taken along line 4-4 of FIG. 1, the biological sterilization indicator shown in a first state, and the second portion of the housing of the biological sterilization indicator shown in a first position.
Figure 5:
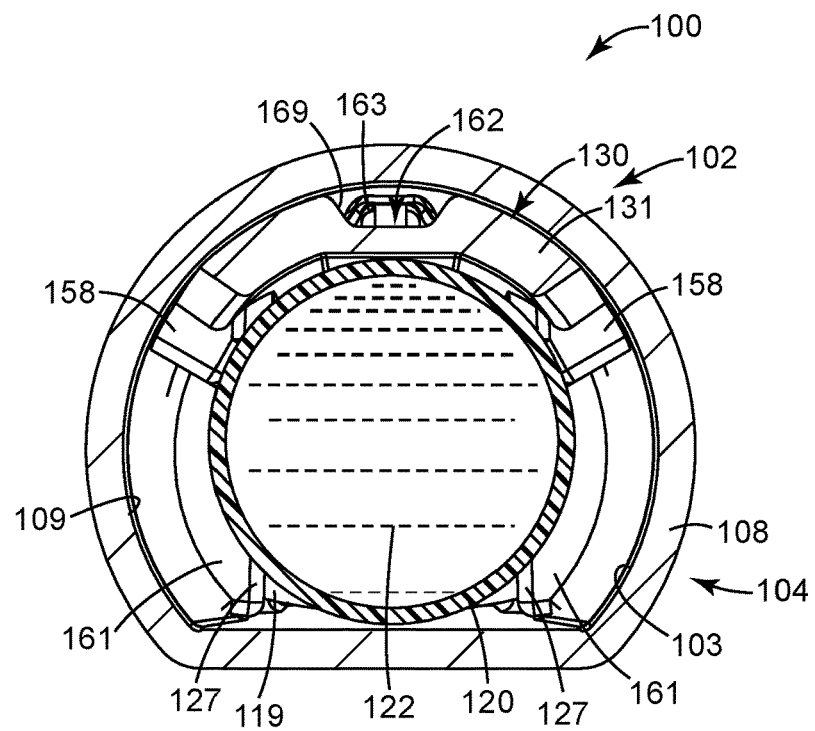
FIG. 5 is a top cross-sectional view of the biological sterilization indicator of FIGS. 1-4, taken along line 5-5 of FIG. 1.
Figure 6:
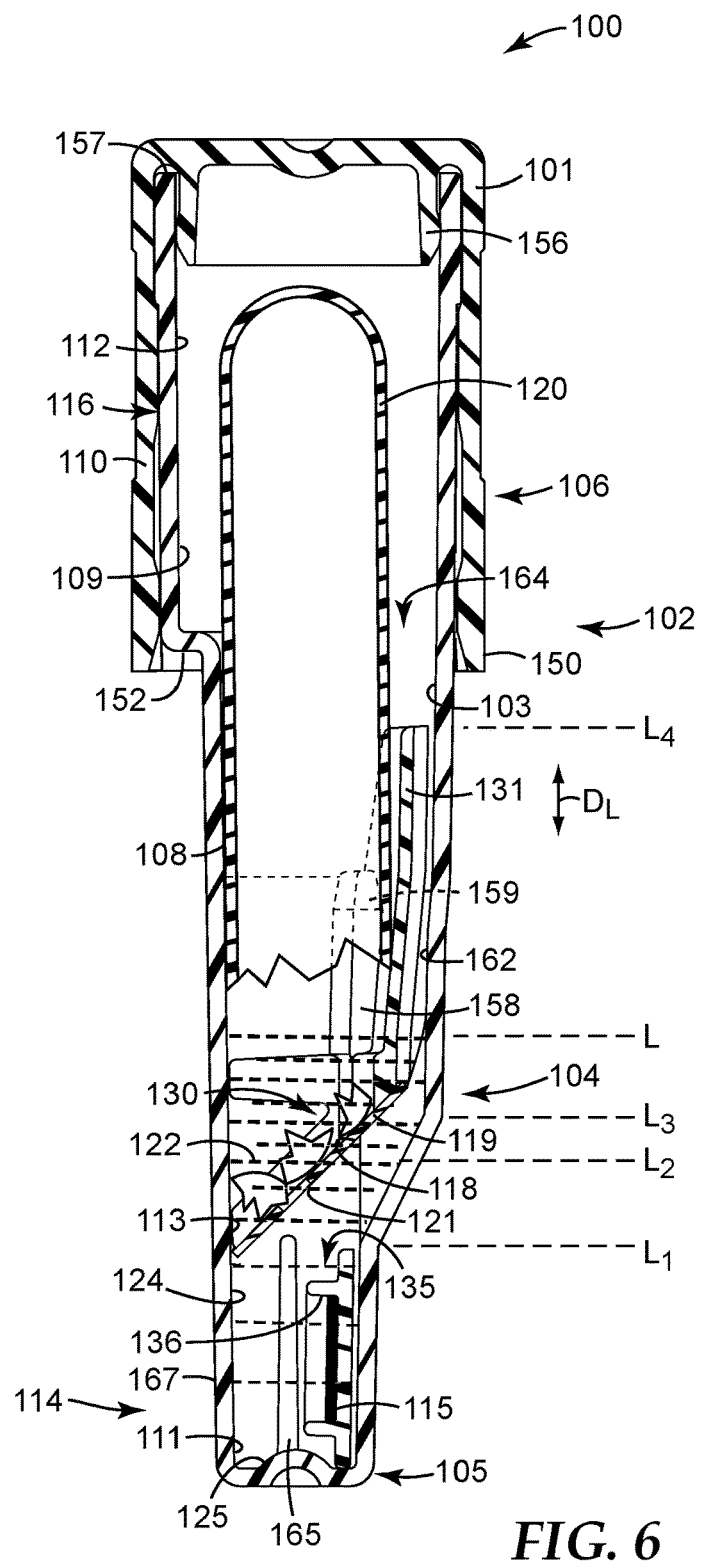
FIG. 6 is a side cross-sectional view of the biological sterilization indicator of FIGS. 1-5, the biological sterilization indicator shown in a second state, and the second portion of the housing of the biological sterilization indicator shown in a second position.

As shown in FIGS. 4 and 6, in some embodiments, the first chamber 109 can be defined by one or both of the first portion 104 and the second portion 106, particularly when the container 120 is in the first state. In addition, in some embodiments, the first chamber 109 can include a first end 112 positioned adjacent the open end 101 of the first portion 104 of the housing 102, adjacent the second portion 106 of the housing 102, and/or at least partially defined by the second portion 106. The first chamber 109 can further include a second end 13 positioned adjacent and in fluid communication with the second chamber 111 and positioned toward the closed end 105 of the housing 102. The first end 112 of the first chamber 109 can be at defined by the first portion 104 and/or the second portion 106 of the housing 102.

As further shown in FIGS. 4 and 6, in some embodiments, the second chamber 111 can include a first end 124 positioned adjacent and in fluid communication with the first chamber 109 and positioned toward the open end 101 of the housing 102, and a second end 125 at least partially defined by, including, or positioned adjacent the closed end 105 of the housing 102.

Said another way, as shown in FIGS. 4 and 6, the biological sterilization indicator 100 can include a longitudinal direction $D_L$, and in some embodiments, the first chamber 109 can be positioned longitudinally above the second chamber 111.

In some embodiments, the second chamber 111 can be at least partially defined by, can include, or can be positioned adjacent the closed end 105 of the biological sterilization indicator 100. In addition, in some embodiments, the second chamber 111 can be smaller (e.g., in volume and/or cross-sectional area) than at least one of the first chamber 109 and the volume of the liquid 122 in the container 120 that will be released when the biological sterilization indicator 100 is activated. As a result, in such embodiments, the second chamber 111 can exhibit an air-lock effect where gas (e.g. air) that is present in the second chamber 111 can inhibit fluid movement into the second chamber 111. In some embodiments, as described in greater detail below, a fluid path that allows the second chamber 111 to vent to another portion of the biological sterilization indicator 100 can facilitate fluid movement into the second chamber 111.

In some embodiments, the wall 118 (sometimes referred to as a "separating wall") can be angled or slanted, for example, oriented at a non-zero and non-right angle with respect to the longitudinal direction $D_L$ of the housing 102 (e.g., where the longitudinal direction $D_L$ extends along the length of the housing 102). Such angling or slanting of the wall 118 can facilitate the movement of the liquid 122 from the upper portion 116 to the lower portion 114 after sterilization and after the container 120 has been broken to release the liquid 122.

As shown in FIGS. 1-3, in some embodiments, the wall 118 can be at least partially formed by a change in the inner dimension of the housing 102. For example, as shown, the wall 118 can be formed by a decrease in a cross-sectional area from a first longitudinal position in the first chamber 109 to a second longitudinal position in the second chamber 111. In addition, by way of example only, the internal cross-sectional shape of the housing 102 can change at the transition from the first chamber 109 to the second chamber 111 from being substantially round (e.g., with one flat side that makes up less than 50% of the perimeter) in the first chamber 109 to substantially parallelepipedal (e.g., substantially square) in the second chamber 111.

Furthermore, in some embodiments, the wall 118 can also be at least partially formed by a change in the outer dimension of the housing 102. As shown in FIGS. 1-3, in some embodiments, the housing 102 includes a step (or ledge, overhang, transition, or the like) 123 that is angled consistently with the wall 118 (if the wall 118 is angled), and which includes a change in the outer shape and dimension of the housing 102. However, it should be understood that in some embodiments, even if the inner dimension of the housing 102 changes to create a second chamber 111 that has a different cross-sectional shape or dimension than the first chamber 109, the outer shape and dimension of the housing 102 need not change, or change consistently with the change in the inner shape and/or dimension. For example, in some embodiments, the step 123 can be oriented substantially perpendicularly with respect to the longitudinal direction $D_L$.

In some embodiments, the reservoir 103 has a volume of at least about 0.5 milliliters (mL), in some embodiments, at least about 1 mL, and in some embodiments, at least about 1.5 mL. In some embodiments, the reservoir 103 has a volume of no greater than about 5 mL, in some embodiments, no greater than about 3 mL, and in some embodiments, no greater than about 2 mL.

In some embodiments, the frangible container 120 has a volume of at least about 0.25 mL, in some embodiments, at least about 0.5 mL, and in some embodiments, at least about 1 mL. In some embodiments, the frangible container 120 has a volume of no greater than about 5 mL, in some embodiments, no greater than about 3 mL, and in some embodiments, no greater than about 2 mL.

In some embodiments, the volume of the liquid 122 contained in the frangible container 120 is at least about 50 microliters, in some embodiments, at least about 75 microliters, and in some embodiments, at least about 100 microliters. In some embodiments, the volume of the liquid 122 contained in the frangible container 120 is no greater than about 5 mL, in some embodiments, no greater than about 3 mL, and in some embodiments, no greater than about 2 mL.

In some embodiments, the first chamber 109 (i.e., formed by the upper portion 116 of the first portion 104 of the housing 102) has a volume of at least about 500 microliters (or cubic millimeters), in some embodiments, at least about 1000 microliters, in some embodiments, at least about 2000 microliters, and in some embodiments, at least about 2500 microliters. In some embodiments, the first chamber 109 has a volume of no greater than about 5000 microliters, in some embodiments, no greater than about 4000 microliters, and in some embodiments, no greater than about 3000 microliters. In some embodiments, the first chamber 109 has a volume of about 2790 microliters, or 2800 microliters.

In some embodiments, the second chamber 111 (i.e., formed by the lower portion 114 of the first portion 104 of the housing 102) has a volume of at least about 5 microliters, in some embodiments, at least about 20 microliters, and in some embodiments, at least about 35 microliters. In some embodiments, the second chamber 111 has a volume of no greater than about 250 microliters, in some embodiments, no greater than about 200 microliters, in some embodiments, no greater than about 175 microliters, and in some embodiments, no greater than about 100 microliters. In some embodiments, the second chamber 111 has a volume of about 208 microliters, or 210 microliters.

In some embodiments, the volume of the second chamber 111 is at least about 5% of the volume of the first chamber 109, and in some embodiments, at least about 7%. In some embodiments, the volume of the second chamber 111 is no greater than about 20% of the volume of the first chamber 109, in some embodiments, no greater than about 15%, in some embodiments, no greater than about 12%, and in some embodiments, no greater than about 10%. In some embodiments, the volume of the second chamber 111 is about 7.5% of the volume of the first chamber 109.

In some embodiments, the volume of the second chamber 111 is no greater than about 60% of the volume of the liquid 122 housed in the container 120, in some embodiments, no greater than about 50%, and in some embodiments, no greater than about 25%. In some embodiments, designing the second chamber 111 to have a volume that is substantially less than that of the liquid 122 housed in the container 120 can ensure that the additional liquid volume can compensate for unintended evaporation.

In some embodiments, the first chamber 109 (i.e., formed by the upper portion 116 of the first portion 104 of the housing 102) has a cross-sectional area (or average cross-sectional area) at the transition between the first chamber 109 and the second chamber 111, or at the position adjacent the second chamber 111, of at least about 25 $mm^2$; in some embodiments, at least about 30 $mm^2$; and in some embodiments, at least about 40 $mm^2$. In some embodiments, the first chamber 109 has a cross-sectional area at the transition between the first chamber 109 and the second chamber 111, or at the position adjacent the second chamber 111, of no greater than about 100 $mm^2$, in some embodiments, no greater than about 75 $mm^2$, and in some embodiments, no greater than about 50 $mm^2$.

In some embodiments, the second chamber 111 (i.e., formed by the lower portion 114 of the first portion 104 of the housing 102) has a cross-sectional area at the transition between the first chamber 109 and the second chamber 111, or at the position adjacent the first chamber 109, of at least about 5 $mm^2$, in some embodiments, at least about 10 $mm^2$, and in some embodiments, at least about 15 $mm^2$. In some embodiments, the second chamber 111 has a cross-sectional area (or average cross-sectional area) of no greater than about 30 $mm^2$, in some embodiments, no greater than about 25 $mm^2$, and in some embodiments, no greater than about $mm^2$.

In some embodiments, the cross-sectional area of the second chamber 111 at the transition between the first chamber 109 and the second chamber 111 can be no greater than about 60% of the cross-sectional area of the first chamber 109 at the transition, in some embodiments, no greater than about 50%, in some embodiments, no greater than about 40%, and in some embodiments, no greater than about 30%.

In some embodiments, the biological sterilization indicator 100 can further include a substrate 119. In some embodiments, as shown in FIGS. 1-4 and 6, the substrate 119 can be dimensioned to be positioned adjacent the wall 118, and particularly, to rest atop the wall 118. The substrate 119 can be positioned between the upper portion 116 (i.e., the first chamber 109) and the lower portion 114 (i.e., the second chamber 111) of the biological sterilization indicator 100 and, in some embodiments, can at least partially define the first chamber 109 and the second chamber 111. As such, in some embodiments, the substrate 119 can be positioned between the container 120 and the spores 115. In some embodiments, the substrate 119 can be positioned in the first chamber 109, or on a first chamber side of the wall 118, such that the substrate 119 is not positioned in the second chamber 111.

In addition, the substrate 119 can be positioned to minimize diffusion of an assay signal (e.g., fluorescence) out of the second chamber 111. In some embodiments, depending on the material makeup of the substrate 119, the substrate 119 can also absorb dyes, indicator reagents, or other materials from solution that may inhibit accurate reading of a signal from the biological sterilization indicator 100 (i.e., "inhibitors"). In some embodiments, as shown in FIGS. 1-4, 6 and 7, the substrate 119 can include one or more apertures 121, which can be configured to control (i.e., facilitate and/or limit, depending on number, size, shape, and/or location) fluid movement between the first chamber 109 and the second chamber 111 of the biological sterilization indicator 100, and particularly, which can facilitate movement of the liquid 122 to the spores 115 when the container 120 is fractured. By way of example only, particular benefits or advantages were observed when the aperture 121 was positioned front of (or "forward of") the center of the substrate 119, as shown. In the embodiment illustrated in FIGS. 1-7, the "front" of the biological sterilization indicator 100 or components therein can generally be described as being toward a flat face 126. In general, the "front" of the biological sterilization indicator 100 can refer to the portion of the biological sterilization indicator 100 that will be interrogated by a reading apparatus.

In addition, by way of example only, the aperture 121 is illustrated as being circular or round; however, other cross-sectional aperture shapes are possible and within the scope of the present disclosure. Furthermore, by way of example only, and as shown in FIG. 3, the substrate 119 is shaped to substantially fill the first chamber cross-sectional area at the transition between the first chamber 109 and the second chamber 111. However, other shapes of the substrate 119 are possible and can be adapted to accommodate the housing 102, the first chamber 109, the second chamber 111, the wall 118, or another component of the biological sterilization indicator 100.

As mentioned above, the second chamber 111 can include a volume to be interrogated. Such a volume can be assayed for spore viability to determine the lethality or effectiveness of a sterilization procedure. In some embodiments, the volume to be interrogated can be all or a portion of the second chamber 111. In some embodiments, the substrate 119 can be positioned outside of the volume to be interrogated, which can minimize the number of structures in the volume that may interfere with the assaying processes. For example, in some embodiments, the substrate 119 can be positioned such that the substrate 119 is not in direct contact with at least one of the spores 115, the spore carrier 135, and the spore reservoir 136. In some embodiments, the substrate 119 can be positioned such that the substrate 119 is not located between a detection system (e.g., an optical detection system, such as a fluorescence excitation source and an emission detector) and at least one of the spores 115, the spore carrier 135, and the spore reservoir 136. The substrate 119 can have the above positions when the container 120 is in the first state and/or the second state, but particularly, when the container 120 is in the second state.

In some embodiments, substrate position in the biological sterilization indicator 100 can affect the correlation of a rapid detection system for spore viability (e.g., fluorescence detection) with a slower (e.g., overnight or 24-hr) detection system (e.g., a pH indicator that can exhibit a color change (e.g., in 24 hr) in response to spore growth). For example, in some embodiments, the substrate 119 can improve the correlation of fluorescence readings at various timepoints with growth results after 24 hrs, as shown in Example 1 below. Particularly, when the substrate 119 is positioned in a "first" position—as described herein and as shown in FIGS. 1, 2, and 4-7—the fluorescence can accurately correlate to growth. As shown in Example 1, such correlation can be an improvement over other substrate positions and biological sterilization indicators with no substrate.

In addition, the substrate 119 can be positioned in the biological sterilization indicator 100 such that the substrate 119 is not in direct contact with the container 120 when the container 120 is in the first state. For example, in some embodiments, the substrate 119 can be positioned in the first chamber 109 (e.g., adjacent a bottom end (e.g., the second end 113) of the first chamber 109), but even in such embodiments, the substrate 119 can be positioned such that the substrate 119 does not contact the container 120. For example, as shown in FIGS. 1-2 and 4-6, in some embodiments, the insert 130 can be positioned between the container 120 and the substrate 119 when the container 120 is in the first state, such that the insert 130 holds the container 120 in the first state. The insert 130, or a portion thereof, can be positioned adjacent the substrate 119. For example, as shown in the illustrated embodiment, the substrate 119 can be positioned between (e.g., sandwiched between) the insert 130 and the wall 118. As such, in some embodiments, the substrate 119 can be positioned between the insert 130 and the second chamber 111. In some embodiments, when the container 120 is in the second state, fractured portions, or shards, of the container 120 may come into contact with the substrate 119, but in some embodiments, the fracture portions of the container 120 do not come into contact with the substrate 119.

As mentioned above, in some embodiments, the substrate 119 can be positioned and configured to control or affect fluid flow in the biological sterilization indicator 100, and particularly, to control fluid flow between the first chamber 109 and the second chamber 111. For example, in some embodiments, the substrate 119 can be configured (e.g., sized, shaped, oriented, and/or constructed of certain materials) to control the rate at which a sterilant is delivered to the second chamber 111 (and to the spores 115), and can thereby control the "kill rate" of the spores 115. For example, the sterilant delivery rate can be less than it otherwise would be if the substrate 119 were not present between the first chamber 109 and the second chamber 111. That is, in some embodiments, the substrate 119 can control the kill rate by selectively protecting the spores 115. In some embodiments, the substrate 119 can serve as a "valve" for controlling fluid flow, and particularly, for controlling sterilant delivery, in the biological sterilization indicator 100. Furthermore, in some embodiments, the substrate 119 can have properties that enhance or modulate a response generated by the spores 115, for example, if the spores 115 survive a sterilization process.

Furthermore, in some embodiments, the substrate 119 can be configured (e.g., sized, shaped, positioned, oriented, and/or constructed of certain materials) to control the rate at which detectable products diffuse out of the volume to be interrogated. In some embodiments, the detectable product can include a signal (e.g., a fluorescent signal) that indicates spore viability, and in some embodiments, the detectable product can be the spore(s) 115 itself. Controlling the diffusion of detectable products out of the volume to be interrogated can be particularly useful in embodiments in which the volume of the liquid 122 is greater than the volume of the second chamber 111 (or of the volume to be interrogated), because the liquid 112 in such embodiments can extend in the biological sterilization indicator 100 to a higher level than the second chamber 111 (or the volume to be interrogated) when the container 120 is in its second, fractured, state. In such embodiments, detectable products can be free to move throughout the full volume of the liquid 122 (i.e., to a volume outside of the volume to be interrogated), unless there is some barrier or means for controlling such diffusion, such as the substrate 119. For example, in some embodiments, the substrate 119 can be positioned at a level just above the volume to be interrogated (i.e., below the level of the liquid 122), to inhibit movement of the detectable products to the portion of the liquid 122 that is positioned above the substrate 119.

In some embodiments, the substrate 119 can control sterilant delivery rate (e.g., into the second chamber 111) and/or the diffusion rate of detectable products (e.g., out of the second chamber 111) by providing a physical barrier or blockage to the sterilant and/or the detectable products. Such a physical barrier can also function to collect broken portions of the container 120 when the container 120 is in the second, fractured, state to inhibit movement of the broken portions into the volume to be interrogated where the broken portions could block, refract, reflect, or otherwise interfere with detection processes (e.g., optical detection processes).

In addition, in some embodiments, the liquid 122, either before or after coming into fluid communication with the spores 115, can include one or more inhibitors, or other components, that may interfere with an accurate assay or detection process. In some embodiments, examples of inhibitors can include at least one of dyes, indicator reagents, other materials or substances that may inhibit a reaction (e.g., an enzymatic reaction) necessary for detection of spore viability (e.g., salts, etc.), other materials or substances that may interfere with the detection process, or combinations thereof. In such embodiments, the substrate 119 can be configured to absorb and/or selectively concentrate one or more inhibitors from the liquid 122, or at least from the volume of the liquid 122 to be interrogated. Determining that the substrate receives and concentrates the indicator reagent (or biological derivative thereof) can be accomplished by fluidically contacting an aqueous medium comprising the indicator reagent (or biological derivative thereof) with the substrate for a period of time and analyzing the substrate for the presence of the reagent (or biological derivative thereof), as shown in Example 3.

For example, in some embodiments, more than one indicator reagent can be present in the liquid 122, either before contacting the spores 115 or as a result of contacting the spores 115. In such embodiments, while a first indicator reagent (e.g., used for fluorescence detection) may be necessary for spore viability detection, a second indicator reagent (e.g., a pH indicator) may actually interfere with the detection of the first indicator reagent. By way of example only, in embodiments in which the second indicator reagent is a pH indicator (e.g., one or more of the pH indicators described below), the pH indicator may conflict or interfere with the fluorescence reading of the first indicator reagent, for example, in embodiments in which the pH indicator emits electromagnetic radiation at a wavelength that is similar to the spectral band of the fluorescence of the first indicator reagent (e.g., when the pH indicator exhibits a color shift). In such embodiments, the substrate 119 can be configured (e.g., formed of an appropriate material) to absorb and/or selectively concentrate the second indicator reagent when positioned in contact with the liquid 122 to reduce the concentration of the second indicator reagent in the liquid 122, or at least in the volume of the liquid 122 to be interrogated.

A number of chromic and fluorogenic enzyme substrates of diverse origin can be used in methods to detect predetermined biological activities, and are suitable for use as the first or second indicator reagent according to the present disclosure. Among these are a variety of fluorogenic 4-methylumbelliferyl derivatives (hydrolysable to 4-methylumbelliferone); derivatives of 7-amido-4-methyl-coumarin, e.g. as disclosed in GB Patent No. 1,547,747 and European Patent No. 0,000,063, each of which is incorporated herein by reference in its entirety; diacetylfluorescein derivatives; and fluorescamine.

For example, a first indicator reagent can include a reagent that has a first absorption spectrum and, thus, it absorbs light in the ultraviolet and/or visible wavelengths of the electromagnetic spectrum.

In some embodiments, the first indicator reagent can be an indicator dye (e.g., a pH indicator dye, a redox dye). The specific indicator dye used to detect any given biological activity will be selected according to criteria that are known in the art, including, for example, compatibility (e.g., preferably non-inhibitory) with the biological activity to be detected, solubility, and the detection system (e.g., visual and/or automated).

The indicator dye may be a pH indicator suitable to detect the biological activity. The indicator dye can be selected according to criteria known in the art such as, for example, pH range, compatibility with the biological activity, and solubility. In some embodiments, a salt form of the pH indicator may be used, for example, to increase the solubility of the pH indicator in an aqueous mixture. Nonlimiting examples of suitable pH indicator dyes include, for example, thymol blue, tropeolin OO, methyl yellow, methyl orange, bromphenol blue, bromocresol green, methyl red, bromthymol blue, phenol red, neutral red, phenolphthalein, thymolphthalein, alizarin yellow, tropeolin O, nitramine, trinitrobenzoic acid, thymol blue, bromphenol blue, tetrabromphenol blue, bromocresol green, bromocresol purple, methyl red, bromthymol blue, phenol red, Congo red, and cresol red.

In some embodiments, the indicator dye may be an oxidation-reduction indicator (also called a redox indicator) suitable to detect the biological activity. Oxidation-reduction indicator dyes may be pH-dependent or pH-independent. Nonlimiting examples of oxidation-reduction indicator dyes include 2,2'-Bipyridine (Ru complex), Nitrophenanthroline (Fe complex), N-Phenylanthranilic acid, 1,10-Phenanthroline (Fe complex), N-Ethoxychrysoidine, 2,2'-Bipyridine (Fe complex), 5,6-Dimethylphenanthroline (Fe complex), o-Dianisidine, Sodium diphenylamine sulfonate, Diphenylbenzidine, Diphenylamine, Viologen, Sodium 2,6-Dibromophenol-indophenol, Sodium 2,6-Dichlorophenol-indophenol, Sodium o-Cresol indophenol, Thionine (syn. Lauth's violet), Methylene blue, Indigotetrasulfonic acid, Indigotrisulfonic acid, Indigodisulfonic acid, Indigomonosulfonic acid, Phenosafranin, Safranin T, and Neutral red.

In some embodiments, the first indicator reagent can be a sulfonphthalein pH indicator (e.g. bromocresol purple), as shown in Example 3. The sulfonphthalein pH indicator (e.g., bromocresol purple) can be present in the aqueous mixture at a concentration of about 0.03 g per liter. The sulfonphthalein pH indicator can be received and concentrated by a substrate (e.g. a charged nylon substrate such as, for example, MAGNAPROBE 0.45 micron charged nylon membrane, part number NP0HY00010, available from GE Osmonics Labstore, Minnetonka, Minn.). The substrate can be configured as a generally planar strip (e.g. a strip that is about 3 mm by about 10 mm).

A second indicator reagent, for example, can be converted to a second biological derivative. The second biological derivative comprises a reagent that has a second absorption spectrum. Furthermore, the second biological derivative has a characteristic second emission spectrum (e.g., a fluorescent emission spectrum). In some embodiments, the second biological derivative has a characteristic second absorption spectrum that includes wavelengths in the ultraviolet portion of the electromagnetic energy spectrum. The second emission spectrum of the second biological derivative may include wavelengths in the visible portion of the electromagnetic energy spectrum.

Suitable compounds for use as a second indicator reagent include fluorogenic compounds (e.g., fluorogenic enzyme substrates). Fluorogenic enzyme substrates include 4-methylumbelliferyl derivatives, 7-amido-4-methylcoumarin derivatives, and diacetylfluorescein derivatives.

Suitable 4-methylumbelliferyl derivatives include, for example: 4-methylumbelliferyl-2-acetamido-4, 6-O-benzylidene-2-deoxy-β-D-glucopyranoside; 4-methylumbelliferyl acetate; 4-methylumbelliferyl-N-acetyl-β-D-galactosaminide; 4-methylumbelliferyl-N-acetyl-α-D-glucosaminide; 4-methylumbelliferyl-N-acetyl-β-D-glucosaminide; 2'-(4-methylumbelliferyl)-α-D-N-acetyl neuraminic acid; 4-methylumbelliferyl α-L-arabinofuranoside; 4-methylumbelliferyl α-L-arabinoside; 4-methylumbelliferyl butyrate; 4-methylumbelliferyl β-D-cellobioside; methylumbelliferyl N'diacetyl chitobioside; 4-methylumbelliferyl elaidate; 4-methylumbelliferyl β-D-fucoside; 4-methylumbelliferyl α-L-fucoside; 4-methylumbelliferyl β-L-fucoside; 4-methylumbelliferyl α-D-galactoside; 4-methylumbelliferyl β-D-galactoside; 4-methylumbelliferyl α-D-glucoside; 4-methylumbelliferyl β-D-glucoside; 4-methylumbelliferyl β-D-glucuronide; 4-methylumbelliferyl p-guanidinobenzoate; 4-methylumbelliferyl heptanoate; 4-methylumbelliferyl α-D-mannopyranoside; 4-methylumbelliferyl β-D-mannopyranoside; 4-methylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl N',N''-triacetylchitotriose; 4-methylumbelliferyl 2,3,5-tri-o-benzoyl-α-L-arabinofuranoside; 4-methylumbelliferyl-p-trimethylammonium cinnamate chloride; and 4-methylumbelliferyl β-D-xyloside.

Suitable 7-amido-4-methylcoumarin derivatives include, for example: L-alanine-7-amido-4-methylcoumarin; L-proline 7-amido-4-methylcoumarin; L-tyrosine-7-amido-4-methylcoumarin; L-leucine-7-amido-4-methylcoumarin; L-phenylalanine-7-amido-4-methylcoumarin; and 7-glutarylphenylalanine-7-amido-4-methylcoumarin.

Suitable peptide derivatives of 7-amido-4-methyl coumarin include, for example: N-t-BOC-Ile-Glu-Gly-Arg 7-amido-4-methylcoumarin; N-t-BOC-Leu-Ser-Thr-Arg 7-amido-4-methylcoumarin; N—CBZ-Phe-Arg 7-amido-4-methyl-coumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Suitable diacetylfluorescein derivatives include, for example, fluorescein diacetate, fluorescein di-(β-D-galactopyranoside), and fluorescein dilaurate.

Where the biological activity to be detected is alpha-D-glucosidase, chymotrypsin, or fatty acid esterase, e.g., from *Geobacillus stearothermophilus*, preferred fluorogenic enzyme substrates are 4-methylumbelliferyl-alpha-D-glucoside, 7-glutarylphenylalanine-7-amido4methyl coumarin, or 4-methylumbelliferyl heptanoate, respectively. Where the biological activity to be detected is alpha-L-arabinofuranosidase, e.g., derived from *Bacillus subtilis*, a preferred fluorogenic enzyme substrate is 4-methylumbelliferyl-alpha-L-arabinofuranoside. Where the biological activity to be detected is beta-D-glucosidase, e.g., derived from *Bacillus subtilis*, a preferred fluorogenic enzyme substrate is 4-methylumbelliferyl-beta-D-glucoside.

In order to detect a biological activity comprising an enzyme, the operator should be knowledgeable concerning the enzyme activity to be detected and the enzyme substrates that will react with the enzyme so as to produce a product which can be detected either by its fluorescence, color, etc. (see M. Roth, Methods of Biochemical Analysis, Vol. 7, D. Glock, Ed., Interscience Publishers, New York, N.Y., 1969, which is incorporated herein by reference in its entirety). The appropriate enzyme substrate to be utilized will depend upon the biological activity to be detected.

Methods of the present disclosure can include a first indicator reagent with a first absorption spectrum and a second indicator reagent that is converted by a biological activity to a second biological derivative with a second emission spectrum, wherein the first absorption spectrum at least partially overlaps the second emission spectrum. Thus, when both the first indicator reagent and the second biological derivative are present in a liquid mixture, the first indicator reagent may absorb at least a portion of the light emitted by the second indicator reagent, thereby diminishing the ability to detect the second biological derivative.

Figure 8:
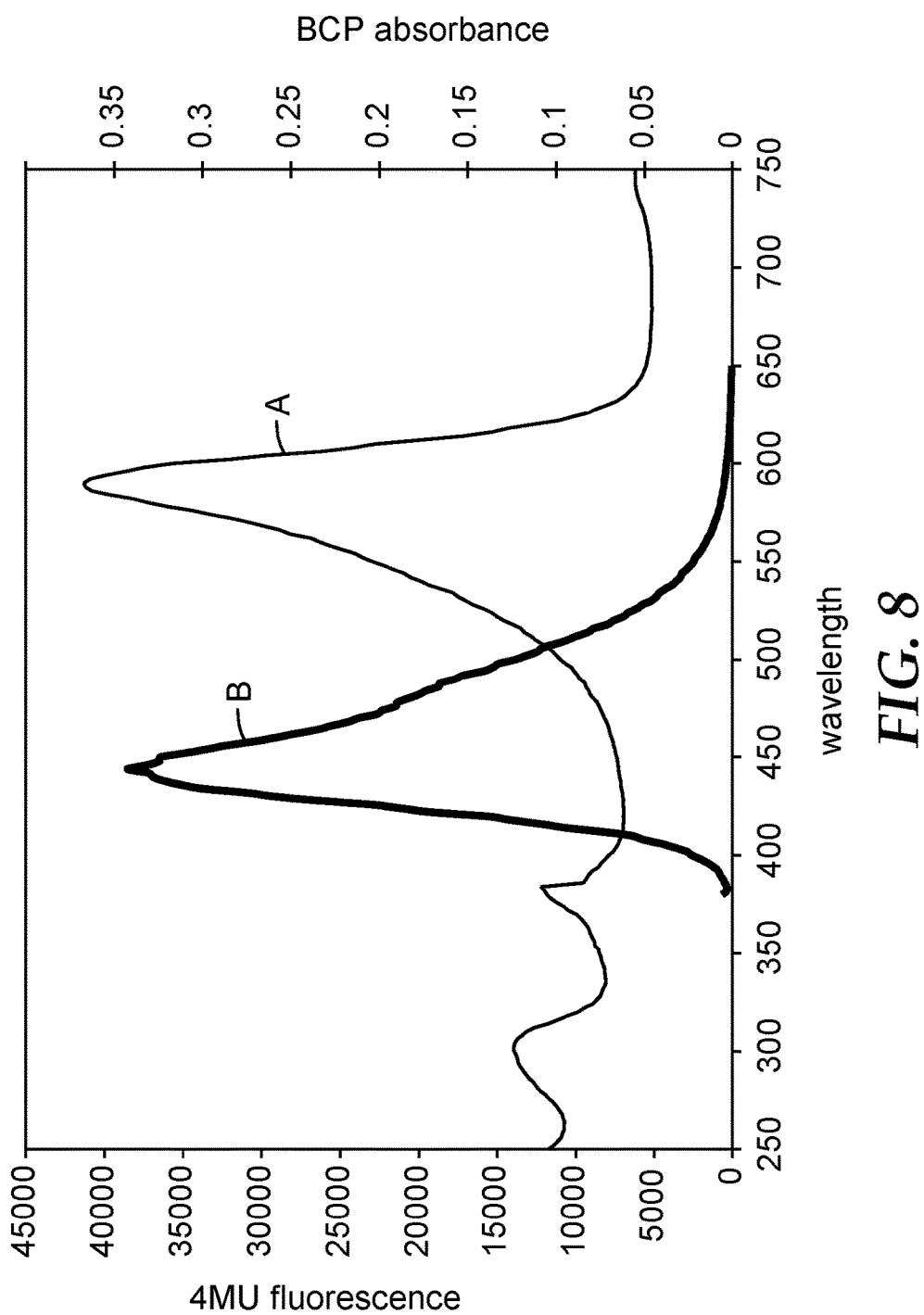
FIG. 8 is a UV-visible absorbance spectrum of an aqueous solution of bromocresol purple and a fluorescence emission spectrum of a solution of 4-methylumbelliferone.

A graph can illustrate the relationship between a first indicator reagent and a second biological derivative according to the present disclosure. FIG. 8 shows the absorbance spectrum of Bromocresol Purple (hereinafter, called "BCP"), an exemplary first indicator reagent, and the fluorescence emission spectrum of 4-methylumbelliferone (hereinafter, called "4MU"), a possible biological derivative of 4-methylumbelliferyl β-D-glucoside, an exemplary second indicator reagent. The spectra were obtained as described in Examples 7 and 8.

Line "A", which shows the absorbance spectrum of BCP, indicates an absorbance maximum in the visible range around 600 nm, with relatively less absorbance by BCP in the 425-550 nm wavelengths. The data show an absorbance peak in the visible wavelengths around 600 nm and an absorbance peak in the ultraviolet wavelengths at <330 nm. Line "B", which shows the fluorescence emission spectrum of 4MU indicates an emission maximum around 450 nm, with relatively less emission in the ranges from 375-425 nm and from 475-525 nm. It can be seen in FIG. 8 that the absorbance spectrum of BCP substantially overlaps the entire fluorescence emission peak (centered around 450 nm) of 4MU.

A person of ordinary skill in the relevant art will recognize that the amount of absorbance of any particular wavelength of light by a solution containing a first indicator reagent will be influenced by the concentration of first indicator reagent in the solution and the molar extinction coefficient of the indicator reagent at the selected wavelength. The skilled person will also recognize that the amount of light emission of any particular wavelength by a solution containing a biological derivative of a second indicator reagent will be influenced by the concentration of the second biological derivative in the solution and the fluorescence quantum yield of the biological derivative. Therefore, the concentration of the first indicator reagent in the liquid mixture can be selected in conjunction with an appropriate substrate to permit i) the substrate to remove enough first indicator substrate from the liquid mixture to allow more sensitive detection of the second biological derivative and ii) the first indicator reagent (or biological derivative thereof) to be easily detected on the substrate material.

The combination of bromocresol purple and 4-methylumbelliferyl-β-D-glucoside represents an example of suitable first and second indicator reagents, respectively, according to the present disclosure. This combination can be used to detect a first biological activity such as the fermentation of a carbohydrate to acid end products and a second biological activity such as -β-D-glucosidase enzyme activity, for example. These activities can indicate the presence or absence of a viable spore following the exposure of a biological sterilization indicator to a sterilization process, for example. The bromocresol purple can be used at a concentration of about 0.03 g/L in the aqueous mixture, for example. The 4-methylumbelliferyl-β-D-glucoside can be used, for example, at a concentration of about 0.05 to about 0.5 g/L (e.g., about 0.05 g/L, about 0.06 g/L, about 0.07 g/L, about 0.08 g/L, about 0.09 g/L, about 0.1 g/L, about 0.15 g/L, about 0.2 g/L, about 0.25 g/L, about 0.3 g/L, about 0.35 g/L, about 0.4 g/L, about 0.45 g/L, about 0.5 g/L) in the aqueous mixture.

Thus, according to the present disclosure, the first indicator reagent may interfere with the detection of an otherwise detectable amount of the biological derivative of the second indicator reagent. The spectral interference between any proposed first and second indicator reagents can be demonstrated by a person of ordinary skill in the art by performing the following simple experiment.

First, the operator makes a relatively-dilute, but fluorescently-detectable, aqueous solution of the expected biological derivative of the proposed second indicator reagent. For example, if the second indicator reagent is a 4-methylumbelliferyl compound, the expected biological derivative is 4MU. The solution can contain, for example, about 0.05 to 0.2 micrograms per milliliter 4MU. Next, the operator adds an effective amount of the proposed first indicator reagent. For example, if BCP is the proposed first indicator reagent, it can be added at a concentration (e.g., 0.04 milligrams per milliliter) that is used in microbiological growth media for the detection of fermentative microorganisms. By comparing the fluorescence of the 4MU solutions with and without the BCP, it can be determined whether the first indicator reagent (in this example, the BCP) can interfere with the detection of the biological derivative of the second indicator reagent (in this case, the 4MU). The operator can then test whether adding reduced amounts of BCP to the 4MU solution improves the detection of relatively low concentrations of 4MU. This type of experiment easily can be performed with any combination of first and second indicator reagents. An example of this procedure is shown in Example 9.

In addition, in some embodiments (e.g., in embodiments in which the wall 118 is slanted and the substrate 119 is positioned adjacent the wall 118), the substrate 119 can be angled or slanted, for example, oriented at a non-zero and non-right angle with respect to the longitudinal direction $D_L$ of the housing 102. Such angling or slanting of the substrate 119 can facilitate the movement of the liquid 122 from the first chamber 109 to the second chamber 111 after sterilization and after the container 120 has been broken to release the liquid 122.

In some embodiments, the substrate 119 can be formed of a variety of materials to accomplish one or more of the above functions. Examples of substrate materials can include, but are not limited to, cotton, glass wool, cloth, nonwoven polypropylene, nonwoven rayon, nonwoven polypropylene/rayon blend, nonwoven nylon, nonwoven glass fiber or other nonwoven fibers, filter papers, microporous hydrophobic and hydrophilic films, glass fibers, open celled polymeric foams, and semi-permeable plastic films (e.g., particle filled films, thermally induced phase separation (TIPS) membranes, etc.), and combinations thereof. For example, in embodiments in which the substrate 119 can be used to selectively concentrate one more indicator reagents (e.g., bromocresol purple (BCP)), the substrate 119 can be formed of a charged nylon (such as a reprobing, charged transfer membrane available from GE Water & Process Technologies, Trevose, Pa., under the trade designation "MAGNAPROBE" (e.g., 0.45 micron pore size, 30 cm×3 m roll, Catalog No. NP0HY00010, Material No. 1226566)).

Examples of methods and systems that can employ the substrate 119 are also described in U.S. Publication No. 2013/0210048, entitled "Method of Detecting a Biological Activity," and U.S. Pat. No. 8,802,392, entitled "Method of Detecting a Biological Activity," each of which is incorporated herein by reference in its entirety.

In some embodiments, at least a portion of one or more of the insert 130, the wall 118, and/or the substrate 119, or an opening therein, can provide fluid communication between the first chamber 109 (e.g., in the upper portion 116) and the second chamber 111 (e.g., in the lower portion 114), and/or can control the fluid communication between the first chamber 109 and the second chamber 111 (e.g., by controlling the extent of fluid connection between the first chamber 109 and the second chamber 111).

The biological sterilization indicator 100 can include a first fluid path 160 that can be positioned to fluidly couple the first chamber 109 and the second chamber 111, and which can allow sterilant (e.g., during sterilization, when the container 120 is in a first, unfractured, state) and/or the liquid 122 (e.g., after sterilization and during activation, when the container 120 is in a second, fractured, state) to reach the spores 115. In the illustrated embodiment the first fluid path 160 can generally be defined by one or more of the following: (1) the insert 130, e.g., via an aperture 177 described below, an opening formed in the insert 130, and/or any open spaces around the insert 130, such as between the insert 130 (e.g., a front portion thereof) and the housing 102; (2) the wall 118, e.g., the aperture 117 defined by the wall 118; (3) the substrate 119, e.g., the aperture 121 formed therein, or any open spaces around the substrate 119, such as between the substrate 119 (e.g., a front portion thereof) and the housing 102; (4) the housing 102, e.g., any openings or spaces formed therein; and combinations thereof. As a result, the first fluid path 160 is generally represented in the illustrated embodiment by an arrow in FIGS. 4 and 7.

The biological sterilization indicator 100 can further include a second fluid path 162 positioned to fluidly couple the second chamber 111 with another chamber or portion of the biological sterilization indicator 100, such as the first chamber 109. The second fluid path 162 can be further positioned to allow gas that was previously present in the second chamber 111 to be displaced and to exit the second chamber 111, for example, when the sterilant and/or the liquid 122 is moved into the second chamber 111. As such, the second fluid path 162, which is described in greater detail below, can serve as an internal vent in the biological sterilization indicator 100.

In some embodiments, the substrate 119 can provide a physical barrier or blockage between the first chamber 109 and the second chamber 111 which can allow for at least one of the following: controlling the sterilant delivery rate/kill rate at which sterilant is delivered into the second chamber 111; controlling the diffusion of spores 115 and/or detectable products out of the second chamber 111; controlling the delivery rate of the liquid 122 to the second chamber 111 (and to the spores 115) when the container 120 is in the second, fractured, state; or a combination thereof.

Because, in some embodiments, the substrate 119 can provide a physical barrier to delivering the liquid 122 to the second chamber 111 during activation (i.e., when the container 120 is in the second state), aperture 121 in the substrate 119 and/or the angle of the substrate 119 can be controlled to effect a desired liquid delivery rate. In addition, or alternatively, the second fluid path 162 can provide a vent for any gas or air that is trapped in the second chamber 111 to facilitate moving the liquid 122 through or past the substrate 119 and into the second chamber 111 when desired.

In addition, or alternatively, the housing 102 can be configured (e.g., formed of an appropriate material and/or configured with microstructured grooves or other physical surface modifications) to facilitate moving the liquid 122 to the second chamber 111 when desired. For example, as shown in Example 2 below, some substrate materials can be more effective in facilitating the movement of the liquid 122 into the second chamber 111, which can be tested using the flick test described in Example 2. By way of example only, in some embodiments, a substrate 119 formed of a charged nylon (such as the MAGNAPROBE nylon described above, available from GE Water & Process Technologies) can be more effective in delivering the liquid 122 to the second chamber 111 after the container 120 is fractured, than a substrate 119 formed of paper (such as Whatman Paper, e.g., Grade 1 Chr cellulose chromatography paper, available from Whatman Inc. USA, Piscataway, N.J.). Particularly, the charged nylon can be more effective in moving the liquid 122 into the second chamber 111 without additional assistance (e.g., without requiring a downward shake, or "flick," of the biological sterilization indicator 100).

In some embodiments, the liquid 122 can include a nutrient medium for the spores, such as a germination medium that will promote germination of surviving spores. In some embodiments, the liquid 122 can include water (or another solvent) that can be combined with nutrients to form a nutrient medium. Suitable nutrients can include nutrients necessary to promote germination and/or growth of surviving spores and may be provided in a dry form (e.g., powdered form, tablet form, caplet form, capsule form, a film or coating, entrapped in a bead or other carrier, another suitable shape or configuration, or a combination thereof) in the reservoir 103, for example, in a region of the biological sterilization indicator 100 near the spores 115.

The nutrient medium can generally be selected to induce germination and initial outgrowth of the spores, if viable. The nutrient medium can include one or more sugars, including, but not limited to, glucose, fructose, cellibiose, or the like, or a combination thereof. The nutrient medium can also include a salt, including, but not limited to, potassium chloride, calcium chloride, or the like, or a combination thereof. In some embodiments, the nutrient can further include at least one amino acid, including, but not limited to, at least one of methionine, phenylalanine, and tryptophan.

In some embodiments, the nutrient medium can include indicator molecules or reagents, for example, indicator molecules having optical properties that change in response to germination or growth of the spores. Suitable indicator molecules or reagents can include, but are not limited to, pH indicator molecules (e.g., bromocresol purple (BCP) as shown in the Examples, bromocresol green (BCG), chlorophenol red (CPR), bromthymol blue (BTB), bromophenol blue (BPB), other sulfonephthalein dyes, methyl red, or combinations thereof), enzyme substrates (e.g., 4-methylumbelliferyl-α-D-glucoside), DNA binding dyes, RNA binding dyes, other suitable indicator molecules, or a combination thereof. In some embodiments, the combination of bromcresol purple and 4-methylumbelliferyl-α-D-glucoside represents an example of a pair of indicator reagents that can be employed together. This combination can be used to detect a first biological activity such as the fermentation of a carbohydrate to acid end products and a second biological activity such as α-D-glucosidase enzyme activity, for example. These activities can indicate the presence or absence of a viable spore following the exposure of a biological sterilization indicator to a sterilization process, for example. The bromcresol purple can be used at a concentration of about 0.03 g/L, for example, in an aqueous mixture. The 4-methylumbelliferyl-α-D-glucoside can be used, for example, at a concentration of about 0.05 to about 0.5 g/L (e.g., about 0.05 g/L, about 0.06 g/L, about 0.07 g/L, about 0.08 g/L, about 0.09 g/L, about 0.1 g/L, about 0.15 g/L, about 0.2 g/L, about 0.25 g/L, about 0.3 g/L, about 0.35 g/L, about 0.4 g/L, about 0.45 g/L, about 0.5 g/L), for example, in an aqueous mixture.

As shown in FIGS. 1-7, the biological sterilization indicator 100 can further include an insert 130. In some embodiments, the insert 130 can be adapted to hold or carry the container 120, such that the container 120 is held intact in a location separate from the spores 115 during sterilization. That is, in some embodiments, the insert 130 can include (or function as) a carrier 132 (see FIG. 3) for the container 120, particularly, before the container 120 is broken during the activation step (i.e., the step in which the liquid 122 is released from the container 120 and introduced to the spores 115, which can occur after a sterilization process). In some embodiments, the insert 130 can be further adapted to allow the container 120 to move at least somewhat in the housing 102, e.g., longitudinally with respect to the housing 102. The insert 130 of the illustrated embodiment is described in greater detail below. Examples of other suitable inserts and carriers are described in U.S. Pat. No. 8,980,622.

In some embodiments, the biological sterilization indicator 100 can further include a spore carrier 135, as shown in FIGS. 1-4 and 6. However, in some embodiments, the insert 130 can be modified to include a portion adapted to house the spores 115. For example, in some embodiments, the insert 130 and the spore carrier 135 can be integrally formed as one insert comprising a first portion adapted to hold and eventually fracture the container 120, when desired, and a second portion adapted to house the spores 115 in a region of the biological sterilization indicator 100 that is separate from the container 120 during sterilization (i.e., prior to fracture).

As shown in FIGS. 1-4 and 6, the spore carrier 135 can include a spore reservoir 136 (which can also be referred to as a depression, divot, well, recess, or the like), in which the spores 115 can be positioned, either directly or on a substrate. In embodiments employing a nutrient medium that is positioned to be mixed with the liquid 122 when it is released from the container 120, the nutrient medium can be positioned near or in the spore reservoir 136, and the nutrient medium can be mixed with (e.g., dissolved in) the water when the water is released from the container 120. By way of example only, in embodiments in which the nutrient medium is provided in a dry form, the dry form can be present within the reservoir 103, the spore reservoir 136, on a substrate for the spores, or a combination thereof. In some embodiments, a combination of liquid and dry nutrient media can be employed.

In some embodiments, the spore reservoir 136 has a volume of at least about 1 microliter, in some embodiments, at least about 5 microliters, and in some embodiments, at least about 10 microliters. In some embodiments, the spore reservoir 136 has a volume of no greater than about 250 microliters, in some embodiments, no greater than about 175 microliters, and in some embodiments, no greater than about 100 microliters.

As shown in FIGS. 4 and 6, in some embodiments, the biological sterilization indicator 100 can further include a rib or protrusion 165 that can be coupled to or integrally formed with a wall 108 of the housing 102, which can be positioned to maintain the spore carrier 135 in a desired location in the housing 102 and/or at a desired angle or orientation, for example, with respect to detection systems (e.g., optical detection systems) of the reading apparatus 12.

As shown in FIGS. 1-4 and 6, the second portion 106 of the housing 102 can be adapted to be coupled to the first portion 104. For example, as shown, the second portion 106 can be adapted to be coupled to the upper portion 116 (e.g., the first end 101) of the first portion 104 of the housing 102. In some embodiments, as shown in FIGS. 1-4, the second portion 106 can be in the form of a cap that can be dimensioned to receive at least a portion of the first portion 104 of the housing 102.

As shown in FIGS. 1-2 and 4-5, during sterilization and before activation, the second portion 106 can be in a first "unactivated" position 148 with respect to the first portion 104, and the container 120 can be in a first, intact, state. As shown in FIG. 6, the second portion 106 of the housing 102 can be moved to a second "activated" position 150 (e.g., where the second portion 106 is fully depressed) with respect to the first portion 104, and the container 120 can be in a second, fractured, state. For example, after sterilization, the biological sterilization indicator 100 can be activated by moving the second portion 106 from the first position 148 to the second position 150 (i.e., a sufficient amount) to cause fracturing of the container 120 and to release the liquid 122 from the container 120, to allow the liquid 122 to be in fluid communication with the spores 115. The biological sterilization indicator 100 can be activated prior to positioning the biological sterilization indicator 100 in a well of a reading apparatus, after positioning the biological sterilization indicator 100 in the well, or as the biological sterilization indicator 100 is positioned in the well (i.e., the biological sterilization indicator 100 can be slid into place in the reading apparatus, and the second portion 106 can continue to be pressed until it is in its second position 150, e.g., in which the bottom of the well provides sufficient resistance to move the second portion 106 to its second position 150). The second position 150 can be located closer to the closed end 105 of the first portion 104 of the biological sterilization indicator 100 than the first position 148.

As shown in the illustrated embodiment, in some embodiments, the first portion 104 of the housing 102 can include a step, overhang, or flat-to-round transition 152. The step 152 is shown as being exposed when the second portion 106 is in its first position 148 and as being obscured or covered when the second portion 106 is in its second position 150. As such, the step 152 can be detected to determine whether the second portion 106 is in the first position 148 (i.e., the biological sterilization indicator 100 is unactivated), or is in the second position 150 (i.e., the biological sterilization indicator 100 is activated). Using such features of the biological sterilization indicator 100 to determine a status of the biological sterilization indicator 100, for example, to confirm whether the biological sterilization indicator 100 has been activated, is described in greater detail in U.S. Publication No. 2013/0217107. The longitudinal position of the step 152 is shown by way of example only; however, it should be understood that the step 152 can instead be located at a different longitudinal position (e.g., closer to the closed end 105 of the biological sterilization indicator 100), or, in some embodiments, the transition from a rounded portion to a flat face can be gradual, tapered, or ramped.

A variety of coupling means can be employed between the first portion 104 and the second portion 106 of the housing 102 to allow the first portion 104 and the second portion 106 to be removably coupled to one another, including, but not limited to, gravity (e.g., one component can be set atop another component, or a mating portion thereof), screw threads, press-fit engagement (also sometimes referred to as "friction-fit engagement" or "interference-fit engagement"), snap-fit engagement, magnets, adhesives, heat sealing, other suitable removable coupling means, and combinations thereof. In some embodiments, the biological sterilization indicator 100 need not be reopened and the first portion 104 and the second portion 106 need not be removably coupled to one another, but rather can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. One of ordinary skill in the art will recognize that some of the permanent or semi-permanent coupling means can also be adapted to be removable, and vice versa, and are categorized in this way by way of example only.

As shown in FIGS. 4 and 6, the second portion 106 can be movable between a first longitudinal position 148 with respect to the first portion 104 and a second longitudinal position 150 with respect to the first portion 104; however, it should be understood that the biological sterilization indicator 100 could instead be configured differently, such that the first and second positions 148 and 150 are not necessarily longitudinal positions with respect to one or both of the first portion 104 and the second portion 106 of the housing 102.

The second portion 106 can further include a seal 156 (e.g., a projection, a protrusion, a flap, flange, o-ring, or the like, or combinations thereof) that can be positioned to contact the first end 101 of the first portion 104, and particularly, an open upper end 157 of the first portion 104 to close or seal (e.g., hermetically seal) the biological sterilization indicator 100 after the second portion 106 has been moved to the second position 150 and the liquid 122 has been released from the container 120 (i.e., when the container 120 is in a second, fractured, state). That is, the spores 115 can be sealed from ambience when the container 120 is in the second state. The seal 156 can take a variety of forms and is shown in FIGS. 4 and 6 by way of example as forming an inner ring or cavity that together with the wall 110 of the second portion 106 is dimensioned to receive the upper end 157 of the first portion 104 of the housing 102 to seal the biological sterilization indicator 100.

In some embodiments, one or both of the seal 156 and the upper end 157 can further include a structure (e.g., a protrusion) configured to engage the other of the upper end 157 and the seal 156, respectively, in order to couple the second portion 106 of the housing 102 to the first portion 104 of the housing 102.

In addition, in some embodiments, the second portion 106 of the housing 102 can be coupled to the first portion 104 of the housing 102 to seal the biological sterilization indicator 100 from ambience after activation. Such sealing can inhibit contamination, evaporation, or spilling of the liquid 122 after it has been released from the container 120, and/or can inhibit contamination of the interior of the biological sterilization indicator 100.

The seal 156 can be configured to have a length in the longitudinal direction $D_L$ of the biological sterilization indicator 100 to accommodate different degrees or levels of closure. That is, in some embodiments, the "second position" 150 of the second portion 106 of the housing 102 can be any position in which at least a portion of the seal 156 has engaged a portion (e.g., the upper end 157) of the first portion 104 of the housing 102 such that the interior of the biological sterilization indicator 100 is sealed from ambience. The biological sterilization indicator 100 and the biological sterilization indicator system 10 can correspondingly be configured such that if the reading apparatus 12 detects that the second portion 106 has moved to the second position 150, the user knows that the seal 156 is engaged.

The insert 130 will now be described in greater detail.

As shown in FIGS. 1-2 and 4, during sterilization and before activation, the second portion 106 can be in a first position 148 with respect to the first portion 104. In the first position 148, the container 120 can be held intact in a position separate from the lower portion 114, the second chamber 111, or the spores 115, and the liquid 122 can be contained within the container 120.

As shown in FIG. 6, after sterilization, the biological sterilization indicator 100 can be activated to release the liquid 122 from the container 120 to move the liquid 122 to the second chamber 111. That is, the second portion 106 of the housing 102 can be moved to a second position 150 with respect to the first portion 104. When the second portion 106 is moved from the first position 148 to the second position 150, the seal 156 of the second portion 106 of the housing 102 can engage the upper end 157 of the first portion 104 to seal the reservoir 103 of the biological sterilization indicator 100 from ambience. In such embodiments, the second portion 106 can reversibly engage the first portion 104 in the second position 150, and in some embodiments, the second portion 106 can irreversibly engage the first portion 104. However, it should be understood that the structures and coupling means for the first portion 104 and the second portion 106 are shown in illustrated embodiment by way of example only, and any of the above-described coupling means can instead be employed between the first portion 104 and the second portion 106 of the housing 102.

The insert 130 can be adapted to hold or carry the container 120, such that the container 120 is held intact in a location separate from the spores 115 during sterilization. That is, as mentioned above, in some embodiments, the insert 130 can include (or function as) a carrier 132 for the container 120, particularly, before the container 120 is broken during the activation step (i.e., the step in which the liquid 122 is released from the container 120 and introduced to the spores 115, which typically occurs after a sterilization process).

In addition, the insert 130 can be adapted to hold the container 120 intact in a position in the housing 102 that maintains at least a minimal spacing (e.g., a minimal cross-sectional area of space) between the container 120 and the housing 102 and/or between the container 120 and any other components or structures in the housing 102 (e.g., at least a portion of the insert 130, such as the carrier 132, etc.), for example, to maintain a substantially constant sterilant path 164 in the biological sterilization indicator 100. In some embodiments, the insert 130 can be adapted to hold the container 120 in a substantially consistent location in the housing 102.

In some embodiments, as shown in FIG. 3, at least a portion of the housing 102 can include a tapered portion 146 in which the housing 102 (e.g., the wall 108 and/or an inner surface thereof) generally tapers in the longitudinal direction $D_L$ of the housing 102. As a result, the cross-sectional area in the housing 102 can generally decrease along the longitudinal direction $D_L$.

In some cases, without providing the means to maintain at least a minimal spacing around the container 120 (e.g., between the container 120 and surrounding structure), there can be a possibility that the container 120 can become positioned in the housing 102 (e.g., in the tapered portion 146) in such a way that it obstructs or blocks the sterilant path 164. However, the biological sterilization indicator 100 of the present disclosure is designed to inhibit this from occurring. For example, in the illustrated embodiment, the insert 130 (and particularly, the carrier 132) can be configured to hold the container 120 out of the tapered portion 146 of the housing 102, such that at least a minimal cross-sectional area is maintained around the container 120 in any orientation of the biological sterilization indicator 100 prior to activation. For example, in the embodiment illustrated in FIGS. 1-5, even if the biological sterilization indicator 100 is tipped upside down, the container 120 may fall away from contact with the insert 130, but in no orientation, is the container 120 moved any closer to the tapered portion 146, or the spores 115 until activation of the biological sterilization indicator 100. In addition, until activation, at least a minimal spacing (and particularly, a cross-sectional area of that spacing) between the container 120 and the housing 102 and/or the insert 130 can be maintained to provide a substantially constant sterilant path 164, for example, around the container 120, through the first fluid path 160 and into the second chamber 111.

In some embodiments, the relative sizing and positioning of the components of the biological sterilization indicator 100 can be configured such that, before activation, the container 120 is held intact in a substantially consistent location in the biological sterilization indicator 100. Such a configuration can provide a substantially constant sterilant path 164 and can maintain the container 120 in a position such that the container 120 is not able to move substantially, if at all, in the biological sterilization indicator 100 before activation.

In some embodiments, at least a portion of the insert 130 can be adapted to allow the container 120 to move in the housing 102, e.g., longitudinally with respect to the housing 102, between a first (longitudinal) position in which the container 120 is intact and a second (longitudinal) position in which at least a portion of the container 120 is fractured. By way of example only, the insert 130 can include one or more projections or arms 158 (two projections 158 spaced about the container 120 are shown by way of example only) adapted to hold and support the container 120 before activation and to allow the container 120 to move in the housing 102 during activation, for example, when the second portion 106 is moved with respect to the first portion 104 of the housing 102. The projections 158 can also be adapted (e.g., shaped and/or positioned) to fracture the container 120 in a desired manner when the biological sterilization indicator is activated. As a result, the insert 130 can sometimes function to hold the container 120 intact before activation, and can function to break the container 120 during activation. As a result, the insert 130, or a portion thereof, can sometimes be referred to as a "carrier" (e.g., the carrier 132) and/or a "breaker."

By way of example only, the projections 158 are shown in FIGS. 1 and 3-7 as being coupled to a base or support 127 adapted to abut the separating wall 118. For example, the base 127 can be dimensioned to be received in the reservoir 103 and dimensioned to sit atop, abut, or otherwise cooperate with or be coupled to the separating wall 118. Such coupling with an internal structure of the biological sterilization indicator 100 can provide the necessary resistance and force to break the container 120 when desired. In some embodiments, however, the insert 130 does not include the base 127, and the projections 158 can be coupled to or form a portion of the housing 102. In some embodiments, the insert 130 is integrally formed with or provided by the housing 102.

As shown, the insert 130 can further include a sidewall 131 that connects the projections 158 and is shaped to accommodate an inner surface of the housing 102 and/or an outer surface of the container 120. Such a sidewall 131 can provide support and rigidity to the projections 158 to aid in reliably breaking the container 120 in a consistent manner. The sidewall 131 can also be shaped and dimensioned to guide the container 120 in a desired manner as it is moved in the housing 102 during activation, for example, to contact the projections 158 in a desired way to reliably fracture the container 120. The sidewall 131 and/or the wall 108 of the housing 102 (or an inner surface thereof) can also be shaped to define at least a portion of the second fluid path 162 of the biological sterilization indicator 100, for example, between an outer surface of the insert 130 and an inner surface of the housing 102. For example, in some embodiments, as shown in FIGS. 1-2, 5 and 7, the sidewall 131 of the insert 130 can include a channel (or groove, recess, or the like) 169 configured to form at least a portion of the second fluid path 162.

The second fluid path 162 can function as an "internal vent" or a "vent channel" within the biological sterilization indicator 100 to allow gas (e.g., displaced gas, such as air that had been trapped in the second chamber 111 (e.g., near the closed end 105 of the biological sterilization indicator 100) to escape the second chamber 111 of the biological sterilization indicator 100. In some embodiments, the second fluid path 162 can provide an escape, or internal vent, for a gas present in the second chamber 111 during activation to facilitate moving the liquid 122 into the second chamber 111 from the first chamber 109 as it is released from the container 120. Additionally or alternatively, in some embodiments, the second fluid path 162 can provide an escape, or internal vent, for a gas present in the second chamber 111 during sterilization to facilitate moving a sterilant into the second chamber 111 of the biological sterilization indicator 100 and to the spores 115, with more efficient sterilant penetration into the second chamber 111.

Figure 7:
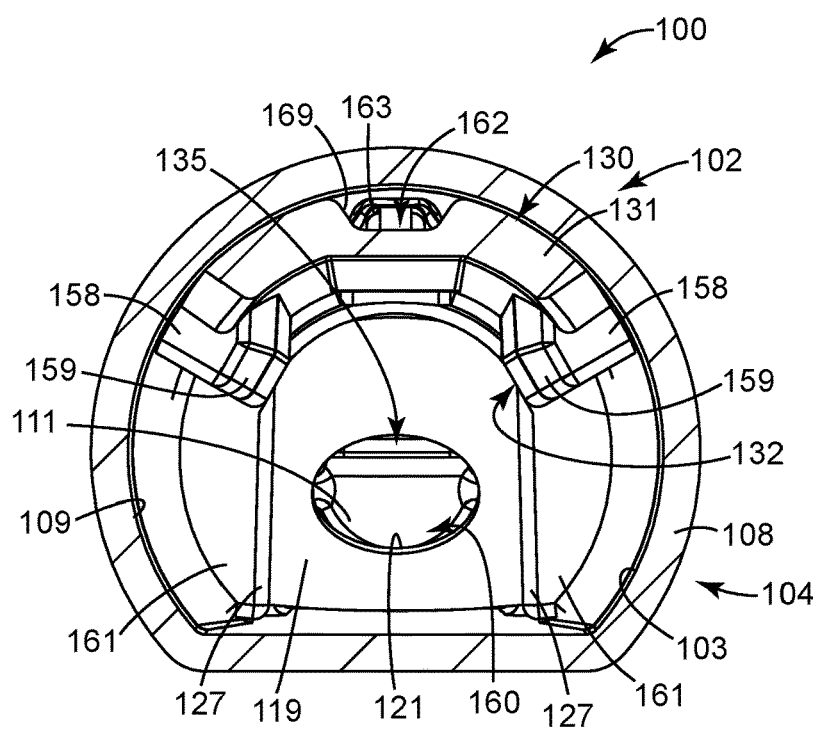
FIG. 7 is a top cross-sectional view of the biological sterilization indicator of FIGS. 1-6, with portions removed for clarity.

By way of example only, as shown in FIGS. 2 and 7, the second fluid path 162 can be at least partially defined by both a portion of the insert 130 (e.g., the channel 169) and by a channel (or groove, recess, or the like) 163 formed in the wall 108 of the housing 102 (e.g., in an inner surface of the wall 108). However, it should be understood that in some embodiments, the second fluid path 162 can be formed entirely of the housing 102 or of various combinations of other components of the biological sterilization indicator 100 such that the second fluid path 162 provides fluid connection between the second chamber 111 and another internal portion or region of the biological sterilization indicator 100. For example, the second fluid path 162 need not be formed by both the housing 102 and the insert 130, but can be formed by one of these components, or other components. In addition, as shown in FIGS. 2 and 7, the channel 163 that defines at least a portion of the second fluid path 162 is molded into an outer surface and an inner surface of the housing 102, such that the channel 163 is visible on the inside and the outside of the housing 102. However, the outer surface of the housing 102 need not include such a shape, and rather, in some embodiments, the outer surface of the housing 102 can remain substantially uniform or unchanged, and the inner surface of the housing 102 (e.g., a wall 108 of the housing 102) can include the channel 163.

Furthermore, in some embodiments, neither the insert 130 nor the housing 102 include the channel 169 or the channel 163, respectively, but rather the insert 130 and the housing 102 are shape and dimensioned such that a space or gap is provided between the insert 130 and the housing 102 that is in fluid communication with the second chamber 111, and such a space or gap functions as the second fluid path 162.

As further shown in FIGS. 4 and 6, in some embodiments, the first fluid path 160 and/or the second fluid path 162 can be at least partially defined by one or more of the wall 118, the substrate 119, the insert 130, and the housing 102. In addition, at least one of the first fluid path 160 and the second fluid path 162 can be defined at least partially by the spore carrier 135, or a portion thereof.

In some embodiments, the biological sterilization indicator 100 can include the following components arranged in the following order when the container 120 is in a first, unfractured, state: the closed end 105 of the housing 102 of the biological sterilization indicator 100, the second chamber 111, the substrate 119, the insert 130, the first chamber 109, the container 120, the open end 101 of the housing 102 (or the second portion 106 of the housing 102).

As shown in the illustrated embodiment, the second fluid path 162 can allow the second chamber 111 to vent to another portion of the biological sterilization indicator 100, such as the first chamber 109. In some embodiments, the second fluid path 162 can exit the second chamber 111 at a position located above (e.g., vertically above) the position at which the first fluid path 160 enters the second chamber 111, particularly, in embodiments in which the second fluid path 162 vents the second chamber 111 back to the first chamber 109. Said another way, in some embodiments, the second fluid path 162 can extend from the second chamber 111 to a position (e.g., a fourth level $L_4$, described below) in the biological sterilization indicator 100 that is above the position (e.g., a first level $L_1$ or a second level $L_2$, described below) at which the first fluid path 160 enters the second chamber 111. Furthermore, in some embodiments, the position at which the second fluid path 162 enters the first chamber 109 can be located above (e.g., vertically above) the position at which the first fluid path 160 enters the second chamber 111.

In some embodiments, the first fluid path 160 can be positioned to fluidly couple the second chamber 111 with a proximal portion of the biological sterilization indicator 100 (e.g., a portion of the first chamber 109 that is located proximally or adjacent the second chamber 111, e.g., at the first level $L_1$ and/or the second level $L_2$), and the second fluid path 162 can be positioned to fluidly couple the second chamber 111 with a distal portion of the biological sterilization indicator 100 (i.e., a portion of the first chamber 109 that is located further from the second chamber 111, e.g., at a third level $L_3$, described below, and/or the fourth level $L_4$). As a result, the position at which the second fluid path 162 enters the first chamber 109 can be positioned further from the second chamber 111 than the position at which the first fluid path 160 enters the second chamber 111.

More specifically and by way of example only, with reference to FIGS. 4 and 6, in some embodiments, fluid can enter the second chamber 111 at a variety of locations, such as at the first level, height, or position (e.g., longitudinal position) $L_1$ located generally at the front of the insert 130, the substrate 119, the housing 102, and/or the second chamber 111, as well as at the second level, height, or position (e.g., longitudinal position) $L_2$ located approximately at the level of the aperture 121 in the substrate 119. As described above, it should be understood that the variety of opening and spaces between the first chamber 109 and the second chamber 111 that allow fluid to move into the second chamber 111 can collectively be referred to as the first fluid path 160. As further illustrated in FIG. 4, in some embodiments, gas (e.g., displaced gas) can exit the second chamber 111 via the second fluid path 162 (i.e., as fluid moves into the second chamber 111 via the first fluid path 160) at the third level, height, or position (e.g., longitudinal position) $L_3$ located generally at the back of the insert 130, the substrate 119, the housing 102, and/or the second chamber 111.

In the vertically upright orientation of the biological sterilization indicator 100 shown in FIGS. 4 and 6, the third level $L_3$ is located at or above both the first level $L_1$ and the second level $L_2$. In addition, in some embodiments, the third level $L_3$ can still be located at or above both the first level $L_1$ and the second level $L_2$ in operation of the biological sterilization indicator 100 (e.g., when seated in a well of a reading apparatus, during sterilization, and/or during activation). That is, in some embodiments, the biological sterilization indicator 100 can be tilted in operation (e.g., toward the left-hand side of FIG. 4 or 6, toward the right-hand side of FIG. 4 or 6, into the page of FIG. 4 or 6, and/or out of the page of FIG. 4 or 6).

The first, second, and third levels $L_1$, $L_2$, and $L_3$ are shown by way of example only; however, it should be understood that the exact location at which the first fluid path 160 enters the second chamber 111 and/or the exact location at which the second fluid path 162 exits the second chamber 111 can be different than what is illustrated in FIGS. 4 and 6.

As shown in FIGS. 4 and 6, the second fluid path 162 is at least partially defined by the channel 169 of the insert 130 and/or the channel 163 of the housing 102, which will generally be referred to as simply "the channel" in the following discussion, which can be interpreted to refer to at least a portion of the channel 163 and/or the channel 169 of the illustrated embodiment. In the illustrated embodiment, the channel has an entrance that can be described as being located at any point in the second chamber 111, or at the third level $L_3$, and an exit that is positioned generally at the fourth level, height, or position (e.g., longitudinal position) $L_4$. As shown in FIGS. 4 and 6, the exit position of the channel (i.e., the fourth level $L_4$) is generally located above the position at which the first fluid path 160 connects with the second chamber 111 (i.e., the first level $L_1$ and/or the second level $L_2$), for example, in operation of the biological sterilization indicator 100.

Said another way, the first fluid path 160 can be positioned to fluidly couple the second (lower) end 113 of the first chamber 109 to the first (upper) end 124 of the second chamber 111. The second fluid path 162, on the other hand, can be positioned to fluidly couple the second chamber 111 (e.g., the first (upper) end 124 of the second chamber 111) to an upper portion (e.g., the first (upper) end 112) of the first chamber 109.

Furthermore, in some embodiments, the position or level at which the second fluid path 162 (or the channel) connects with the second chamber 111 can be described as being located at portion of the second chamber 111 that is the last to fill with the liquid 122 when the container 120 is in its second, fractured, state.

In some embodiments, when the container 120 is in the second, fractured, state, and the second chamber 111 is at least partially filled with the liquid 122, the liquid 122 can have a level, height or position (e.g., longitudinal position) L, and the second fluid path 162 can extend between a position below the level L and a position above the level L. As a result, as the second chamber 111 fills with the liquid 122 when the container is in the second state, the second chamber 111 can continually be vented by the second fluid path 162.

In some embodiments, the first fluid path 160 can function as the main or primary fluid communication path between the first chamber 109 and the second chamber 111, and the second fluid path 162 can serve as an accessory or secondary fluid communication path between the second chamber 111 and the first chamber 109 (e.g., when the second fluid path 162 exits in the first chamber 109 and not another portion of the biological sterilization indicator 100). In such embodiments, the collective space, volume and/or area of the second fluid path 162 can be substantially less than that of the first fluid path 160. In some embodiments, at least a portion of the first fluid path 160 and the second fluid path 162 can be described as being substantially isolated from one another or as being substantially parallel and non-intersecting. In some embodiments, the first fluid path 160 and the second fluid path 162 can each extend substantially longitudinally (e.g., substantially parallel to the longitudinal direction $D_L$) between the first chamber 109 and the second chamber 111.

That is, generally, the biological sterilization indicator 100 that includes (1) a first fluid path, such as the first fluid path 160, configured to accommodate at least a majority of the fluid movement from the first chamber 109 to the second chamber 111, and (2) a second fluid path, such as the second fluid path 162, configured to vent gas from the second chamber 111 would have advantages over a biological sterilization indicator 100 that included either only one internal chamber, or only one fluid path connecting the first chamber 109 and the second chamber 111, such that gas would have to exit the second chamber 111 via the same fluid path that fluid enters the second chamber 111.

By configuring the first fluid path 160 and the second fluid path 162 as shown in the illustrated embodiment, in some embodiments, the biological sterilization indicator 100 can at least partially eliminate any air-lock effect that may occur as a result of trying to move a sterilant and/or the liquid 122 into the second chamber 111. In addition, in some embodiments, the second fluid path 162 can allow for the biological sterilization indicator 100 to be activated, and the liquid 122 to be moved into the second chamber 111 due to gravity, while the biological sterilization indicator 100 remains in the same orientation (e.g., a substantially vertically upright orientation, as shown in FIGS. 1-2, 4 and 6), without requiring that the biological sterilization indicator 100 to be tipped upside down, or otherwise re-oriented in order to move the liquid 122 into the second chamber 111.

With continued reference to the insert 130, the projections 158 of the insert 130 are illustrated as being relatively rigid and stationary. That is, in some embodiments, the projections 158 may not be adapted to substantially flex, distort, deform or otherwise heed to the container 120 as it is moved in the housing 102. Rather, in some embodiments, as shown in FIGS. 1-4 and 6, the projections 158 can each be configured to have an upper end 159 atop which the container 120 can be positioned and held intact before activation. As shown in FIGS. 1-2 and 4, in some embodiments, the projections 158 can be positioned to fracture the container 120 at its radiused end, for example, when an oblong or capsule-shaped container 120 is employed.

One potential advantage of having the projections 158 form at least a portion of the carrier 132 is that the bottom of the container 120 can be unrestricted when the container 120 is fractured, such that the liquid 122 can be released from the container 120 and moved toward the spores 115 with relative ease and reliability.

In such embodiments, the insert 130 can be used to fracture the container 120 in a direction that is substantially perpendicular to a flat side of the container 120, for example, when an oblong or capsule-shaped container 120 is employed. In such embodiments, fracturing the container 120 along its side can be achieved, along with maintaining some open spaces around the lower end of the container 120 to facilitate moving the liquid 122 from the container 120 to the proximity of the spores 115 when the container 120 is fractured.

As mentioned above, the projections 158 can be adapted to fracture the container 120 as the container 120 is moved with respect to the housing 102 (e.g., along the longitudinal direction $D_L$), for example, in response to the second portion 106 of the housing 102 being moved with respect to the first portion 104 of the housing 102 (e.g., from the first position 148 to the second position 150).

In some embodiments, the projections 158 can include one or more edges (e.g., tapered edges) or points or otherwise be configured to concentrate the crushing force to increase the pressure on the container 120 in the regions adjacent the projections 158, and to facilitate fracturing the container 120 more easily and in one or more desired regions. In some embodiments, such concentration of force can reduce the total effort or force needed to move the second portion 106 with respect to the first portion 104 and to fracture the container 120 (or a portion thereof).

As shown in FIGS. 1-4 and 6, the projections 158 are integrally formed with the base 127 of the insert 130; however, it should be understood that the projections 158 can instead be integrally formed with the wall 108 of the housing 102. In addition, in some embodiments, the projections 158 can be coupled to the housing 102, or the projections 158 and the base 127 can be provided by separate inserts. In such embodiments, the projections 158 can each be a separate insert, or multiple projections 158 can be provided by one or more inserts. In addition, the insert 130 can be configured to abut the wall 118 to inhibit movement of the first portion the insert 130 into the proximity of the spores 115 (e.g., the lower portion 114 of the housing 102).

In addition, in some embodiments, as shown in FIGS. 1-4 and 6, the projections 158 can extend a distance along the longitudinal direction $D_L$, and the length and/or thickness (e.g., which can vary along the length) of the projections 158 can be tailored to control the fracturing of the container 120 at a desired position in the housing 102 and in a desired manner. The configuration of the projections 158 is shown in FIGS. 1-7 by way of example only.

In general, each of the projections 158 is shown by way of example only as increasing in thickness (e.g., inwardly toward the container 120 or center of the housing 102) along the longitudinal direction $D_L$ toward the spores 115. Such a configuration can decrease the cross-sectional area that is available to the container 120, as the container 120 is moved toward the spores 115, for example, in response to the second portion 106 being moved to the second position 150.

Furthermore, the biological sterilization indicator 100 is shown in FIGS. 1-7 as including two projections 158 and a sidewall 131 by way of example only, but it should understood that one projection 158 or as many as structurally possible, and other configurations, can be employed. In addition, the projections 158 can be shaped and dimensioned as desired, depending on the shape and dimensions of the housing 102, on the shape and dimensions of the container 120, on the shape and dimensions of the insert 130, and/or on the manner and position desired for fracturing the container 120.

As mentioned above, in some embodiments, at least a portion of the housing 102 can be tapered (see, e.g., the tapered portion 146 in FIG. 3). As a result, the cross-sectional area in the housing 102 can generally decrease along the longitudinal direction $D_L$. However, it should be understood that the inner dimensions of the housing 102 can generally decrease in the tapered portion along the longitudinal direction $D_L$ without the outer dimensions of the housing 102 changing. In some embodiments, the outer dimensions of the housing 102 can be uniform along its length, even though the inner portion of the housing 102 tapers along its length. In some embodiments, the one or more projections 158 alone can vary in thickness (i.e., toward the container 120, e.g., in a radial direction) along the longitudinal direction $D_L$, such that the cross-sectional area available to the container 120 generally decreases as the container 120 is moved in the housing 102 during activation, even though the dimensions of the housing 102 do not change (e.g., even if the housing 102 does not include any tapered portion 146, either internally or externally).

As shown in FIGS. 1-7, the upper end 159 of each of the projections 158 includes a rounded, curved or arcuate surface, which can facilitate movement of the container 120 from the first position 148 in which the container 120 sits at least partially above the upper end 159 of the projection 158 to a position in which the container 120 is forced, at least partially, into the smaller cross-sectional area region in between the projections 158 (or between the wall 108 of the housing 102 and one or more projections 158). In addition, the rounded upper end 159 can inhibit premature breakage of the container 120, which can inhibit premature activation of the biological sterilization indicator 100 (i.e., premature release of the liquid 122).

In some embodiments, as shown in FIG. 3, the insert 130 can be sized and shaped to allow the container 120 to be held above the projections 158 and out from the region adjacent any portion of an inwardly-facing surface of one or more of the projections 158 to inhibit accidental or premature activation of the biological sterilization indicator 100. Such a configuration can also inhibit inadvertent breakage due to shock or material expansion (e.g., due to exposure to heat during a sterilization process).

The carrier 132, which can be formed at least partially by the upper ends 159 of the projections 158, can be configured to hold a bottom portion of the container 120, and the projections 158 can be positioned to fracture the container 120 at a location near the bottom of the container 120 as it is positioned in the housing 102. Such a configuration can allow the container 120 to be broken near its bottom and can facilitate removal of the liquid 122 from the container 120, which can enhance the availability of the liquid 122 to the spores 115, and can enhance the reliability of releasing the liquid 122 into fluid communication with the spores 115

(e.g., with the spore reservoir 136). Such a configuration is shown by way of example only, however, and it should be understood that the projections 158 can be configured and positioned to fracture the container 120 in any desired manner.

Some embodiments of the present disclosure provide optimal and safe breakage of a frangible container 120 with relatively low force, while enhancing transfer of liquid 122 to the spore region (e.g., the second chamber 111 of the housing 102) of the biological sterilization indicator 100, and/or enhancing containment of the liquid 122 in the spore region of the biological sterilization indicator 100. In addition, some embodiments of the present disclosure operate to drive a liquid to a particular area of the biological sterilization indicator 100, such as a detection chamber (e.g., the second chamber 111) of the biological sterilization indicator 100.

In the embodiment illustrated in FIGS. 1-7, the insert 130 is illustrated as including two projections 158 that are approximately equally spaced about the container 120 and/ or about the sidewall 131. However, in some embodiments, the sidewall 131 can include one solid (e.g., substantially annular or semi-annular) projection 158 that extends radially inwardly from the sidewall 131. Furthermore, in some embodiments, the sidewall 131 can extend further around the inner surface of the housing 102 than what is illustrated. However, employing one or more narrower (e.g., in an angular dimension) projections 158, such as those shown in FIGS. 1-7, can provide a substantially constant or substantially unobstructed sterilant path 164 around the container 120.

Whether the insert 130 includes one or more projections 158 or sidewalls 131, the insert 130 can be configured to hold the container 120 in the housing 102 in a consistent location to provide a substantially constant sterilant path 164 during sterilization. For example, rather than allowing the container 120 to move or roll around (e.g., radially and/or longitudinally) in the housing 102 before activation (e.g., during sterilization), the insert 130 can hold the container 120 in a substantially consistent position, which can allow a sterilant a substantially consistent and relatively unobstructed path between an outer surface of the container 120 and an inner surface of the housing 102, with little or no opportunity for inadvertent blockage.

As shown in the illustrated embodiment, the insert 130 can further include one or more projections 161 positioned substantially horizontally or perpendicularly with respect to the longitudinal direction $D_L$ of a biological sterilization indicator (e.g., when the insert 130 is positioned in a biological sterilization indicator). The projections 161 can be referred to as "second projections" or "horizontal projections," while the projections 158 used to hold and/or break the container 120 can be referred to as "first projections" or "vertical projections." The second projections 161 are not angled downwardly like the base 127. As a result, the second projections 161 can be used for a variety of purposes. For example, the second projections 161 can stabilize the insert 130 (e.g., aid in holding the insert 130 in a desired position in the housing 102 of the biological sterilization indicator 100) under the force of fracturing the container 120. In addition, the second projections 161 can function to retain and/or collect fractured portions of the container 120 after it has been fractured to inhibit movement of such portions into the proximity of spores in the biological sterilization indicator, which could negatively affect spore growth and/or detection of spore growth. Other shapes and configurations of the second projections 161 can be employed that still allow for fluid movement down to the spores 115 while inhibiting solid movement down to the spores 115.

In some embodiments, the insert 130 (e.g., the base 127) can be adapted for one or more of facilitating or allowing fluid movement (e.g., movement of the liquid 122) into the second chamber 111 (i.e., the lower portion 114) of the housing 102; minimizing movement of fractions or portions (e.g., solids) of the fractured container 120 into the second chamber 111 of the housing 102, that is, collecting and/or retaining portions of the fractured container 120; and/or minimizing diffusion of the spores 115 and/or signals out of the second chamber 111 of the housing 102. For example, in some embodiments, the base 127 can be configured to function as a grate or filter. In some embodiments, spore growth is determined by fluorescent indicators/molecules (e.g., fluorophores) or other markers. In some embodiments, if the liquid level after activation in the biological sterilization indicator 100 is above the location of the spores 115, such molecules or markers, or the spores 115 themselves, can move or diffuse away from or out of the spore reservoir 136 and, potentially, out of the second chamber 111 of the housing 102. As a result, portions of the biological sterilization indicator 100 (e.g., the insert 130) can be configured to inhibit undesirable diffusion of various indicators, molecules, and/or markers out of the second chamber 111 of the biological sterilization indicator 100. In some embodiments, as described above, the substrate 119 can also inhibit such undesirable diffusion.

In the embodiment illustrated in FIGS. 1-4, the base 127 of the insert 130 is generally U-shaped or horseshoe-shaped and includes a central aperture 177 (see FIG. 2) that facilitates the movement of sterilant toward the spores 115 during sterilization and the movement of the liquid 122 toward the spores 115 during activation. The horseshoe shape of the base 127 can increase the opening between the upper portion 116 (i.e., the first chamber 109) and the lower portion 114 (i.e., the second chamber 111) of the housing 102; however, this shape is shown by way of example only, and other shapes can be employed.

In some embodiments, the insert 130 can be described as including one or more downwardly-extending projections 127 adapted to abut or otherwise couple to the wall 118 or another internal structure of the biological sterilization indicator 100 to provide a base or support for the insert 130, to inhibit movement of the insert 130 and container 120 relative to the housing 102 before activation, and/or to provide resistance or force to aid in breaking the container 120 during activation. As a result, in some embodiments, the base 127 can instead be referred to as "third projections" 127.

As shown in the illustrated embodiment, in some embodiments, the insert 130 can be configured to reside entirely in the first chamber 109 of the biological sterilization indicator 100, such that the insert 130 does not extend into the second chamber 111 where it could potentially interfere with interrogation or detection processes. Furthermore, the insert 130 can be configured to inhibit movement of other portions of the biological sterilization indicator 100 (e.g., the fractured container 120) into the second chamber 111.

The insert 130 of the illustrated embodiment is generally symmetrical about a central longitudinal line of symmetry, such that there are two identical first projections 158, two identical second projections 161, and two identical third projections 127. However, the insert 130 need not include any lines of symmetry, and the first projections 158 need not be the same as one another, the second projections 161 need not be the same as one another, and the third projections 127 need not be the same as one another. The insert 130, and the various projections 158, 161 and 127 can be sized and positioned to control the sterilant path 164, for example, to tailor the kill/survival rate of the biological sterilization indicator 100, to inhibit inadvertent fracture of the container 120, to facilitate movement of the container 120 in the housing 120, to mate with or engage the housing 102, and/or to control the breakage of the container 120.

By way of example only, the illustrated insert 130 is shown as being a unitary device that includes at least the following: means for holding the container 120 before activation, for fracturing the container 120 during activation; for allowing movement of the container 120 in the housing 102; for providing a substantially constant sterilant path 164, for collecting and/or retaining portions of the fractured container 120 after activation (or at least partially inhibiting movement of portions of the fractured container 120 into the second chamber 111 of the housing 102); and/or for minimizing diffusion of the spores 115 and/or signals from the second chamber 111 to the first chamber 109 of the housing 102 after activation. However, it should be understood that in some embodiments, the insert 130 can include multiple portions that may not be part of a single, unitary device, and each of the portions can be adapted to do one or more of the above functions.

The insert 130 is referred to as an "insert" because in the illustrated embodiment, the device that performs the above functions is a device that can be inserted into the reservoir 103 (and, particularly, the first chamber 109) of the housing 102. However, it should be understood that the insert 130 can instead be provided by the housing 102 itself or another component of the biological sterilization indicator 100 and need not necessarily be insertable into the housing 102. The term "insert" will be described throughout the present disclosure for simplicity, but it should be understood that such a term is not intended to be limiting, and it should be appreciated that other equivalent structures that perform one or more of the above functions can be used instead of, or in combination with, the insertable insert 130. Furthermore, in the illustrated embodiment, the insert 130 is both insertable into and removable from the housing 102, and particularly, into and out of the first portion 104 (and the first chamber 109) of the housing 102. However, it should be understood that even if the insert 130 is insertable into the housing 102, the insert 130 need not be removable from the housing 102, but rather can be fixedly coupled to the housing 102 in a manner that inhibits removal of the insert 130 from the housing 102 after positioning the insert 130 in a desired location.

In some embodiments, at least a portion of the housing 102, for example, the lower portion 114 of the housing 102, can be transparent to an electromagnetic radiation wavelength or range of wavelengths (e.g., transparent to visible light when visible-light optical detection methods are employed), which can facilitate detection of spore growth. That is, in some embodiments, as shown in FIGS. 3, 4 and 6, at least a portion of the housing 102 can include or form a detection window 167.

In addition, in some embodiments, as shown in FIG. 3, at least a portion of the housing 102, for example, the lower portion 114 can include one or more planar walls 168. Such planar walls 168 can facilitate detection (e.g., optical detection) of spore growth. In addition, as shown and described above, the wall 108 of the first portion 104 of the housing 102 can include one or more stepped or tapered regions, such as the step 152, the step 123, and a tapered wall, or step, 170. The tapered wall 170 can function to reduce the overall thickness and size of the lower portion, or detection portion, 114 of the housing 102, such that the outer dimensions of the housing 102 are reduced in addition to the inner dimensions. Such a reduction in size and/or thickness of the lower portion 114 of the biological sterilization indicator 100 can facilitate detection. In addition, having one or more features, such as the steps and/or tapered walls 123, 152, 170 can allow the biological sterilization indicator 100 to be coupled to a reader or detection device in only one orientation, such that the biological sterilization indicator 100 is "keyed" with respect to a reading apparatus, which can minimize user error and enhance reliability of a detection process. In some embodiments, one or more portions of the biological sterilization indicator 100 can be keyed with respect to a reading apparatus.

The biological sterilization indicator of the present disclosure generally keeps the liquid 122 and the spores 115 separate but in relatively close proximity (e.g., within the self-contained biological sterilization indicator 100) during sterilization, such that the liquid 122 and the spores 115 can be readily combined after exposure to a sterilization process. The liquid 122 and the spores 115 can be incubated during a detection process (e.g., the reading apparatus 12 can incubate the biological sterilization indicator 100), or the biological sterilization indicator 100 can be incubated prior to a detection process. In some embodiments, when incubating the spores with the liquid 122, an incubation temperature above room temperature can be used. For example, in some embodiments, the incubation temperature is at least about 37° C., in some embodiments, the incubation temperature is at least about 50° C. (e.g., 56° C.), and in some embodiments, at least about 60° C. In some embodiments, the incubation temperature is no greater than about 60° C., in some embodiments, no greater than about 50° C., and in some embodiments, no greater than about 40° C.

A detection process can be adapted to detect a detectable change from the spores 115 (e.g., from within the spore reservoir 136) or the liquid 122 surrounding the spores 115. That is, a detection process can be adapted to detect a variety of characteristics, including, but not limited to, electromagnetic radiation (e.g., in the ultraviolet, visible, and/or infrared bands), fluorescence, luminescence, light scattering, electronic properties (e.g., conductance, impedance, or the like, or combinations thereof), turbidity, absorption, Raman spectroscopy, ellipsometry, or the like, or a combination thereof. Detection of such characteristics can be carried out by one or more of a fluorimeter, a spectrophotometer, colorimeter, or the like, or combinations thereof. In some embodiments, such as embodiments that measure fluorescence, visible light, etc., the detectable change is measured by detecting at a particular wavelength.

The spores and/or the liquid 122 can be adapted (e.g., labeled) to produce one or more of the above characteristics as a result of a biochemical reaction that is a sign of spore viability. As a result, no detectable change (e.g., as compared to a baseline or background reading) can signify an effective sterilization process, whereas a detectable change can signify an ineffective sterilization process. In some embodiments, the detectable change can include a rate at which one or more of the above characteristics is changing (e.g., increasing fluorescence, decreasing turbidity, etc.).

In some embodiments, spore viability can be determined by exploiting enzyme activity. As described in Matner et al., U.S. Pat. No. 5,073,488, entitled "Rapid Method for Determining Efficacy of a Sterilization Cycle and Rapid Read-out Biological Indicator," which is incorporated herein by reference, enzymes can be identified for a particular type of spore in which the enzyme has particularly useful characteristics that can be exploited to determine the efficacy of a sterilization process. Such characteristics can include the following: (1) the enzyme, when subjected to sterilization conditions which would be sufficient to decrease a population of $1 \times 10^6$ test microorganisms by about 6 logs (i.e., to a population of about zero as measured by lack of outgrowth of the test microorganisms), has a residual activity which is equal to "background" as measured by reaction with a substrate system for the enzyme; and (2) the enzyme, when subjected to sterilization conditions sufficient only to decrease the population of $1 \times 10^6$ test microorganisms by at least 1 log, but less than 6 logs, has enzyme activity greater than "background" as measured by reaction with the enzyme substrate system. The enzyme substrate system can include a substance, or mixture of substances, which is acted upon by the enzyme to produce a detectable enzyme-modified product, as evident by a detectable change.

In some embodiments, the biological sterilization indicator 100 can be assayed in a single-side mode, where the biological sterilization indicator 100 includes only one detection window (e.g., detection window 167 of FIG. 3) that is positioned, for example, near the spores 115. In some embodiments, however, the biological sterilization indicator 100 can include more than one detection window (e.g., a window formed by all or a portion of both parallel walls 168 of the lower portion 114 of the housing 102), such that the biological sterilization indicator 100 can be assayed via more than one detection window. In embodiments employing multiple detection windows, the detection windows can be positioned side-by-side (similar to a single-side mode), or the detection windows can be oriented at an angle (e.g., 90 degrees, 180 degrees, etc.) with respect to one another.

In general, the spores 115 are positioned within the spore reservoir 136 which is in fluid communication with the reservoir 103. In some embodiments, the spore reservoir 136 forms a portion of the reservoir 103 (e.g., a portion of the second chamber 111). As shown in FIG. 4, the reservoir 103 is in fluid communication with ambience (e.g., via the aperture 107) during sterilization to allow sterilant to enter the reservoir 103 during a sterilization process to sterilize the spores 115. The container 120 can be configured to contain the liquid 122 during sterilization to inhibit the liquid 122 from being in fluid communication with the spores 115, the reservoir 103, and the sterilant during sterilization.

Various details of the spores 115 and/or spore reservoir 136 will now be described in greater detail.

In some embodiments, the spores 115 can be positioned directly in the lower portion 114 of the housing 102, or the spores 115 can be positioned in a spore reservoir, such as the spore reservoir 136 (e.g., provided by the spore carrier 135). Whether the spores 115 are positioned directly in the lower portion 114 of the housing 102 or in a spore reservoir, the spores 115 can be provided in a variety of ways. In some embodiments, the spores 115 can be in a spore suspension that can be positioned in a desired location in the biological sterilization indicator 100 and dried down. In some embodiments, the spores 115 can be provided on a substrate (not shown) that can be positioned and/or secured in a desired location in the biological sterilization indicator 100. Some embodiments can include a combination of spores 115 provided in a dried down form and spores 115 provided on a substrate.

In some embodiments, the substrate can be positioned to support the spores 115 and/or to help maintain the spores 115 in a desired locus. Such a substrate can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a reflective material (e.g., a metal foil), a glass, a porcelain, a ceramic, a gel-forming material (e.g., guar gum), or combinations thereof. In addition, or alternatively, such a substrate can include or be coupled to a hydrophilic coating to facilitate bringing the liquid 122 into intimate contact with the spores 115 (e.g., when the liquid 122 employed is aqueous). In addition, or alternatively, such a hydrophilic coating can be applied to any fluid path positioned to fluidly couple the liquid 122 and the spores 115. In some embodiments, in addition to, or in lieu of a hydrophilic coating, a hydrophobic coating can be applied to other portions of the housing 102 (e.g., the lower portion 114 of the housing 102) and/or spore reservoir 136, such that the liquid 122 is preferentially moved into contact with the spores 115.

Some embodiments of the biological sterilization indicator 100 do not include the spore carrier 135. Rather, the spore reservoir 136 is provided by the lower portion 114 of the housing 102 itself, and the spores 115 can be positioned in the lower portion 114, adsorbed to an inner surface or wall of the lower portion 114, or combinations thereof. In some embodiments, the spores 115 can be provided on a substrate that is positioned in the lower portion 114 of the housing 102.

In some embodiments, the spores 115 can be positioned in one locus of spores or in a plurality of loci of spores, all of which can be positioned either in the reservoir 103, in the lower portion 114 of the housing 102, and/or in the spore reservoir 136. In some embodiments, having multiple loci of spores can maximize the exposure of the spores to sterilant and to the liquid 122, can improve manufacturing (e.g., placement of the spores can be facilitated by placing each locus of spores in a depression within the biological sterilization indicator 100), and can improve detection characteristics (e.g., because spores in the middle of one large locus of spores may not be as easily detected). In embodiments employing a plurality of loci of spores, each locus of spores can include a different, known number of spores, and/or each locus of spores can include different spores, such that a plurality of spore types can be tested. By employing multiple types of spores, the biological sterilization indicator 100 can be used for a variety of sterilization processes and a specific locus of spores can be analyzed for a specific sterilization process, or the multiple types of spores can be used to further test the effectiveness, or confidence, of a sterilization process.

In addition, in some embodiments, the biological sterilization indicator 100 can include a plurality of spore reservoirs 136, and each spore reservoir 136 can include one or more loci of spores 115. In some embodiments employing a plurality of spore reservoirs 136, the plurality of spore reservoirs 136 can be positioned in fluid communication with the reservoir 103.

In some embodiments, the spores 115 can be covered with a cover (not shown) adapted to fit in or over the spores 115 and/or the spore reservoir 136. Such a cover can help maintain the spores within the desired region of the biological sterilization indicator 100 during manufacturing, sterilization and/or use. The cover, if employed, can be formed of a material that does not substantially impede a detection process, and/or which is at least partially transmissive to electromagnetic radiation wavelengths of interest. In addition, depending on the material makeup of the cover, in some embodiments, the cover can facilitate wicking the liquid 122 (e.g., the nutrient medium) along the spores 115. In some embodiments, the cover can also contain features for facilitating fluid flow into the spore reservoir 136 (or to the spores 115), such as capillary channels, hydrophilic microporous fibers or membranes, or the like, or a combination thereof. In addition, in some embodiments, the cover can isolate a signal, or enhance the signal, which can facilitate detection. Such a cover can be employed whether the spores 115 are positioned within the spore reservoir 136 or directly in the lower portion 114 of the housing 102. In addition, such a cover can be employed in embodiments employing a plurality of loci of spores. The cover can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a glass, a porcelain, a ceramic, a gel-forming material (e.g., guar gum), or combinations thereof.

In some embodiments, the biological sterilization indicator 100 can further include a modified inner surface, such as a reflective surface, a white surface, a black surface, or another surface modification suitable to optimize the optical properties of the surface. A reflective surface (e.g., provided by a metal foil) can be positioned to reflect a signal sent into the spore reservoir 136 from an assaying or detection device and/or to reflect any signal generated within the spore reservoir 136 back toward the assaying device. As a result, the reflective surface can function to improve (e.g., improve the intensity of) a signal from the biological sterilization indicator 100. Such a reflective surface can be provided by an inner surface of the housing 102; a material coupled to the inner surface of the housing 102; an inner surface the spore reservoir 136; a material coupled to the inner surface of the spore reservoir 136; or the like; or the reflective surface can form a portion of or be coupled to a spore substrate; or a combination thereof.

Similarly, in some embodiments, the biological sterilization indicator 100 can further include a white and/or black surface positioned to increase and/or decrease a particular signal sent into the spore reservoir 136 from an assaying device and/or to increase and/or decrease a particular signal generated within the spore reservoir 136. By way of example only, a white surface can be used to enhance a signal, and a black surface can be used to reduce a signal (e.g., noise).

In some embodiments, the spores 115 can be positioned on a functionalized surface to promote the immobilization of the spores 115 on the desired surface. For example, such a functionalized surface can be provided by an inner surface of the housing 102, an inner surface of the spore reservoir 136, can form a portion of or be coupled to a spore substrate, or the like, or a combination thereof.

In some embodiments, the spores 115 are positioned (e.g. applied by coating or another application method) on a microstructured or microreplicated surface (e.g., such microstructured surfaces as those disclosed in Halverson et al., PCT Publication No. WO 2007/070310, Hanschen et al., US. Publication No. US 2003/0235677, and Graham et al., PCT Publication No. WO 2004/000569, all of which are incorporated herein by reference). For example, such a microstructured surface can be provided by an inner surface of the housing 102, can be provided by an inner surface of the spore reservoir 136, can form a portion of or be coupled to a spore substrate, or the like, or a combination thereof.

In some embodiments, the biological sterilization indicator 100 can further include a gel-forming material positioned to be combined with the spores 115 and the liquid 122 when the liquid 122 is released from the container 120. For example, the gel-forming material can be positioned near the spores 115 (e.g., in the spore reservoir 136), in the lower portion 114 of the housing 102, can form a portion of or be coupled to a spore substrate, or the like, or a combination thereof. Such a gel-forming material can form a gel (e.g., a hydrogel) or a matrix comprising the spores and nutrients when the liquid 122 comes into contact with the spores. A gel-forming material (e.g., guar gum) can be particularly useful because it has the ability to form a gel upon hydration, it can aid in localizing a signal (e.g., fluorescence), it can anchor the spores 115 in place, it can help minimize diffusion of the spores 115 and/or a signal from the spore reservoir 136, and/or it can enhance detection.

In some embodiments, the biological sterilization indicator 100 can further include an absorbent or a wicking material. For example, the wicking material can be positioned near the spores 115 (e.g., in the spore reservoir 136), can form at least a portion of or be coupled to a spore substrate, or the like, or a combination thereof. Such a wicking material can include a porous wicking pad, a soaking pad, or the like, or a combination thereof, to facilitate bringing the liquid 122 into intimate contact with the spores.

In some embodiments, the frangible container 120 can be configured to facilitate fracturing of the frangible container 120 in a desired manner. For example, in some embodiments, a lower portion of the frangible container 120 can be formed of a thinner and/or weaker material, such that the lower portion preferentially fractures over another portion of the frangible container 120. In addition, in some embodiments, the frangible container 120 can include a variety of features positioned to facilitate fracturing of the frangible container 120 in a desired manner, including, but not limited to, a thin and/or weakened area, a score line, a perforation, or the like, or combinations thereof.

The frangible container 120 can have a first closed state in which the liquid 122 is contained within the frangible container 120 and a second open state in which the frangible container 120 has fractured and the liquid 122 is released into the reservoir 103 and/or the spore reservoir 136, and in fluid communication with the spores 115.

In some embodiments, the biological sterilization indicator 100 can be activated (e.g., the second portion 106 can be moved to the second position 150) manually. In some embodiments, the biological sterilization indicator 100 can be activated by a reading apparatus (e.g., as the biological sterilization indicator 100 is positioned in the reading apparatus). In some embodiments, the biological sterilization indicator 100 can be activated with a device (e.g., an activation device) independent of such a reading apparatus, for example, by positioning the biological sterilization indicator 100 in the device prior to positioning the biological sterilization indicator 100 in a well of a reading apparatus. In some embodiments, the biological sterilization indicator 100 can be activated by a combination of two or more of the reading apparatus, a device independent of the reading apparatus, and manual activation.

One or both of the biological sterilization indicator 100 and another device, such as a reading apparatus can be further configured to inhibit premature or accidental fracturing of the frangible container 120. For example, in some embodiments, the biological sterilization indicator 100, activation device, or reading apparatus can include a lock or locking mechanism that is positioned to inhibit the second portion 106 of the housing 102 from moving into the second position 150 until desired. In such embodiments, the biological sterilization indicator 100 cannot be activated until the lock is moved, removed or unlocked. In addition, or alternatively, in some embodiments, the biological sterilization indicator 100, activation device, and/or reading apparatus can include a lock or locking mechanism that is positioned to inhibit the second portion 106 of the housing 102 from moving from the second position 150 back into the first position 148 after activation.

In some embodiments, as shown in the illustrated embodiment, at least a portion of the housing can be flat (e.g., the parallel walls 168), and can be substantially planar with respect to the spore reservoir 136, and one or both of the parallel walls 168 or a portion thereof (e.g., the detection window 167) can be sized such that at least one dimension of the wall 168 (or detection window 167) substantially matches at least one dimension of the spore reservoir 136 and/or the locus of spores 115. Said another way, the wall 168 or a portion thereof (e.g., the detection window 167) can include a cross-sectional area that is substantially the same size as the cross-sectional area of the spore reservoir 136 and/or the locus of spores 115. Such size matching between the wall 168/detection window 167 and the spore reservoir 136 and/or the locus of spores 115 can maximize the signal detected during a detection or assaying process. Alternatively, or in addition, the wall 168 or detection window 167 can be sized to match the reservoir 103 (e.g., at least one dimension or the cross-sectional areas can be sized to match). Such size matching between detection zones can improve spore assaying and detection.

The biological sterilization indicator 100 illustrated in FIGS. 1-7, at least the portion of the biological sterilization indicator 100 where the spores 115 are positioned, is relatively thin (i e, the "z dimension" is minimized), such that an optical path from the spores to the wall 168 (or detection window 167) is minimized and/or any effect of interfering substances in the liquid 122 (or nutrient medium) is minimized.

In use, the biological sterilization indicator 100 can be placed along with a sterilizing batch for a sterilization process. During sterilization, a sterilant is in fluid communication with the reservoir 103 (i.e., the first chamber 109 and the second chamber 111), the spore reservoir 136, and the spores 115 primarily via the sterilant path 164, such that sterilant can reach the spores to produce sterilized spores. As described above, the cooperation of the first fluid path 160 and the second fluid path 162 can facilitate movement of the sterilant into the second chamber 111, and particularly, into the closed end 105 of the biological sterilization indicator 100. In addition, during sterilization, the frangible container 120 is in a closed state, held intact at least partially by the carrier 132 of the insert 130. When the frangible container 120 is in a closed state, the liquid 122 is protected from the sterilant and is not in fluid communication with the reservoir 103 (particularly, the second reservoir 111 formed at least partially by the lower portion 114 of the housing 102), the spore reservoir 136, the spores 115, or the sterilant path 164.

Sterilization can further include moving a sterilant from the first chamber 109 to the second chamber 111 via the first fluid path 160 when the container 120 is in the first state, and moving displaced gas (e.g., trapped air) out of the second chamber 111 via the second fluid path 162 in response to, or to facilitate, moving the sterilant from the first chamber 109 to the second chamber 111.

Following sterilization, the effectiveness of the sterilization process can be determined using the biological sterilization indicator 100. The second portion 106 of the housing 102 can be unlocked, if previously locked in the first position 148, and moved from the first position 148 (see FIG. 3) to the second position 150 (see FIG. 4) to cause activation of the biological sterilization indicator 100. Such movement of the second portion 106 can cause the frangible container 120 to move in the housing 102, for example, along the longitudinal direction $D_L$ from a position above the upper ends 159 of the projections 158 to a position within the interior of the projections 158, which can cause the frangible container 120 to fracture. Fracturing the frangible container 120 can change the frangible container 120 from its closed state to its open state and release the liquid 122 into the reservoir 103, and into fluid communication with the spore reservoir 136 and the spores 115. The liquid 122 can either include nutrient medium (e.g., germination medium) for the spores, or the liquid 122 can contact nutrient medium in a dry form (e.g., in a powdered or tablet form) to form nutrient medium, such that a mixture including the sterilized spores and nutrient medium is formed. The mixture can then be incubated prior to or during a detection or assaying process, and the biological sterilization indicator 100 can be interrogated for signs of spore growth.

Activation can further include moving the liquid 122 from the first chamber 109 to the second chamber 111 via the first fluid path 160 when the container 120 is in the second state, and moving displaced gas (e.g., trapped air) out of the second chamber 111 via the second fluid path 162 in response to, or to facilitate, moving the liquid 122 from the first chamber 109 to the second chamber 111 via the first fluid path 160.

To detect a detectable change in the spores 115, the biological sterilization indicator 100 can be assayed immediately after the liquid 122 and the spores 115 have been combined to achieve a baseline reading. After that, any detectable change from the baseline reading can be detected. The biological sterilization indicator 100 can be monitored and measured continuously or intermittently. In some embodiments, a portion of, or the entire, incubating step may be carried out prior to measuring the detectable change. In some embodiments, incubation can be carried out at one temperature (e.g., at 37° C., at 50-60° C., etc.), and measuring of the detectable change can be carried out at a different temperature (e.g., at room temperature, 25° C., or at 37° C.). The readout time of the biological sterilization indicator 100 (i.e., the time to determine the effectiveness of the sterilization process) can be, in some embodiments, less than 8 hours, in some embodiments, less than 1 hour, in some embodiments, less than 30 minutes, in some embodiments, less than 15 minutes, in some embodiments, less than 5 minutes, and in some embodiments, less than 1 minute.

EMBODIMENTS

Embodiment 1 is a biological sterilization indicator comprising:
 a housing;
 a container containing a liquid and being dimensioned to be positioned in the housing, at least a portion of the container being frangible, the container having a first state in which the container is intact and the liquid is not in fluid communication with an interior of the housing and a second state in which the container is fractured and the liquid is in fluid communication with the interior of the housing;

a first chamber in the housing in which the container is positioned when the container is in the first state;

a second chamber in the housing in which the container and the liquid are not positioned when the container is in the first state, the second chamber comprising a source of biological activity that is not in fluid communication with the liquid when the container is in the first state and that is in fluid communication with the liquid when the container is in the second state; and a substrate positioned in the housing between the first chamber and the second chamber, the substrate positioned in fluid communication with the first chamber and the second chamber, the substrate further positioned such that the substrate is not in direct contact with the source of biological activity.

Embodiment 2 is the biological sterilization indicator of embodiment 1, wherein the substrate is not in direct contact with the source of biological activity when the container is in the first state or when the container is in the second state.

Embodiment 3 is the biological sterilization indicator of embodiment 1 or 2, wherein the substrate is not in direct contact with the container when the container is in the first state.

Embodiment 4 is the biological sterilization indicator of any of embodiments 1-3, wherein the second chamber includes a volume to be interrogated to determine the lethality of a sterilization process, and wherein the substrate is positioned outside of the volume to be interrogated.

Embodiment 5 is the biological sterilization indicator of any of embodiments 1-4, wherein the substrate is not positioned in the second chamber.

Embodiment 6 is the biological sterilization indicator of any of embodiments 1-5, wherein the substrate is positioned in the first chamber.

Embodiment 7 is the biological sterilization indicator of any of embodiments 1-6, wherein the substrate is positioned in the first chamber and not the second chamber.

Embodiment 8 is the biological sterilization indicator of any of embodiments 1-7, wherein the source of biological activity is housed in a source carrier that is positioned in the second chamber, and wherein the substrate is not in direct contact with the source carrier.

Embodiment 9 is the biological sterilization indicator of any of embodiments 1-8, wherein the substrate is oriented at a non-zero and non-right angle with respect to a longitudinal direction of the biological sterilization indicator.

Embodiment 10 is the biological sterilization indicator of any of embodiments 1-9, wherein the substrate is positioned between the container and the source of biological activity when the container is in the first state.

Embodiment 11 is the biological sterilization indicator of any of embodiments 1-10, wherein the substrate at least partially defines the first chamber and the second chamber.

Embodiment 12 is the biological sterilization indicator of any of embodiments 1-11, wherein the first chamber and the second chamber are in fluid communication when the container is in the first state and the second state.

Embodiment 13 is the biological sterilization indicator of any of embodiments 1-12, wherein the substrate is positioned to control fluid flow between the first chamber and the second chamber.

Embodiment 14 is the biological sterilization indicator of any of embodiments 1-13, wherein the substrate is positioned to limit diffusion of a detectable product from the second chamber to the first chamber when the container is in the second state.

Embodiment 15 is the biological sterilization indicator of any of embodiments 1-14, wherein the substrate is positioned to control a sterilant delivery rate to the source of biological activity when the container is in the first state.

Embodiment 16 is the biological sterilization indicator of any of embodiments 1-15, wherein the substrate includes an aperture formed therein, and wherein the aperture can be dimensioned to control fluid flow between the first chamber and the second chamber.

Embodiment 17 is the biological sterilization indicator of any of embodiments 1-16, wherein the substrate is adapted to concentrate an indicator reagent when the container is in the second state and the substrate is in fluid communication with a liquid comprising the indicator reagent.

Embodiment 18 is the biological sterilization indicator of any of embodiments 1-17, wherein the substrate is adapted to selectively concentrate a first indicator reagent when the container is in the second state and the substrate is in fluid communication with a liquid comprising the first indicator reagent and a second indicator reagent.

Embodiment 19 is the biological sterilization indicator of any of embodiments 1-18, wherein the substrate comprises nylon.

Embodiment 20 is the biological sterilization indicator of any of embodiments 1-19, wherein the substrate comprises charged nylon.

Embodiment 21 the biological sterilization indicator of any of embodiments 1-20, wherein the first chamber and the second chamber each have a volume, and wherein the volume of the second chamber is no greater than 20% of the volume of the first chamber.

Embodiment 22 is the biological sterilization indicator of any of embodiments 1-21, wherein the first chamber and the second chamber each have a volume, and wherein the volume of the second chamber is no greater than 10% of the volume of the first chamber.

Embodiment 23 is the biological sterilization indicator of any of embodiments 1-22, wherein the first chamber and the second chamber each have an average cross-sectional area, and wherein the average cross-sectional area of the second chamber is no greater than 50% of the average cross-sectional area of the first chamber.

Embodiment 24 is the biological sterilization indicator of any of embodiments 1-23, wherein the first chamber and the second chamber each have an average cross-sectional area, and wherein the average cross-sectional area of the second chamber is no greater than 40% of the average cross-sectional area of the first chamber.

Embodiment 25 is the biological sterilization indicator of any of embodiments 1-24, wherein the second chamber is at least partially defined by a closed end of the housing.

Embodiment 26 is the biological sterilization indicator of any of embodiments 1-25, wherein the first chamber is in fluid communication with ambience when the container is in the first state via at least one aperture in the housing, the at least one aperture being positioned adjacent an end of the first chamber that is located opposite the first chamber from the second chamber.

Embodiment 27 is the biological sterilization indicator of any of embodiments 1-26, wherein the first chamber includes a first end positioned toward a first end of the housing and a second end positioned toward a second end of the housing, and wherein the second chamber includes a first end in fluid communication with the second end of the first chamber and a second end defined by the second end of the housing.

Embodiment 28 is the biological sterilization indicator of any of embodiments 1-27, wherein the housing includes an open end and a closed end, and wherein the first chamber is positioned adjacent the open end and the second chamber is positioned adjacent the closed end.

Embodiment 29 is the biological sterilization indicator of any of embodiments 1-28, wherein the housing includes
a first portion, and
a second portion adapted to be coupled to the first portion, the second portion being movable with respect to the first portion, when coupled to the first portion, between a first position and a second position.

Embodiment 30 is the biological sterilization indicator of embodiment 29, wherein the container is changed from the first state to the second state in response to the second portion of the housing being moved from the first position to the second position.

Embodiment 31 is the biological sterilization indicator of embodiment 29 or 30, wherein the interior of the housing is sealed from ambience when the second portion of the housing is in the second position.

Embodiment 32 is the biological sterilization indicator of any of embodiments 29-31, wherein the liquid is moved into the second chamber in response to the second portion of the housing being moved from the first position to the second position.

Embodiment 33 is the biological sterilization indicator of any of embodiments 29-32, wherein the source of biological activity is in fluid communication with ambience when the second portion of the housing is in the first position.

Embodiment 34 is the biological sterilization indicator of any of embodiments 29-33, wherein the source of biological activity is not in fluid communication with ambience when the second portion of the housing is in the second position.

Embodiment 35 is the biological sterilization indicator of any of embodiments 1-34, wherein the container includes a glass ampoule.

Embodiment 36 is the biological sterilization indicator of any of embodiments 1-35, further comprising a wall positioned between the first chamber and the second chamber.

Embodiment 37 is the biological sterilization indicator of embodiment 36, wherein the substrate is positioned adjacent the wall.

Embodiment 38 is the biological sterilization indicator of embodiment 36 or 37, wherein the substrate is positioned on a first chamber side of the wall, such that the substrate is positioned in the first chamber and is not positioned in the second chamber.

Embodiment 39 is the biological sterilization indicator of any of embodiments 36-38, wherein the wall is oriented at a non-zero and non-right angle with respect to a longitudinal direction of the biological sterilization indicator.

Embodiment 40 is the biological sterilization indicator of any of embodiments 1-39, further comprising an insert positioned in the housing, the insert configured for at least one of holding the container intact and fracturing the container.

Embodiment 41 is the biological sterilization indicator of embodiment 40, wherein the substrate is positioned between the insert and the second chamber.

Embodiment 42 is the biological sterilization indicator of embodiment 40 or 41, wherein the insert is positioned between the container and the substrate when the container is in the first state.

Embodiment 43 is the biological sterilization indicator of any of embodiments 40-42, wherein the insert is positioned adjacent the substrate.

Embodiment 44 is the biological sterilization indicator of any of embodiments 40-43, wherein the insert is positioned in the first chamber.

Embodiment 45 is the biological sterilization indicator of any of embodiments 1-44, further comprising:
a wall positioned to separate the first chamber and the second chamber; and
an insert positioned in the housing and configured for at least one of holding the container intact and fracturing the container,
wherein the substrate is positioned between the insert and the wall.

Embodiment 46 is the biological sterilization indicator of any of embodiments 1-45, further comprising:
a first fluid path positioned to fluidly couple the first chamber and the second chamber, the first fluid path positioned to allow a sterilant to move from the first chamber into the second chamber when the container is in the first state, and to allow the liquid to move from the first chamber into the second chamber when the container is in the second state; and
a second fluid path positioned to fluidly couple the second chamber and another chamber of the biological sterilization indicator, the second fluid path positioned to allow displaced gas to move from the first chamber to the second chamber as the sterilant or the liquid moves from the first chamber to the second chamber.

Embodiment 47 is the biological sterilization indicator of embodiment 46, wherein the housing includes a longitudinal direction, wherein the first chamber is positioned above the second chamber, and wherein the first fluid path and the second fluid path extend substantially longitudinally between the first chamber and the second chamber.

Embodiment 48 is the biological sterilization indicator of embodiment 46 or 47, wherein the substrate defines at least a portion of at least one of the first fluid path and the second fluid path.

Embodiment 49 is the biological sterilization indicator of any of embodiments 46-48, wherein at least a portion of the second fluid path is defined by an inner surface of the housing.

Embodiment 50 is the biological sterilization indicator of any of embodiments 46-49, wherein the second fluid path is positioned to fluidly couple the second chamber and the first chamber, the second fluid path positioned to allow displaced gas to move from the second chamber to the first chamber.

Embodiment 51 is the biological sterilization indicator of embodiment 50, wherein the first fluid path enters the second chamber at a first position, wherein the second fluid path enters the first chamber at a second position, and wherein the second position is positioned above the first position, in operation of the biological sterilization indicator.

Embodiment 52 is the biological sterilization indicator of embodiment 50 or 51, wherein the first fluid path is positioned to fluidly couple the second chamber with a proximal portion of the first chamber, and wherein the second fluid path is positioned to fluidly couple the second chamber with a distal portion of the first chamber.

Embodiment 53 is the biological sterilization indicator of any of embodiments 46-52, wherein the second chamber is at least partially filled with the liquid when the container is in the second state, wherein the liquid has a level, and wherein the second fluid path extends between a position below the level of the liquid and a position above the level of the liquid.

Embodiment 54 is the biological sterilization indicator of any of embodiments 46-53, wherein the second fluid path is at least partially defined by a channel that extends from the second chamber to a position in the biological sterilization indicator that is above the position at which the first fluid path enters the second chamber.

Embodiment 55 is the biological sterilization indicator of any of embodiments 46-54, wherein the second fluid path extends from the second chamber to a position in the biological sterilization indicator that is above the position at which the first fluid path enters the second chamber.

Embodiment 56 is the biological sterilization indicator of any of embodiments 46-55, wherein the first fluid path connects to the second chamber at a first position, wherein second fluid path connects to the second chamber at a second position, and wherein the second position is located vertically at or above the first position, in operation of the biological sterilization indicator. Embodiment 57 is the biological sterilization indicator of any of embodiments 46-56, wherein the second fluid path connects to the second chamber at a level of the second chamber that is last to fill with the liquid when the container is in the second state.

The following working examples are intended to be illustrative of the present disclosure and not limiting.

EXAMPLES

Preparatory Example—Biological Sterilization Indicators (BIs) Prepared for Use in the Examples To exemplify the present disclosure, several biological sterilization indicators (BIs) were prepared, according to the descriptions provided above and as shown in FIGS. 1-4. The particular details of the BIs used in the examples are provided below.

As shown in FIGS. 1-4, the biological sterilization indicator 100 included a housing 102, which contained a first portion 104 (e.g., a hollow tube) and a second portion 106 (e.g., a cap) that were coupled together to provide a self-contained biological sterilization indicator. The cap was molded polypropylene with general dimensions of approximately 21 mm long by 14 mm in diameter. The first portion 104 (hollow tube) was molded polycarbonate, with the general dimensions of about 52 mm long and 12 mm in diameter at top, with the shape shown in FIGS. 1-3. The total volume of the first portion 104 (e.g., a hollow tube) was approximately 3 mL.

As shown in FIGS. 1-3, the second portion (cap) 106 of the housing 102 included 6 apertures or openings 107, which provided fluid communication between the interior of the housing 102 (e.g., the reservoir 103) and ambience. A filter paper material (not shown in FIGS. 1-3) which acted as a barrier; was positioned in the sterilant path over the apertures 107 and held in place with a pressure sensitive adhesive backed paper label. The filter paper material was the same material present in the cap of currently available 3M ATTEST 1291 Rapid Readout Biological Indicators for Steam Sterilizers (available from 3M Company, St. Paul, Minn.).

The biological sterilization indicator 100 further included a frangible container 120 that contained liquid growth media 122. The frangible container 120 was made of borosilicate glass and contained the spore growth media. The media consisted of a modified Tryptic Soy Broth (TSB) containing a pH indicator bromocresol purple, and a fluorescent enzyme substrate 4-Methylumbelliferyl-alpha-D-glucoside. The ampoule was approximately 40 mm long by about 4 mm in diameter and held approximately 500 μL of media liquid. The liquid growth media 122 was the same media used in product currently available from 3M Company as 3M ATTEST 1291 Rapid Readout Biological Indicators for Steam Sterilizers.

As shown in FIGS. 1-4, the liquid media container 120 was held in place within the biological sterilization indicator 100 by an insert 130. The insert (also called a breaker) 130 served to both hold the container 120 in place and function to facilitate the controlled breakage of the container 120, which occurs during an activation step of the BI, when the second portion 106 is pushed down to break the liquid media container 120. The insert 130 was a molded polycarbonate structure with approximate dimension of 22 mm long by 9 mm wide.

The second portion 106 had a seal projection 156 positioned to contact the first end 101 of the first portion 104, at open upper end 157 of the first portion 104 to close or seal (e.g., hermetically seal) the biological sterilization indicator 100 after activation.

The biological sterilization indicator 100 further included G. stearothermophilus spores (ATCC 7953) 115 positioned in fluid communication with the first portion 104. The spores 115 were deposited in a spore reservoir 136 of a polypropylene spore carrier 135 (9 mm×4 mm). The spores 115 were deposited directly onto the polypropylene surface, and the spore reservoir 136 had a volume of approximately 15 μL.

The housing 102 included a lower portion 114 (that at least partially defined a first chamber 109) and an upper portion 116 (that at least partially defined a second chamber 111), which were partially separated by an inner partial wall or ledge 118, in which was formed an opening 117 that provided fluid communication between the first chamber 109 and the second chamber 111. The second chamber 111 was adapted to house the spores 115. The first chamber 109 was adapted to house the frangible container 120, particularly before activation. The wall 118 was angled or slanted, at a non-zero and non-right angle with respect to the longitudinal direction of the housing 102, as shown in FIGS. 1-4.

The second chamber 111, which can also be referred to as the "spore growth chamber" or "detection chamber," included a volume to be interrogated for spore viability to determine the efficacy of a sterilization process.

The liquid media container 120 was positioned and held in the first chamber 109 during sterilization and when the container 120 was unfractured. The spores 115 were housed in the second chamber 111 and in fluid communication with ambience during sterilization. The sterilant moved into the second chamber 111 (e.g., via the first chamber 109) during sterilization. Afterwards, the liquid media 122 moved into the second chamber 111 (e.g., from the first chamber 109) during activation, when the container 120 was fractured and the liquid 122 was released into the interior of the housing 102.

The first chamber 109 had a volume of about 2800 microliters (empty of all internal components). The cross-sectional area of the first chamber 109, immediately above the wall 118 was approximately 50 mm$^2$. The second chamber 111 had a volume of about 210 microliters. The cross-sectional area of the second chamber 111, immediately below the wall 118, was approximately 20 mm$^2$.

The biological sterilization indicator 100 further included a substrate 119. The substrate 119 was approximately 9 mm×8 mm in size, and was dimensioned to rest atop the wall 118. The substrate 119 was positioned between the first chamber 109 and the second chamber 111 of the biological sterilization indicator 100. The substrate 119 included an aperture 121 formed therethrough of about 3.2 mm (0.125 inch) in diameter, the hole was approximately centered in the substrate. The substrate 119 was positioned between (e.g., sandwiched between) the insert 130 and the wall 118. The substrate 119 was formed of a charged nylon, and particularly, was a reprobing, charged transfer membrane available from GE Water & Process Technologies, Trevose, Pa., under the trade designation "MAGNAPROBE" (0.45 micron pore size, 30 cm×3 m roll, Catalog No. NP0HY00010, Material No. 1226566).

The biological sterilization indicator 100 had a vent feature 162 as shown in FIG. 4, positioned to fluidly couple the second chamber 111 with the first chamber 109. Also, as shown in FIG. 4, the biological sterilization indicator 100 had a rib or protrusion 165 that was integrally formed with a wall 108 of the housing 102, which was positioned to maintain the spore carrier 135 in a desired location in the housing 102.

The housing 102 was tapered (see, e.g., the tapered portion 146 in FIG. 3) so that the cross-sectional area in the housing 102 generally decreased along the longitudinal direction $D_L$.

Example 1—Correlation of Fluorescence Readings with Growth after 24 Hours

Biological indicators (BI) of the design shown in FIGS. 1-4 and described above in the Preparatory Example were built with ~1×10$^7$ CFU of a *G. stearothermophilus* ATCC 7953 spore crop. The charged nylon substrate material was placed: (1) in a "first" location or position indicated in FIGS. 1-4 and described above, or (2) in a "second" location or position—in the first chamber 109 of the housing 102, next to the frangible container 120 but above the insert 130. Additional BI samples were prepared into which no substrate was placed. The liquid growth media 122 was the same as that used in 3M ATTEST 1291 Rapid Readout Biological Indicators for Steam Sterilizers (available from 3M Company, St. Paul, Minn.). Each BI was then run through a steam sterilization cycle of varying lengths of 1 minute, 1 minute 45 seconds, 2 minutes, 2 minutes 15 seconds, 2 minutes 30 seconds, and 3 minutes at 270° F./132° C. Gravity Steam in a H&W Steam Resistometer (available from H&W Technology LLC, Rochester, N.Y.). Following sterilization, the BI's were allowed to cool and activated in a 490 AUTOREADER reading apparatus (available from 3M Company, St. Paul, Minn.), similar to the 290 AUTOREADER reading apparatus (available from 3M Company); certain features of the 490 AUTOREADER reading apparatus are described in U.S. Publication No. 2013/0217107 and U.S. Pat. No. 9,145,573. Fluorescent readings at excitation/emission 365/460 nm were taken every 1 minute for 60 minutes. If fluorescence was detected, it was reported as "YES;" if no fluorescence was detected, it was reported as "NF" (i.e., no fluorescence). Also, after 24 hours of incubation in the reading apparatus, the BIs were removed and evaluated for growth, based on a color change in the media from purple to yellow. If the color change was observed, it was reported as "YES;" if no color change was observed, it was reported as "NO."

The results shown in Table 1 and Table 2, below, indicate a good correlation between the fluorescence results and the 24 hour growth confirmation results when the substrate is positioned in the first location for all the BIs exposed to all lengths of sterilization cycles.

The results shown in Table 3 and Table 4, below, indicate inconsistent results were observed for the BIs when the substrate was in the second location, not in the path of the media, particularly at the 2 minutes 30 seconds and 3 minute cycle times.

The results shown in Table 5 and Table 6, below, indicate inconsistent results were observed for the BIs when no substrate was present, particularly at the 2 minutes 15 seconds, 2 minutes 30 seconds and 3 minute cycle times.

TABLE 1

Substrate in first position-Fluorescence

| Cycle Time | Fluorescence; n = 5 | | | | |
|---|---|---|---|---|---|
| 1:00 | YES | YES | YES | YES | YES |
| 1:45 | YES | YES | YES | YES | YES |
| 2:00 | YES | YES | YES | YES | YES |
| 2:15 | NF | YES | NF | YES | YES |
| 2:30 | NF | NF | NF | NF | NF |
| 3:00 | NF | NF | NF | NF | NF |

TABLE 2

Substrate in first position-Growth after 24 hrs

| Cycle Time | Growth after 24 hrs; n = 5 | | | | |
|---|---|---|---|---|---|
| 1:00 | YES | YES | YES | YES | YES |
| 1:45 | YES | YES | YES | YES | YES |
| 2:00 | YES | YES | YES | YES | YES |
| 2:15 | NO | YES | NO | YES | YES |
| 2:30 | NO | NO | NO | NO | NO |
| 3:00 | NO | NO | NO | NO | NO |

TABLE 3

Substrate in second position-Fluorescence

| Cycle Time | Fluorescence; n = 5 | | | | |
|---|---|---|---|---|---|
| 1:00 | YES | YES | YES | YES | YES |
| 1:45 | YES | YES | YES | YES | YES |
| 2:00 | YES | YES | YES | YES | YES |
| 2:15 | YES | YES | YES | YES | YES |
| 2:30 | NF | NF | NF | YES | NF |
| 3:00 | NF | NF | NF | NF | NF |

TABLE 4

Substrate in second position-Growth after 24 hrs

| Cycle Time | Growth after 24 hrs; n = 5 | | | | |
|---|---|---|---|---|---|
| 1:00 | YES | YES | YES | YES | YES |
| 1:45 | YES | YES | YES | YES | YES |
| 2:00 | YES | YES | YES | YES | YES |
| 2:15 | YES | YES | YES | YES | YES |
| 2:30 | NO | NO | YES | YES | NO |
| 3:00 | NO | NO | NO | NO | NO |

TABLE 5

No Substrate-Fluorescence

| Cycle Time | Fluorescence; n = 5 | | | | |
|---|---|---|---|---|---|
| 1:00 | YES | YES | YES | YES | YES |
| 1:45 | YES | YES | YES | YES | YES |
| 2:00 | YES | YES | YES | YES | YES |
| 2:15 | YES | NF | NF | YES | YES |
| 2:30 | NF | NF | NF | NF | NF |
| 3:00 | NF | NF | NF | NF | NF |

TABLE 6

No Substrate-Growth after 24 hrs

| Cycle Time | Growth after 24 hrs; n = 5 | | | | |
|---|---|---|---|---|---|
| 1:00 | YES | YES | YES | YES | YES |
| 1:45 | YES | YES | YES | YES | YES |
| 2:00 | YES | YES | YES | YES | YES |
| 2:15 | NO | NO | YES | YES | YES |
| 2:30 | NO | NO | NO | NO | NO |
| 3:00 | NO | NO | NO | NO | NO |

Example 2—Media Flow Flick Test

The following 4 sets of biological indicator (BI) samples were prepared:
Ex. 2A) BIs were prepared as described above in the Preparatory Example.
Ex. 2B) BIs were prepared as described above except that there was no aperture 121 in the substrate 119.
Ex. 2C) BIs were prepared as described above except that a Whatman Paper* was used as the substrate (instead of nylon) and included the 3.2 mm aperture in the substrate.
*(Whatman Grade 1 Chr cellulose chromatography paper, from Whatman Inc. USA, Piscataway, N.J.)
Ex. 2D) BIs were prepared as described above except that the Whatman Paper* was used as the substrate and there was no aperture in the substrate.

The Flick Test BIs were placed in a tube holder and the caps were pushed down to activate the BIs, crushing the frangible container 120, containing the liquid growth media 122. Movement of the liquid growth media 122 was evaluated by visual inspection. If the media had not fully moved into the detection chamber 111 (evidenced by the presence of bubbles), then the BI was "flicked" by a single downward shake. After each flick, the detection chamber was again visually inspected. The number of flicks required to move all the media to the detection chamber and remove all bubbles was recorded. A higher number of flicks indicates poor flow of the liquid growth media to the detection chamber 111. The results are shown in Table 7.

TABLE 7

Media Flow Flick Test-Number of Flicks to move media to Detection Chamber

| Replicate No. | 2A GE Nylon With hole | 2B GE Nylon Without hole | 2C Whatman Paper With hole | 2D Whatman Paper Without hole |
|---|---|---|---|---|
| Replicate #1 | 0 | 0 | 0 | 0 |
| Replicate #2 | 0 | 0 | 2 | 1 |
| Replicate #3 | 0 | 0 | 2 | 1 |
| Replicate #4 | 0 | 1 | 1 | 1 |

Example 3—Substrate Adsorption of Bromocresol Purple (BCP) from a Liquid Medium

A spore growth media solution was prepared consisting of 17 grams of a bacteriological peptone, 0.17 grams of L-alanine and 0.03 grams bromocresol purple pH indicator dye, per liter of water. The pH of the nutrient medium solution was adjusted to 7.6 with 0.1 N sodium hydroxide.

To each of 60 borosilicate glass tubes (12 mL, VWR Cat #53283-802) was added 1.0 mL of the prepared growth media and capped with linerless cap closures (VWR Cat #66010-680).

Two different substrate materials were evaluated: GE charged nylon (MAGNAPROBE 0.45 micron charged nylon membrane, part number NP0HY00010, available from GE Osmonics Labstore, Minnetonka, Minn.) and paper (Whatman Grade 1 Chr cellulose chromatography paper, available from Whatman Inc. USA, Piscataway, N.J.).

Twenty strips of each of the two substrate materials were cut to size, 4 mm×10 mm. All the strips were pre-sterilized by placing them in a Propper CHEX-ALL II Instant Sealing Pouch (Propper, Manufacturing Inc., Long Island City, N.Y.) and sterilizing them for 30 minutes in a steam liquid cycle at 121° C. in an AMSCO sterilizer (Steris, Mentor, Ohio).

The sterilized substrate strips were aseptically removed from the pouch and transferred to the glass tubes, five strips of the nylon substrate per each of 20 tubes and five strips of the paper substrate per each of 20 different tubes.

Spore strips were acquired from disassembled 3M ATTEST 1292 Rapid Readout Biological Indicators for Steam Sterilizers, containing G. stearothermophilus spores, (ATCC 7953); available from 3M Company. The spore strips were cut into equal quarters, each approximately 6.4 mm×6.4 mm, and added to glass tubes according to Table 8 and further described below. One (6.4 mm×6.4 mm) piece of a 1292 ATTEST spore strip was added to each of 10 glass tubes, each containing 5 pieces of the nylon substrate and growth media. One piece of the spore strip was added to each of 10 glass tubes, each tube containing 5 pieces of the Whatman paper and growth media. One piece of spore strip was added to each of 10 glass tubes, each tube containing only growth media, no substrate. No spore strip piece was added to the remaining 30 tubes: 10 tubes containing 5 pieces of nylon substrate, 10 tubes containing 5 pieces of the paper substrate, and 10 tubes containing no substrate.

TABLE 8

Preparation of Samples for Example 3

| Sample | Number of tubes | Growth Media | 5 strips of Substrate | Spore Strip |
|---|---|---|---|---|
| 1. Nylon + spores | 10 | yes | nylon | Yes |
| 2. Nylon w/o spores | 10 | yes | nylon | None |
| 3. Paper + spores | 10 | yes | paper | Yes |
| 4. Paper w/o Spores | 10 | yes | paper | None |
| 5. Control-No substrate + spores | 10 | yes | none | Yes |
| 6. Control-No substrate w/o spores | 10 | yes | none | None |

Two tubes of each of the above samples were selected for the following observations and analyses at 1 minute time point. The color of the nylon or paper substrate material while in the tube was compared to the color of the surrounding liquid growth media as to whether the substrate was darker or lighter than the media. The color of substrate materials were observed and recorded when taken out of the glass tubes containing growth media.

The nylon and paper substrate strips were removed from the tubes and placed on a KIMWIPE (Kimberly-Clark) before densitometry readings were taken using an X-Rite 530P densitometer (X-Rite, Grand Rapids Mich.). The optical density setting on the X-Rite 530P densitometer was set to "color" to provide the "V" filter results. The X-Rite densitometer was set to "compare" for substrate results of ΔE with Pantone 2665U and 102U selected. The CIE76 formula was used to calculate the ΔE at each Pantone. The ΔE value is the distance in L*A*B colorspace from a measured point to a reference value, a Pantone color. A lower ΔE indicates a measured color is closer to the reference value. A value of about 2.5 ΔE's is about the minimum threshold for a human eye to differentiate color. The two reference values used were Pantone 2665U (a light purple) and Pantone 102U (bright yellow). Note that, because these two values are not diametrically opposed on the "color wheel", an increase in ΔE at 2665U does not necessarily mean an exact decrease in ΔE at 102U. In other words ΔE at 2665U only indicates a change relative to "purple", while ΔE at 102U only indicates a change relative to "yellow".

The color of the media in each tube was also observed and recorded. In triplicate, an amount of 200 μL of media was removed from each tube and placed in a 96 well plate (COSTAR CLS-3603-48EA black tissue culture treated 96 well plate with clear bottom) and the optical density at 590 nm and 430 nm was measured with a SYNERGY 4 spectrophotometer with Gen 5 software. The optical density (OD) measurements were taken using a monochromater, (BioTek, Winooski, Vt.).

The remaining tubes were incubated at 56° C. At each of the following times: 30 minutes, 1 hour, 4 hours and 24 hours of incubation; 2 tubes of each sample were removed from the incubator, visually observed and instrumentally measured as described above.

TABLE 9

Color Observations of Media

| Sample | 1 min | 30 min | 1 hr | 4 hrs | 24 hrs |
|---|---|---|---|---|---|
| 1. Nylon + spores | Purple | Purple | Purple | Purple | Yellow |
| 3. Paper + spores | Purple | Purple | Purple | Purple | Yellow |
| 5. Control-No substrate + spores | Purple | Purple | Purple | Purple | Yellow |
| 2. Nylon w/o spores | Purple | Purple | Purple | Purple | Purple |
| 4. Paper w/o Spores | Purple | Purple | Purple | Purple | Purple |
| 6. Control-No substrate w/o spores | Purple | Purple | Purple | Purple | Purple |

The media in all vials remained purple until after the 4 hour reading. Those samples without spores remained purple after 24 hours. All samples with spores had turned a visually yellow color by 24 hours due to growth of cells leading to a decrease in pH of the media, indicated by the bromocresol purple (BCP) pH indicator dye, turning from purple to yellow.

At each time interval, before the substrate was removed from the media, the color of the substrate was compared to that of the media. The relative difference between the color of the substrate and the media was reported. In all instances, when the nylon substrate was used as the substrate, the substrate appeared a darker shade of the color than the surrounding media. In all instances when paper was used as the substrate, the substrate appeared as a lighter shade of the color of the surrounding media. These results show that the nylon substrate is superior to the paper substrate in receiving and concentrating the indicator reagent.

TABLE 10

Substrate Color vs. Media Color

| Sample | 1 minute | 0.5 hours | 1 hour | 4 hours | 24 hours |
|---|---|---|---|---|---|
| 1. Nylon + Spores | Darker | Darker | Darker | Darker | Darker Yellow |
| 2. Nylon w/o spores | Darker | Darker | Darker | Darker | Darker |
| 3. Paper + Spores | Lighter | Lighter | Lighter | Lighter | Lighter Yellow |
| 4. Paper w/o Spores | Lighter | Lighter | Lighter | Lighter | Lighter |

In most instances "Darker" meant that the substrate was a visibly darker purple color than the media, with the exception of 24 hrs nylon with spores, which was a darker yellow color. In most instances "Lighter" meant that the substrate was a visibly lighter purple color than the media, with the exception of 24 hrs paper with spores, which was a lighter yellow color.

For the samples with spores, the optical density (OD) measurement at 590 nm at 24 hours will not show the differences in the intensity of the yellow color. Therefore, only the OD values taken at 430 nm at 24 hours were evaluated.

TABLE 11

Average Optical Density of Media at 430 nm at 24 hours

| Sample | 24 hrs |
|---|---|
| 1. Nylon + spores | 0.271 |
| 3. Paper + spores | 0.827 |
| 5. Control-no substrate + spores | 0.835 |

The 24 hour readings at 430 nm of the media samples with spores in the presence of paper substrate and the media sample with no substrate (Control) with spores, both have similar values of OD of 0.827 and 0.835 respectively, as shown in Table 11. However, the media sample with spores in the presence of nylon had an OD of only 0.271, which is 0.5 OD units less than the control or the sample with the paper substrate. This shows that the intensity of the yellow color of the media in the presence of nylon was reduced due to the nylon substrate receiving and concentrating the indicator reagent.

TABLE 12

Average Optical Density of Media at 590 nm

| Sample | 1 min | 30 min | 1 hr | 4 hr | 24 hrs |
|---|---|---|---|---|---|
| 1. Nylon with spores | 1.124 | 1.122 | 0.698 | 1.063 | *** |
| 3. Paper with spores | 1.404 | 1.786 | 1.440 | 1.697 | *** |
| 5. Control-No substrate with spores | 1.402 | 1.801 | 1.463 | 1.776 | *** |
| 2. Nylon w/o spores | 1.158 | 1.136 | 0.653 | 1.102 | 1.122 |
| 4. Paper w/o Spores | 1.435 | 1.716 | 1.468 | 1.863 | 1.708* |
| 6. Control-No substrate w/o spores | 1.345 | 1.797 | 1.465 | 1.828 | 1.812 |

All values represent n = 6 (3 readings × 2 tubes).
*n = 5 readings: 3 readings for tube 1 and 2 readings for tube 2.
*** Samples are yellow in color and therefore OD at 590 nm does not accurately measure the color of the media.

The absorbance of the control with no substrate (with and without spores) at 1 minute was considered the initial baseline OD measurement for the media. Table 12 shows that even at 1 minute the OD at 590 nm of the sample media, with spores, in the presence of the nylon, (1.124) was less than the OD of the sample media in the presence of the paper with spores (1.404) or the Control with spores (1.402). This difference indicates that the intensity of the purple color of the media was already reduced due to the nylon substrate rapidly receiving and concentrating the BCP indicator reagent. At 24 hours the OD at 590 nm of the sample media without spores in the presence of the nylon was 1.122, which is much lower than the OD of the media in the presence of paper (1.708) or the OD of the Control sample without spores, 1.812.

TABLE 13

Pantone Color of Substrate at 24 hours

| | | |
|---|---|---|
| 1. Nylon substrate + spores | Yellow | Pantone 102U |
| 2. Nylon substrate w/o spores | Purple | Pantone 1345U |
| 3. Paper substrate + spores | Yellow | Pantone 100U |
| 4. Paper substrate w/o spores | Purple | Pantone 256U |
| Initial Purple Media Color | Purple | Pantone 2665U |
| Yellow Media Color | Yellow | Pantone 102U |

TABLE 14

Average Densitometry Reading of Substrate using V filter

| Sample | 0 min | 1 min | 0.5 hrs | 1 hrs | 4 hrs | 24 hrs |
|---|---|---|---|---|---|---|
| 1. Nylon + spores | 0.05 | 0.17 | 0.30 | 0.22 | 0.26 | *** |
| 2. Nylon w/o spores | 0.05 | 0.20 | 0.24 | 0.28 | 0.26 | 0.26 |
| 3. Paper + spores | 0.11 | 0.12 | 0.26 | 0.16 | 0.12 | *** |
| 4. Paper w/o spores | 0.11 | 0.11 | 0.15 | 0.14 | 0.11 | 0.18 |

*** Substrate samples with spores at 24 hours are yellow in color and V filter does not accurately measure the color of the substrate.

TABLE 15

Average Densitometry Reading of Substrate: $\Delta$ E from Pantone 2665U (Purple)

| Sample | 0 min | 1 min | 0.5 hrs | 1 hrs | 4 hrs | 24 hrs |
|---|---|---|---|---|---|---|
| 1. Nylon + spores | 68.18 | 64.48 | 63.57 | 64.36 | 56.42 | *** |
| 2. Nylon w/o spores | 68.18 | 66.37 | 58.47 | 74.45 | 54.62 | 57.49 |
| 3. Paper + spores | 66.23 | 68.18 | 61.27 | 67.06 | 66.96 | *** |
| 4. Paper w/o spores | 66.23 | 68.70 | 65.29 | 63.69 | 67.45 | 59.31 |

*** Substrate samples with spores at 24 hours are yellow in color and V filter does not accurately measure the color of the substrate.

TABLE 16

Average Densitometry Reading of Substrate: $\Delta$ E from Pantone 102U (Yellow)

| Sample | 0 min | 24 hrs |
|---|---|---|
| Nylon substrate + Spores | 83.78 | 56.83 |
| Paper substrate + Spores | 83.67 | 76.15 |

Tables 13-16 show the densitometry readings of the substrates after exposure to media (with and without spores) for varying lengths of time. The time 0 reading for each substrate is the initial densitometry reading before the substrate sample is placed into the media. When evaluating the substrates that are purple, the V filter and the $\Delta$ E (Pantone 2665U) showed the most contrast. The average densitometry readings with the V filter for the nylon substrate as shown in Table 14 increased and remained elevated throughout the experiment (with the only exception being when the substrate was yellow at the 24 hour time point for the "with spore" sample). In contrast, the densitometry readings for the paper substrate remained fairly constant across the time points. Likewise, the nylon substrate $\Delta$ E (Pantone 2665U) value shown in Table 15 generally decreased throughout the experiment (with the only exception being when the substrate was yellow at the 24 hour time point for the "with spore" sample). This indicated the nylon substrate was receiving and concentrating the BCP indicator reagent. While in contrast, the $\Delta$ E (Pantone 2665U) value for the paper substrate remained fairly constant.

Table 16 illustrates that at the 24 hour time point the $\Delta$ E(Pantone 102U) value for the nylon substrate was considerably lower than the E(Pantone 102U) value for the paper substrate, indicating that the nylon substrate was closer to the pantone 102U color (more bright yellow) than the paper substrate.

Example 4—Nylon Substrate Adsorption of BCP from a Liquid Medium after Two 24 hr Incubations The same media and components used in Example 3 were used in Example 4. To each of 4 glass tubes was added 1.0 mL of the prepared growth media. One piece of a 1292 ATTEST spore strip cut to approximately 6.4 mm×6.4 mm was added to each glass tube. The tubes were placed in an incubator at 56° C. for 24 hours to promote the growth of the G. stearothermophilus cells. After the 24 hours incubation, five (5) strips (each cut to 4 mm×10 mm) of the nylon substrate were added to two (2) of the tubes. To the other two remaining control tubes, no nylon substrate material was added. The tubes were placed in an incubator at 56° C. for another 24 hours. After the second 24 hour incubation period (24 hours after the addition of the nylon substrate) to the tubes, the following analyses were performed: (1) from each tube three aliquots of 200 µL of media were taken and placed into in a 96 well plate and the optical density at 430 nm of the media was measured, again using the SYNERGY 4 Spectrophotometer; (2) the nylon substrate pieces were removed from the tubes, placed on a KIMWIPE to blot dry and densitometry readings of the substrate strips were taken with the X-Rite 530P densitometer.

TABLE 17

Average OD of Media at 430 nm at 48 hours; 24 hours after nylon substrate

| Sample | Average OD |
|---|---|
| Media containing nylon substrate + spores | 0.365 |
| Control media-no substrate + spores | 1.241 | n = 12 (3 readings from each of 4 tubes)
n = 3 (3 reading from the control tube)

Table 17 shows the decrease in the OD at 430 nm of the media 24 hours after the nylon substrate was added to the tubes, compared to the control, where no substrate was added. The difference in the OD measurement between the two samples indicates the difference in the amount of yellow present in the sample media. This shows that the intensity of the yellow color of the media in the presence of nylon was reduced due to the nylon substrate receiving and concentrating the indicator reagent.

TABLE 18

Average Densitometry Reading of Substrate: $\Delta$ E from Pantone 102U (Yellow)

| Sample | Avg. $\Delta$E (102U) |
|---|---|
| Nylon substrate + spores after 24 hrs in media | 37.86 |
| Nylon substrate before media | 83.78 | n = 10 (5 strips of nylon substrate × 2 tubes)

Table 18 shows the ΔE (102U) value of the nylon substrate 24 hours after being added to a tube of media with spores that had already been incubated for 24 hours. This was compared to nylon substrate that was not placed into media. The difference in the ΔE measurements between the two samples indicates that the substrate exposed to (yellow) media with growth is closer in color to pantone 102U (bright yellow) than the substrate not exposed to the media. In other words, the nylon substrate was still able to receive and concentrate the indicator reagent after two 24 hour periods of incubation and growth.

Example 5—Adsorption of BCP from a Liquid Medium by Various Substrates Materials A spore growth media solution was prepared consisting of 17 grams of a bacteriological peptone C, 0.17 grams of L-alanine and 0.03 grams bromocresol purple (BCP) pH indicator dye, per liter of water. The pH of the nutrient medium solution was adjusted to 7.6 with 0.1 N sodium hydroxide.

To each borosilicate glass tube (12 mL, VWR Cat #53283-802) was added 1.0 mL of the prepared growth media and capped with linerless cap closures (VWR Cat #66010-680).

Four different substrate materials were evaluated: (1) GE charged nylon (MAGNAPROBE 0.45 micron charged nylon membrane, part number NP0HY00010, available from GE Osmonics Labstore, Minnetonka, Minn.); (2) BIO-RAD high-strength nylon membrane positively charged with quaternary amine groups (ZETA-PROBE GT Genomics, Cat#162-0196, available from BIO-RAD LifeSciences, Hercules, Calif.); (3) 0.41M nitrocellulose (Cat# LC-2000, available from Invitrogen Corporation Carlsbad, Calif.), and (4) 0.41M polyvinylidene difluoride (PVDF) membrane (Cat# LC-2002, available from Invitrogen Corporation Carlsbad, Calif.). Several strips of each of the substrate materials were cut to size: 4 mm×10 mm, enough for one (1) strip for each glass tube.

All the strips were pre-sterilized by placing them in a Propper CHEX-ALL II Instant Sealing Pouch (Propper, Manufacturing Inc., Long Island City, N.Y.) and sterilizing them for 30 minutes in a steam liquid cycle (at 121° C.) in an AMSCO sterilizer (Steris, Mentor, Ohio). The strips were then aseptically transferred to each tube. Two tubes of each substrate were evaluated along with two control tubes that contained no substrate.

The following observations and analyses were performed at 0 time, 30 minutes, 1 hour, 4 hours and 24 hour time points: (1) the color of the substrate material in each tube was compared to the color of the surrounding media of the same tube to determine whether the substrate was darker or lighter than the surrounding media, (2) the substrate material was removed from the tube, placed on a KIMWIPE to blot dry and then densitometry readings were taken with the V filter as described above, (3) removed 200 μL of the media from each tube and transferred in triplicate into a 96 well plate (COSTAR CLS-3603-48EA black tissue culture treated 96 well plate with clear bottom) and the optical density of the media at 590 nm. was measured with a SYNERGY 4 spectrophotometer with Gen 5 software. Optical density (OD) measurements were taken using a monochromater, (BioTek, Winooski, Vt.).

The remaining tubes were incubated at 56° C. At each of the following times: 30 minutes, 1 hour, 4 hours and 24 hours of incubation; 2 tubes of each sample were removed from the incubator, visually observed and instrumentally measured as describe above.

TABLE 19

Substrate Color vs. Media Color for Various Substrates

| Time Point | GE MAGNAPROBE Nylon | Bio-Rad ZETA-PROBE Nylon | Invitrogen Nitrocellulose | Invitrogen PVDF |
|---|---|---|---|---|
| 0 hr | Lighter | Lighter | Lighter | Lighter |
| 0.5 hr | Darker | Darker | Lighter | Lighter |
| 1 hr | Darker | Darker | Lighter | Lighter |
| 4 hr | Darker | Darker | Lighter | Lighter |
| 24 hr | Darker | Darker | Lighter | Lighter |

Darker = Substrate was visibly darker purple color than the media
Lighter = Substrate was visibly lighter purple color than the media At each reading before the Substrate was removed from the media, the color of the media was visually compared to that of the substrate. The difference between the color of the substrate and the color of the media was observed and reported in the above table. After 30 minutes in contact with the media, both nylon substrate materials were visibly darker than the media and remained darker throughout the entire experiment.

TABLE 20

Average Densitometry Reading "V" of Various Substrates after Media with BCP

| Time Point | GE MAGNAPROBE Nylon | Bio-Rad ZETA-PROBE Nylon | Invitrogen Nitrocellulose | Invitrogen PVDF |
|---|---|---|---|---|
| 0 hr | 0.300 | 0.425 | 0.050 | 0.035 |
| 0.5 hr | 0.965 | 0.735 | 0.195 | 0.030 |
| 1 hr | 0.930 | 0.785 | 0.255 | 0.025 |
| 4 hr | 1.035 | 0.720 | 0.220 | 0.035 |
| 24 hr | 1.015 | 0.735 | 0.240 | 0.040 |

The above table shows the Densitometry readings of the substrate materials after exposure to media for varying lengths of time. The time 0 reading for each substrate is the initial densitometry reading within 30 seconds of the substrate being placed into the media. In all instances the nylon substrates' densitometry reading increased within 30 minutes and remained elevated throughout the experiment.

TABLE 21

OD at 590 nm of Media in presence of Various Substrate Materials

| Time Point | GE MAGNA-PROBE Nylon | Bio-Rad ZETA-PROBE Nylon | Invitrogen Nitro-cellulose | Invitrogen PVDF | Control (Media only) |
|---|---|---|---|---|---|
| 0 hr | 1.972 | 1.952 | 2.012 | 1.988 | 1.957 |
| 0.5 hr | 1.535 | 1.762 | 1.981 | 1.985 | 1.965 |
| 1 hr | 1.166 | 1.662 | 2.143 | 1.970 | 1.990 |
| 4 hr | 1.108 | 1.704 | 2.071 | 1.995 | 1.958 |
| 24 hr | 0.935 | 1.842 | 2.217 | 2.329 | 2.156 |

Table 21 shows the average optical density (OD) reading of the media removed from the tube containing each substrate material at the specified time. It is noticeable that at each time point, the OD for the media which was in the presence of either nylon substrate was lower than the OD reading for the media containing either the nitrocellulose or the PVDF. Additionally, the nitrocellulose or the PVDF show very little change in OD reading and are quite similar to the Control OD values.

Example 6—Adsorption of Methyl Red from a Liquid Medium by Nylon Substrates

A spore growth media solution was prepared consisting of 17 grams of a bacteriological peptone, 0.17 grams of L-alanine and 0.03 grams methyl red pH indicator dye, per liter of water. The pH of the nutrient medium solution was adjusted to 4.2 with 0.1 N hydrochloric acid.

To each borosilicate glass tube (12 mL, VWR Cat #53283-802) was added 1.0 mL of the prepared growth media and capped with linerless cap closures (VWR Cat #66010-680).

Two different substrate materials were evaluated: GE charged nylon (MAGNAPROBE 0.45 micron charged nylon membrane, part number NP0HY00010, available from GE Osmonics Labstore, Minnetonka, Minn.), and BIO-RAD high-strength nylon membrane positively charged with quaternary amine groups (ZETA-PROBE GT Genomics, Cat#162-0196, available from Bio-Rad LifeSciences, Hercules, Calif.). Several strips of each substrate material were cut to size: 4 mm×10 mm, enough for one (1) strip for each glass tube.

All the strips were pre-sterilized by placing them in a Propper CHEX-ALL II Instant Sealing Pouch (Propper, Manufacutring Inc., Long Island City, N.Y.) and sterilizing them for 30 minutes in a steam liquid cycle (at 121° C.) in an AMSCO sterilizer (Steris, Mentor, Ohio). The strips were then aseptically transferred to each tube.

The following observations and analyses were performed for two tubes of each substrate at 0 time, 30 minutes, 1 hour, 4 hours and 24 hour time points: (1) the substrate material was removed from the tube, placed on a KIMWIPE to blot dry and then densitometry readings were taken with the V filter as performed above, (2) the color of the substrate material in each tube was compared to the color of the surrounding media of the same tube to determine whether the substrate was darker or lighter than the surrounding media.

The remaining tubes were incubated at 56° C. At each of the following times: 30 minutes, 1 hour, 4 hours and 24 hours of incubation; 2 tubes of each sample were removed from the incubator, visually observed and instrumentally measured as describe above.

TABLE 22

Average Densitometry Reading of Nylon Substrate after Methyl Red, V filter

| Time Point | GE MAGNAPROBE Nylon | Bio-Rad ZETA-PROBE Nylon |
|---|---|---|
| 0 hr | 0.160 | 0.200 |
| 0.5 hr | 0.285 | 0.330 |
| 1 hr | 0.325 | 0.376 |
| 4 hr | 0.205 | 0.450 |
| 24 hr | 0.405 | 0.470 |

Table 22 shows the densitometry readings of the nylon substrate materials after exposure to media for a varying length of time. The time 0 reading for each substrate is the initial densitometry reading within 30 seconds of the substrate being placed into the media. In all instances the nylon substrates' densitometry reading increased within 30 minutes and remained elevated throughout the experiment.

TABLE 23

Nylon Substrate Color vs. Media Color after Methyl Red

| Time Point | GE MAGNAPROBE Nylon | Bio-Rad ZETA-PROBE Nylon |
|---|---|---|
| 0 hr | Lighter | Lighter |
| 0.5 hr | Darker | Darker |
| 1 hr | Darker | Darker |
| 4 hr | Darker | Darker |
| 24 hr | Darker | Darker |

Darker = Substrate was visibly darker than the media
Lighter = Substrate was visibly lighter than the media At each reading before the substrate materials were removed from the media, the color of the media was compared to that of the substrate. The difference between the color of the substrate and the color of the media was observed and reported. After 30 minutes in contact with the media, both of the nylon substrate materials were visibly darker than the media and remained darker throughout the entire experiment.

Example 7—Absorbance Spectrum of Bromocresol Purple (BCP)

Bromocresol purple (BCP) obtained from Sigma Chemical Co., St. Louis, Mo., (catalog number B-5880), was dissolved in phosphate buffered saline, pH 7.3, at a concentration of 0.004. The solution was placed into a quartz cuvette and the UV-visible absorbance spectrum was scanned using the 1 cm cuvette adapter provided with the TECAN Infinity M200 Plate Reader (Tecan US, Durham, N.C.). The scan parameters are presented in Table 24.

The results are shown in the graph illustrated in FIG. 8. Absorbance peaks can be seen at wavelengths of about 300 nm, about 380 nm, and about 600 nm.

TABLE 24

Scan parameters for BCP absorbance spectrum.

| Mode | Fluorescence Top Reading |
|---|---|
| Emission Wavelength Start | 380 nm |
| Emission Wavelength End | 650 nm |
| Emission Wavelength Step Size | 2 nm |
| Emission Scan Number | 136 |
| Excitation Wavelength | 350 nm |
| Bandwidth (Em) | 280 . . . 850: 20 nm |
| Bandwidth (Ex) (Range 1) | 230 . . . 295: 5 nm |
| Bandwidth (Ex) (Range 2) | 296 . . . 850: 9 nm |
| Gain | 80 Manual |
| Number of Reads | 10 |
| Integration Time | 20 ms |
| Lag Time | 0 ms |
| Settle Time | 0 ms |

Example 8—Emission Spectrum of 7-hydroxy-4-methylcoumarin (4-methylumbelliferone)

4-methylumbelliferone (4MU), catalog number m1381, obtained from Sigma Chemical Co., St. Louis, Mo., was dissolved in phosphate buffered saline, pH 7.3, at a concentration of 0.004 mg/mL. The solution was placed into a quartz cuvette and the emission spectrum was recorded using the 1 cm cuvette adapter provided with the TECAN Infinity M200 Plate Reader. The scan parameters are presented in Table 25.

The results are shown in the graph illustrated in FIG. 8. An emission peak can be seen at a wavelength of about 450 nm.

TABLE 25

Scan parameters for 4-methylumbelliferone (4MU) emission spectrum.

| Mode | Absorbance |
|---|---|
| Wavelength Start | 250 nm |
| Wavelength End | 800 nm |
| Wavelength Step Size | 2 nm |
| Scan Number | 276 |
| Bandwidth (Range 1) | 230 . . . 295: 5 nm |
| Bandwidth (Range 2) | 296 . . . 1000: 9 nm |
| Gain | 80 Manual |
| Number of Reads | 10 |
| Settle Time | 0 ms |
| Part of Plate | B1-B1 |

Example 9—Effect of BCP on the Detection of 4MU

A stock solution of 4-methylumbelliferone (4MU), prepared as described in Example 8, was serially diluted in the phosphate buffered saline to the concentrations shown in Table 26. A stock solution of bromocresol purple (BCP) was prepared in phosphate buffered saline, as described in Example 7. The bromocresol purple (0.03 mg/mL final concentration) was mixed with the respective solutions of 4MU shown in Table 26. Triplicate aliquots (100 microliters/well) of each respective solution were loaded into a 96-well plate and the fluorescence in each well was measured using a TECAN Infinity M200 Plate Reader. The excitation wavelength was 350 nm and the detection was at 420 nm. The results, listed as relative fluorescence units (RFU), are shown in Table 26. The data show that, at every concentration of 4MU tested, the presence of bromocresol purple in the solution resulted in a decrease in measurable fluorescence.

TABLE 26

Fluorescent detection of 4MU in the presence or absence of BCP

| 4MU Concentration (mg/mL) | 4MU Without BCP RFU | 4MU With BCP RFU |
|---|---|---|
| 0.004 | 9725 | 5761 |
| 0.0004 | 927 | 582 |
| 0.00004 | 128 | 94 |
| 0.000004 | 50 | 40 |
| 0 | 41 | 37 |

The results are an average of three replicates. All values are reported in Relative Fluorescence units (RFUs).

Example 10 Inhibition of Acridine Orange Detection with BCP and Methyl Red

A spore growth media solution was prepared consisting of 17 grams of a bacteriological peptone and 0.17 grams of L-alanine. A volume of 200 microliters (4) of the growth media was added to each well in two (2) 96 well plates.

A dilution series of pH indicator solutions was made for both Methy Red (MR) and bromocresol purple (BCP) starting at 4.8 g/L and diluted down to 0.75 g/L. A dilution series of acridine orange was made starting at 1:50 and diluting down to 1:800

In plate #1, 20 µL the appropriate dilution of BCP was added to each row of the plate and 20 µL of the appropriate dilution of acridine orange (AO) was added to each column of plate #1. In plate #2, 20 µL of the appropriate dilution of Methy Red was added to each row of the plate and 20 µL of the appropriate dilution of acridine orange (AO) was added to each column of plate #2. See Table 27 for set up of plate #1 and plate #2.

TABLE 27

Set up for 96 Well Plate #1 BCP and Plate #2 MR

| | Column: Initial Dilution of OA | | | | | |
|---|---|---|---|---|---|---|
| | A | B | C | D | E | F |
| Row: | 1:50 | 1:100 | 1:200 | 1:400 | 1:800 | No |
| Initial Conc. of BCP or MR | AO | AO | AO | AO | AO | AO |
| Row 1: 4.8 g/L BCP or MR | — | — | — | — | — | — |
| Row 2: 2.4 g/L BCP or MR | — | — | — | — | — | — |
| Row 3: 1.2 g/L BCP or MR | — | — | — | — | — | — |
| Row 4: 0.6 g/L BCP or MR | — | — | — | — | — | — |
| Row5: 0.3 g/L BCP or MR | — | — | — | — | — | — |
| Row 6: 0.15 g/L BCP or MR | — | — | — | — | — | — |
| Row 7: 0.075 g/L BCP or MR | — | — | — | — | — | — |
| Row 8: No pH indicator | — | — | — | — | — | — |

Plates #1 and #2 were placed into the SYNERGY 4 spectrophotometer and absorbance readings were taken at 590 nm. Additionally, fluorescence excitation/emission readings at 435 nm/530 nm were also collected.

TABLE 28A

Inhibition of Acridine Orange Detection with BCP

| Row | 1:50 AO | | 1:100 AO | | 1:200 AO | |
|---|---|---|---|---|---|---|
| Initial [BCP] | 590 nm | 435/530 nm | 590 nm | 435/530 nm | 590 nm | 435/530 nm |
| 4.8 g/L BCP | ** | 94.5 | ** | 111.0 | ** | 88.0 |
| 2.4 g/L BCP | 3.709 | 173.0 | ** | 176.5 | 3.991 | 163.0 |
| 1.2 g/L BCP | 2.189 | 267.0 | 2.243 | 299.5 | 2.427 | 338.0 |
| 0.6 g/L BCP | 1.244 | 399.0 | 1.236 | 505.5 | 1.305 | 531.5 |
| 0.3 g/L BCP | 0.726 | 552.0 | 0.713 | 717.0 | 0.645 | 717.0 |

TABLE 28A-continued

Inhibition of Acridine Orange Detection with BCP

| Row | 1:50 AO | | 1:100 AO | | 1:200 AO | |
|---|---|---|---|---|---|---|
| Initial [BCP] | 590 nm | 435/530 nm | 590 nm | 435/530 nm | 590 nm | 435/530 nm |
| 0.15 g/L BCP | 0.401 | 635.0 | 0.408 | 821.0 | 0.400 | 904.5 |
| 0.075 g/L BCP | 0.264 | 670.5 | 0.274 | 912.0 | 0.241 | 958.0 |
| 0 BCP | 0.139 | 758.5 | 0.128 | 1059.0 | 0.101 | 1114.5 |

** Signal above detection threshold of instrument

TABLE 28B

Inhibition of Acridine Orange Detection with BCP

| Row | 1:400 | | 1:800 | | No AO | |
|---|---|---|---|---|---|---|
| Initial [BCP] | 590 | 435/530 | 590 | 435/530 | 590 | 435/530 |
| 4.8 g/L BCP | ** | 73.5 | ** | 45.5 | ** | 7.5 |
| 2.4 g/L BCP | ** | 105.5 | ** | 80.5 | ** | 16.0 |
| 1.2 g/L BCP | 2.194 | 255.5 | 2.488 | 184.0 | 2.190 | 29.5 |
| 0.6 g/L BCP | 1.325 | 445.0 | 1.318 | 289.0 | 1.223 | 48.5 |
| 0.3 g/L BCP | 0.684 | 607.0 | 0.653 | 418.0 | 0.696 | 67.5 |
| 0.15 g/L BCP | 0.389 | 746.5 | 0.373 | 486.5 | 0.402 | 84.5 |
| 0.075 g/L BCP | 0.269 | 838.0 | 0.234 | 535.0 | 0.278 | 97.0 |
| 0 BCP | 0.117 | 941.0 | 0.098 | 635.5 | 0.123 | 116.0 |

** Signal above detection threshold of instrument

For all acridine orange concentrations, as the amount of bromocresol purple in solution decreased the signal generated by the acridine orange increased. In other words the presence of BCP masked the acridine orange signal. For example, for the row with an initial BCP concentration of 0.3 g/L, between about 27-36% of the acridine orange fluorescence signal is lost, compared to the row with 0 BCP.

TABLE 29A

Inhibition of Acridine Orange Detection with Methyl Red

| Row | 1:50 AO | | 1:100 AO | | 1:200 AO | |
|---|---|---|---|---|---|---|
| Initial [MR] | 590 nm | 435/530 nm | 590 nm | 435/530 nm | 590 nm | 435/530 nm |
| 4.8 g/L MR | ** | 364.0 | ** | 473.5 | ** | 540.5 |
| 2.4 g/L MR | 2.211 | 484.5 | 3.835 | 434.5 | 1.848 | 470.0 |
| 1.2 g/L MR | 2.466 | 462.0 | 1.102 | 672.5 | 0.889 | 579.0 |
| 0.6 g/L MR | 0.733 | 656.0 | 1.238 | 768.5 | 1.075 | 612.0 |
| 0.3 g/L MR | 0.571 | 722.0 | 0.412 | 996.0 | 1.693 | 882.0 |
| 0.15 g/L MR | 1.123 | 664.0 | 0.644 | 940.5 | 0.882 | 891.5 |
| 0.075 g/L MR | 0.588 | 694.0 | 0.377 | 1036.0 | 0.367 | 1066.5 |
| 0 MR | 0.566 | 741.5 | 0.390 | 1048.5 | 0.303 | 1053.5 |

** Signal above detection threshold of instrument

TABLE 29B

Inhibition of Acridine Orange Detection with Methyl Red

| Row | 1:400 AO | | 1:800 AO | | No AO | |
|---|---|---|---|---|---|---|
| Initial [MR] | 590 nm | 435/530 nm | 590 nm | 435/530 nm | 590 nm | 435/530 nm |
| 4.8 g/L MR | 0.517 | 390.0 | ** | 329.0 | ** | 27.0 |
| 2.4 g/L MR | 1.806 | 476.5 | 3.764 | 248.0 | 3.236 | 35.0 |
| 1.2 g/L MR | 3.938 | 401.5 | 2.821 | 327.0 | 2.488 | 48.5 |
| 0.6 g/L MR | 1.883 | 599.0 | 1.571 | 456.5 | 1.604 | 71.0 |
| 0.3 g/L MR | 0.892 | 733.0 | 1.398 | 478.5 | 0.879 | 81.5 |
| 0.15 g/L MR | 0.751 | 741.5 | 0.441 | 543.0 | 0.330 | 93.5 |
| 0.075 g/L MR | 0.292 | 891.5 | 0.293 | 622.0 | 0.245 | 109.0 |
| 0 MR | 0.275 | 876.0 | 0.232 | 658.0 | 0.247 | 116.5 |

** Signal above detection threshold of instrument

Like BCP, the methyl red also masked the acridine orange fluorescence signal. The higher the concentration of methyl red the lower the detected fluorescence signal of acridine orange. For example, for the row with an initial methyl red concentration of 0.3 g/L, between about 3-27% of the acridine orange fluorescence signal is lost, compared to the row with no methyl red.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A biological sterilization indicator comprising:
   a housing;
   a container containing a liquid and being dimensioned to be positioned in the housing, at least a portion of the container being frangible, the container having a first state in which the container is intact and the liquid is not in fluid communication with an interior of the housing and a second state in which the container is fractured and the liquid is in fluid communication with the interior of the housing;
   a first chamber in the housing in which the container is positioned when the container is in the first state;
   a second chamber in the housing in which the container and the liquid are not positioned when the container is in the first state, the second chamber comprising a source of biological activity that is not in fluid communication with the liquid when the container is in the first state and that is in fluid communication with the liquid when the container is in the second state;
   a flange, formed from the housing, comprising an opening that separates the first chamber and the second chamber; and
   a substrate positioned in the first chamber adjacent the flange and dimensioned to rest atop of the wall, the substrate positioned in fluid communication with the first chamber and the second chamber, the substrate is adapted to collect broken portions of the container when the container is in the second state, the substrate further positioned between the container and the source of biological activity such that the substrate is not in direct contact with the source of biological activity, wherein the substrate includes an aperture formed therein that is approximately centered in the substrate, and wherein the aperture can be dimensioned to control fluid flow between the first chamber and the second chamber.

2. The biological sterilization indicator of claim 1, wherein the second chamber includes a volume to be interrogated to determine the lethality of a sterilization process, and wherein the substrate is positioned outside of the volume to be interrogated.

3. The biological sterilization indicator of claim 1, wherein the substrate is positioned in the liquid when the container is in the second state.

4. The biological sterilization indicator of claim 1, wherein the substrate at least partially defines the first chamber and the second chamber.

5. The biological sterilization indicator of claim 1, wherein the source of biological activity is housed in a source carrier, and wherein the substrate is not in direct contact with the source carrier.

6. The biological sterilization indicator of claim 1, wherein the flange and the substrate are oriented at a non-zero and non-right angle with respect to a longitudinal direction of the biological sterilization indicator.

7. The biological sterilization indicator of claim 1, wherein the substrate is adapted to concentrate an indicator reagent when the container is in the second state and the substrate is in fluid communication with a liquid comprising the indicator reagent.

8. The biological sterilization indicator of claim 1, wherein the substrate is adapted to selectively concentrate an inhibitor when the container is in the second state and the substrate is in fluid communication with a liquid comprising the inhibitor.

9. The biological sterilization indicator of claim 1, wherein the substrate is adapted to selectively concentrate a first indicator reagent when the container is in the second state and the substrate is in fluid communication with a liquid comprising the first indicator reagent and a second indicator reagent.

10. The biological sterilization indicator of claim 1, wherein the substrate comprises nylon.

11. The biological sterilization indicator of claim 1, wherein the substrate comprises charged nylon.

12. The biological sterilization indicator of claim 1, wherein the substrate is positioned to limit diffusion of a detectable product from the second chamber to the first chamber when the container is in the second state.

13. The biological sterilization indicator of claim 1, wherein the substrate is formed of a different material than the housing.

14. The biological sterilization indicator of claim 1, wherein the substrate does not form a portion of an internal or external wall positioned to define at least a portion of the first chamber or the second chamber.

15. The biological sterilization indicator of claim 1, further comprising: an insert comprising an opening formed in the insert and an open space around the insert such that the opening defines a fluid path that allows the liquid to reach the source of biological activity, the insert is adapted to hold the container such that the container is held intact in a location separate from the source of biological activity during sterilization.

16. The biological sterilization indicator, wherein the substrate is positioned between the insert and the wall.

* * * * *

UNITED STATES PATENT AND TRADEMARK OFFICE
CERTIFICATE OF CORRECTION

PATENT NO. : 10,047,334 B2
APPLICATION NO. : 15/064918
DATED : August 14, 2018
INVENTOR(S) : Sailaja Chandrapati It is certified that error appears in the above-identified patent and that said Letters Patent is hereby corrected as shown below:

In the Specification

Column 7
Line 14        Delete "Pa)" and insert -- Pa). --, therefor.
Line 46        Delete "-glucosaminodase," and insert -- -glucosaminidase, --, therefor.

Column 9
Lines 46-47    Delete "polythyene," and insert -- polythene, --, therefor.

Column 14
Lines 36-37    Delete ", and in some embodiments, no greater than about mm$^2$".

Column 18
Line 27        Delete "bromphenol" and insert -- bromophenol --, therefor.
Lines 27-28    Delete "bromthymol" and insert -- bromothymol --, therefor.
Line 30        Delete "bromphenol" and insert -- bromophenol --, therefor.
Line 31        Delete "tetrabromphenol" and insert -- tetrabromophenol --, therefor.
Line 32        Delete "bromthymol" and insert -- bromothymol --, therefor.

Column 19
Line 18        Delete "-methylumbellifery1)" and insert -- -methylumbelliferyl) --, therefor.
Line 22        After "methylumbelliferyl" insert -- β-D-N, --.
Line 22        Delete "N'diacetyl" and insert -- N'-diacetyl --, therefor.
Line 35        After "methylumbelliferyl" insert -- β-D-N, --.
Line 59        Delete "-amido4methyl" and insert -- -amido-4-methyl --, therefor.

Column 23
Line 46        Delete "cellibiose," and insert -- cellobiose, --, therefor.
Line 60        Delete "bromthymol" and insert -- bromothymol --, therefor.
Line 66        Delete "bromcresol" and insert -- bromocresol --, therefor.

Signed and Sealed this
Thirtieth Day of July, 2019

Andrei Iancu
*Director of the United States Patent and Trademark Office*

CERTIFICATE OF CORRECTION (continued)
U.S. Pat. No. 10,047,334 B2

Column 24
Line 8            Delete "bromcresol" and insert -- bromocresol --, therefor.

Column 43
Line 40          Delete "(i e," and insert -- (i.e., --, therefor.

Column 49
Lines 31-32     Delete "Biological Sterilization Indicators (BIs)" and insert -- Biological Sterilization Indicators (BSIs) --, therefor.
Line 35          Delete "(BIs)" and insert -- (BSIs) --, therefor.

Column 55
Line 29          Delete "monochromater," and insert -- monochromator, --, therefor.

Column 59
Line 35          Delete "0.41M" and insert -- 0.2 µM --, therefor.
Line 37          Delete "0.41M" and insert -- 0.2 µM --, therefor.
Lines 64-65     Delete "monochromater," and insert -- monochromator, --, therefor.

Column 61
Line 31          Delete "Manufacutring" and insert -- Manufacturing --, therefor.

Column 62
Line 37          Delete "Infinity" and insert -- Infinite --, therefor.

Column 63
Line 4            Delete "Infinity" and insert -- Infinite --, therefor.
Line 39          Delete "Infinity" and insert -- Infinite --, therefor.

Column 64
Line 19          Delete "(4)" and insert -- (µL) --, therefor.
Line 22          Delete "Methy" and insert -- Methyl --, therefor.
Line 25          After "1:800" insert -- . --.
Line 30          Delete "Methy" and insert -- Methyl --, therefor.
Line 47          Delete "Row5:" and insert -- Row 5: --, therefor.

In the Claims

Column 68
Line 56          Claim 16, delete "indicator," and insert -- indicator of claim 1, --, therefor.